(12) United States Patent
Eckelman et al.

(10) Patent No.: US 11,965,017 B2
(45) Date of Patent: *Apr. 23, 2024

(54) SERPIN FUSION POLYPEPTIDES AND METHODS OF USE THEREOF

(71) Applicant: InhibRx, Inc., La Jolla, CA (US)

(72) Inventors: Brendan P. Eckelman, La Jolla, CA (US); John C. Timmer, La Jolla, CA (US); Peter L. Nguy, La Jolla, CA (US); Grant B. Guenther, La Jolla, CA (US); Quinn Deveraux, La Jolla, CA (US)

(73) Assignee: InhibRx, Inc., La Jolla, CA (US)

( * ) Notice: Subject to any disclaimer, the term of this patent is extended or adjusted under 35 U.S.C. 154(b) by 322 days.

This patent is subject to a terminal disclaimer.

(21) Appl. No.: 17/066,410

(22) Filed: Oct. 8, 2020

(65) Prior Publication Data

US 2021/0024613 A1 Jan. 28, 2021

Related U.S. Application Data

(63) Continuation of application No. 16/393,619, filed on Apr. 24, 2019, now abandoned, which is a continuation of application No. 15/875,010, filed on Jan. 19, 2018, now Pat. No. 10,723,785, which is a continuation of application No. 14/616,363, filed on Feb. 6, 2015, now Pat. No. 10,730,929, which is a continuation of application No. 13/536,976, filed on Jun. 28, 2012, now Pat. No. 8,980,266.

(60) Provisional application No. 61/638,168, filed on Apr. 25, 2012, provisional application No. 61/577,204, filed on Dec. 19, 2011, provisional application No. 61/570,394, filed on Dec. 14, 2011, provisional application No. 61/502,055, filed on Jun. 28, 2011.

(51) Int. Cl.
| | | |
|---|---|---|
| C07K 14/81 | (2006.01) | |
| A61K 38/00 | (2006.01) | |
| C07K 14/76 | (2006.01) | |
| C07K 14/765 | (2006.01) | |
| C07K 16/40 | (2006.01) | |
| C07K 14/525 | (2006.01) | |
| C07K 14/715 | (2006.01) | |
| C07K 16/24 | (2006.01) | |

(52) U.S. Cl.
CPC .......... *C07K 14/8125* (2013.01); *A61K 38/00* (2013.01); *C07K 14/76* (2013.01); *C07K 14/765* (2013.01); *C07K 14/811* (2013.01); *C07K 14/8121* (2013.01); *C07K 16/40* (2013.01); *C07K 14/525* (2013.01); *C07K 14/7151* (2013.01); *C07K 14/7155* (2013.01); *C07K 16/241* (2013.01); *C07K 2317/52* (2013.01); *C07K 2317/522* (2013.01); *C07K 2317/524* (2013.01); *C07K 2317/526* (2013.01); *C07K 2317/53* (2013.01); *C07K 2317/56* (2013.01); *C07K 2319/00* (2013.01); *C07K 2319/30* (2013.01); *C07K 2319/31* (2013.01); *C07K 2319/70* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 5,595,756 A | 1/1997 | Bally et al. |
| 5,734,014 A | 3/1998 | Ishima et al. |
| 6,737,056 B1 | 5/2004 | Presta |
| 6,797,493 B2 | 9/2004 | Sun et al. |
| 7,045,318 B2 | 5/2006 | Ballance |
| 7,253,264 B1 | 8/2007 | Lauffer et al. |
| 7,271,149 B2 | 9/2007 | Glaesner et al. |
| 7,399,746 B2 | 7/2008 | Congote |
| 7,427,595 B1 | 9/2008 | Zhu et al. |
| 7,563,441 B2 | 7/2009 | Graus et al. |

(Continued)

FOREIGN PATENT DOCUMENTS

| | | |
|---|---|---|
| CA | 2758445 A1 | 10/2010 |
| CN | 1561220 A | 1/2005 |

(Continued)

OTHER PUBLICATIONS

Skolnick et al (Trends Biotechnol. Jan. 2000;18(1):34-9) (Year: 2000).*

(Continued)

*Primary Examiner* — Brian Gangle
*Assistant Examiner* — Andrea K McCollum
(74) *Attorney, Agent, or Firm* — COOLEY LLP; Ivor R. Elrifi; Cynthia A. Kozakiewicz

(57) ABSTRACT

This invention relates to molecules, particularly polypeptides, more particularly fusion proteins that include a serpin polypeptide or an amino acid sequence that is derived from a serpin and second polypeptide comprising of at least one the following: an Fc polypeptide or an amino acid sequence that is derived from an Fc polypeptide; a cytokine targeting polypeptide or a sequence derived from a cytokine targeting polypeptide; a whey acidic protein (WAP) domain containing polypeptide or a sequence derived from a WAP containing polypeptide; and an albumin polypeptide or an amino acid sequence that is derived from a serum albumin polypeptide. This invention also relates to methods of using such molecules in a variety of therapeutic and diagnostic indications, as well as methods of producing such molecules.

5 Claims, 9 Drawing Sheets
Specification includes a Sequence Listing.

(56) References Cited

U.S. PATENT DOCUMENTS

| | | |
|---|---|---|
| 8,252,905 B2 | 8/2012 | Furusako et al. |
| 8,633,305 B2 | 2/2014 | Shapiro |
| 8,969,526 B2 | 3/2015 | Baehner et al. |
| 8,980,266 B2 | 3/2015 | Eckelman et al. |
| 8,986,688 B2 | 3/2015 | Timmer et al. |
| 9,914,765 B2 | 3/2018 | Timmer et al. |
| 9,920,109 B2 | 3/2018 | Eckelman et al. |
| 10,400,029 B2 * | 9/2019 | Eckelman .......... C07K 14/7155 |
| 10,723,785 B2 | 7/2020 | Eckelman et al. |
| 10,730,929 B2 | 8/2020 | Eckelman et al. |
| 11,046,752 B2 | 6/2021 | Eckelman et al. |
| 2002/0081607 A1 | 6/2002 | Ruben et al. |
| 2003/0040097 A1 * | 2/2003 | Ruben .................... A61P 25/28 435/325 |
| 2003/0069395 A1 | 4/2003 | Sato et al. |
| 2003/0073217 A1 | 4/2003 | Barr et al. |
| 2003/0190311 A1 | 10/2003 | Dall'Acqua et al. |
| 2003/0190331 A1 | 10/2003 | Francon et al. |
| 2005/0276799 A1 | 12/2005 | Hinton et al. |
| 2006/0030527 A1 | 2/2006 | Mjalli et al. |
| 2006/0040867 A1 | 2/2006 | Shapiro |
| 2006/0073132 A1 | 4/2006 | Congote |
| 2006/0173170 A1 | 8/2006 | Chamberlain et al. |
| 2006/0276633 A1 | 12/2006 | Jung et al. |
| 2006/0292643 A1 | 12/2006 | Goletz et al. |
| 2007/0004909 A1 | 1/2007 | Johnson et al. |
| 2007/0041907 A1 | 2/2007 | Ober |
| 2008/0131399 A1 * | 6/2008 | Ballance ................. A61P 15/08 424/85.7 |
| 2008/0171689 A1 | 7/2008 | Williams et al. |
| 2009/0041770 A1 | 2/2009 | Chamberlain et al. |
| 2009/0304696 A1 | 12/2009 | Lawson et al. |
| 2010/0087627 A1 | 4/2010 | Marshall et al. |
| 2010/0247515 A1 | 9/2010 | Steward et al. |
| 2010/0256065 A1 | 10/2010 | Filbin et al. |
| 2010/0261248 A1 | 10/2010 | Kim et al. |
| 2010/0267932 A1 | 10/2010 | Eon-Duval et al. |
| 2011/0002888 A1 | 1/2011 | Rosen et al. |
| 2011/0021416 A1 | 1/2011 | Shapiro |
| 2011/0021755 A1 | 1/2011 | Lazar et al. |
| 2012/0056065 A1 | 3/2012 | Andersson |
| 2012/0094356 A1 | 4/2012 | Chung et al. |
| 2013/0011386 A1 | 1/2013 | Brezki et al. |
| 2013/0011398 A1 | 1/2013 | Eckelman et al. |
| 2013/0011399 A1 | 1/2013 | Timmer et al. |
| 2013/0058919 A1 | 3/2013 | Lazar et al. |
| 2014/0051834 A1 | 2/2014 | Hoffman et al. |
| 2015/0104410 A1 | 4/2015 | Eckelman et al. |
| 2015/0147325 A1 | 5/2015 | Eckelman et al. |
| 2017/0190762 A1 | 7/2017 | Strom |
| 2018/0179264 A1 | 6/2018 | Eckelman et al. |
| 2020/0102371 A1 | 4/2020 | Eckelman et al. |
| 2021/0002352 A1 | 1/2021 | Eckelman et al. |
| 2022/0324944 A1 | 10/2022 | Eckelman et al. |

FOREIGN PATENT DOCUMENTS

| | | |
|---|---|---|
| CN | 103476795 A | 12/2013 |
| CN | 103930124 A | 7/2014 |
| CN | 203917563 U | 11/2014 |
| EP | 0662516 A1 | 7/1995 |
| EP | 0628639 B1 | 6/1999 |
| EP | 1832599 A2 | 9/2007 |
| EP | 1889908 A1 | 2/2008 |
| EP | 2498799 A1 | 9/2012 |
| EP | 2537864 A1 | 12/2012 |
| EP | 2726093 A2 | 5/2014 |
| JP | 2002-537810 A | 11/2002 |
| JP | 2004-537970 A | 12/2004 |
| JP | 2007-504144 A | 3/2007 |
| JP | 2007505643 A | 3/2007 |
| JP | 2007537992 A | 12/2007 |
| JP | 2008506635 A | 3/2008 |
| JP | 2011-502126 A | 1/2011 |
| JP | 2014-519852 A | 8/2014 |
| JP | 2015-504675 A | 2/2015 |
| JP | 2016-500371 A | 1/2016 |
| RU | 2232760 C2 | 7/2004 |
| WO | WO 94/04697 A1 | 3/1994 |
| WO | WO 00/52160 A1 | 9/2000 |
| WO | WO 01/01748 A2 | 1/2001 |
| WO | WO 01/40249 A1 | 6/2001 |
| WO | WO 02/50287 A2 | 6/2002 |
| WO | WO 02/060919 A2 | 8/2002 |
| WO | WO 03/021273 A2 | 3/2003 |
| WO | WO 2004/039397 A1 | 5/2004 |
| WO | WO 2004/092219 A2 | 10/2004 |
| WO | WO 2005/019434 A2 | 3/2005 |
| WO | WO 2005/047334 A1 | 5/2005 |
| WO | WO 2005/086915 A2 | 9/2005 |
| WO | WO 2006/053301 A2 | 5/2006 |
| WO | WO 2007/011363 A2 | 1/2007 |
| WO | WO 2007/014123 A2 | 2/2007 |
| WO | WO 2007/021807 A1 | 2/2007 |
| WO | WO 2007/062188 A2 | 5/2007 |
| WO | WO 2007/085084 A1 | 8/2007 |
| WO | WO 2007/117440 A2 | 10/2007 |
| WO | WO 2008138017 A2 | 11/2008 |
| WO | WO 2008/147143 A2 | 12/2008 |
| WO | WO 2009/045508 A1 | 4/2009 |
| WO | WO 2009/083880 A1 | 7/2009 |
| WO | WO 2009/158432 A2 | 12/2009 |
| WO | WO 2010/011096 A1 | 1/2010 |
| WO | WO 2010/080538 A1 | 7/2010 |
| WO | WO 2010/123290 A2 | 10/2010 |
| WO | WO 2010/115998 A3 | 1/2011 |
| WO | WO 2011/107505 A1 | 9/2011 |
| WO | WO 2012/003290 A2 | 1/2012 |
| WO | WO 2012/178102 A2 | 12/2012 |
| WO | WO 2013/003641 A2 | 1/2013 |
| WO | WO 2013/003649 A2 | 1/2013 |
| WO | WO 2013/192131 A1 | 12/2013 |
| WO | WO 2014/001325 A1 | 1/2014 |
| WO | WO 2014/020056 A1 | 2/2014 |

OTHER PUBLICATIONS

Burgess et al. (J. Cell Biol. 111:2129-2138, 1990) (Year: 1990).*

Miosge (Proc Natl Acad Sci U S A. Sep. 15, 2015;112(37): E5189-98) (Year: 2015).*

Bork (Genome Research, 2000,10:398-400) (Year: 2000).*

Holt et al (Protein Engineering, Design & Selection vol. 21 No. 5 pp. 283-288, 2008) (Year: 2008).*

Stork et al (Protein Eng Des Sel. Nov. 2007;20(11):569-76. doi: 10.1093/protein/gzm061. Epub Nov. 3, 2007) (Year: 2007).*

Kenanova et al (Protein Engineering, Design & Selection vol. 23 No. 10 pp. 789-798, 2010) (Year: 2010).*

Vajdos et al. (J Mol Biol. Jul. 5, 2002;320(2):415-28 (Year: 2002).*

Brown et al. (J Immunol. May 1996; 156(9):3285-91) (Year: 1996).*

GenBank Accession No. NM_001135851.1, "Pan troglodytes peptidase inhibitor 3 (PI3), mRNA," Jun. 26, 2020, 2 pages.

Office Action issued in CN application No. 201910871347.6, dated Nov. 23, 2022, 22 pages.

Vanhove, B. et al., "Selective blockade of CD28 and not CTLA-4 with a single-chain Fv-alpha1-antitrypsin fusion antibody" Blood, Jul. 15, 2003, 102(2):564-570.

Bork, P., "Powers and pitfalls in sequence analysis: the 70% hurdle," Genome Res., 2000, 10:398-400.

Burgess et al., "Possible Dissociation of the Heparin-binding and Mitogenic Activities of Heparin-binding (Acidic Fibroblast) Growth Factor-1 from Its Receptor-binding Activities By Site-directed Mutagenesis of a Single Lysine Residue," Journal of Cell Biology, Nov. 1990, 111:2129-2138.

Kita, S., et al., "Competitive Binding of Musclin to Natriuretic Peptide Receptor 3 With Atrial Natriuretic Peptide," The Journal of Endocrinology, Epub 25, Feb. 25, 2009, 201(2):287-295.

Miosge et al. "Comparison of predicted and actual consequences of missense mutations," PNAS, Aug. 12, 2015, E5189-E5198.

(56) References Cited

OTHER PUBLICATIONS

Scerri et al., "pH 7 is neutral | 5 ideas in chemistry that must die", Jul. 15, 2015, pp. 1-2, Retrieved from the Internet: https://edu.rsc.org/opinion/five-ideas-in-chemical-education-that-mustdie-ph-7-is-neutral/2010031.article, 2 pages.

Skolnick J., et al., "From Genes to Protein Structure and Function: Novel Applications of Computational Approaches In The Genomic Era," Trends in Biotechnology, Jan. 2000, 18:34-39.

Thermo Scientific™ Pierce™ Gentle Ag/Ab Elution Buffer, pH 6.6. Ensure high-yield, nondenaturing antibody purification using IgG affinity purification supports with these gentle buffer solutions. Retrieved from the internet on Apr. 14, 2022 at www.fishersci.com/shop/products/pierce-gentle-ag-ab-elution-buffer-ph-6-6/p-7184436, 2 pages.

Abe et al. "Expression of the Secretory Leukoprotease Inhibitor Gene in Epithelial Cells." J. Clin. Invest., 1991, 87(6), 2207-2215.

Auerbach et al. "Angiogenesis assays: Problems and pitfalls," Cancer and Metastasis Reviews, 2000, 19, 167-172.

Ashcroft et al. "Secretory Leukocyte Protease Inhibitor Mediates Non-Redundant Functions Necessary for Normal Wound Healing." Nat. Med., 2000, 6(10), 1147-1153.

Ashkenazi et al. "Immunoadhesins as research tools and therapeutic agents" Current Opinion in Immunology, Apr. 1997, 9(2), 195-200.

Baldrick. "Pharmaceutical Excipient Development: The Need for Preclinical Guidance." Reg. Toxicol. Pharmacol., 2000, 32(2), 210-218.

Bergenfeldt et al. "Release of Neutrophil Proteinase 4(3) and Leukocyte Elastase During Phagocytosis and Their Interaction with Proteinase Inhibitors." Scand. J. Clin. Lab. Invest. 1992, 52(8), 823-829.

Bergenfeldt et al. "The Elimination of Secretory Leukocyte Protease Inhibitor (SLPI) after Intravenous Injection in Dog and Man." Scand. J. Clin. Lab. Invest., 1990, 50, 729-737.

Bingle et al. "The Putative ovarian tumor marker gene HE4 (WFDC2), is expressed in normal tissues and undergoes complex alternative splicing to yield multiple protein isoforms." Oncogene, Apr. 18, 2002, 21(17), 2768-2773.

Blumberg et al. "Unraveling the autoimmune translational research process layer by layer." Nat Med., 2015, 18(1), 35-41.

Carrell, et al. "Structure and variation of human α1-antitrypsin." Nature, 1982, 298, 329-334.

Charman. "Lipids, Lipophilic Drugs, and Oral Drug Delivery: Some Emerging Concepts." J. Pharm. Sci., 2000, 89(8), 967-978.

Charnow and Ashkenazi. "Immunoadhesins: principles and applications." Trends in Biotechnology, 1996,14, 52-60.

Chattopadhyay et al. "Salivary Secretory Leukocyte Protease Inhibitor and Oral Candidiasis in Human Immunodeficiency Virus Type 1-Infected Persons." Infect. Immun., 2004, 72(4), 1956-1963.

Clinical Trials Identifier: NTC01183468. ClinicalTrials.gov Nov. 8, 2012. Web. Nov. 15, 2013. clinicaltrials.gov/archive/NCT01183468/2012_11_08.

Clinical Trials Identifier: NTC01304537. ClinicalTrials.gov Feb. 19, 2013. Web. Nov. 15, 2013. clinicaltrials.gov/archive/NCT01304537/2013_02_19.

Clinical Trials Identifier: NTC01319331. ClinicalTrials.gov Jan. 8, 2013. Web. Nov. 15, 2013. clinicaltrials.gov/archive/NCT01319331/2013_01_08.

Clinical Trials Identifier: NTC01523821. ClinicalTrials.gov Dec. 18, 2012. Web. Nov. 15, 2013. clinicaltrials.gov/archive/NCT01523821/2012_12_18.

Cowan et al. "Elafin, a Serine Elastase Inhibitor, Attenuates Post-Cardiac Transplant Coronary Arteriopathy and Reduces Myocardial Necrosis in Rabbits After Heterotropic Cardiac Transplantation." J. Clin. Invest., 1996, 97(11), 2452-2468.

Czajkowsky D.M. et al., "Fc-fusion proteins: new developments and future perspectives." EMBO Mol. Med., Jul. 26, 2012, 4(10), 1015-1028.

Dall'Acqua, W. F. et al. "Increasing the affinity of a human IgG1 for the neonatal Fc receptor: biological consequences", J Immunol., Nov. 1, 2002, 169(9), 5171-80.

Dall'Acqua et al. "Properties of Human IgG1s Engineered for Enhanced Binding to the Neonatal Fc Receptor (FcRn)." J. Biol. Chem., 2006, 281(33), 23514-23524.

Ding et al. "Secretory Leukocyte Protease Inhibitor Interferes with Uptake of Lipopolysaccharide by Macrophages." Infect. Immun., 1999, 67(9), 4485-4489.

Doumas et al. "Anti-Inflammatory and Antimicrobial Roles of Secretory Leukocyte Protease Inhibitor." Infect. Immun., 2005, 73(2), 1271-1274.

Eisenberg et al. "Location of the Protease-Inhibitory Region of Secretory Leukocyte Protease Inhibitor." J. Biol. Chem., 1990, 265(14), 7976-7981.

European Search Report issued for Application Serial No. EP12804863 dated Jul. 16, 2015.

European Search Report issued for Application Serial No. EP15854670.5 dated Jan. 4, 2019.

Exhibit A. Thulborn, et al. "Neutrophil elastase as a biomarker for bacterial infection in COPD." Respir Res. Jul. 30, 2019, 20(1):170. doi: 10.1186/s12931-019-1145-4.

Exhibit B. Chalmers, et al. "Neutrophil Elastase Activity Is Associated with Exacerbations and Lung Function Decline in Bronchiectasis." Am J Respir Crit Care Med., May 15, 2017, 195(10), 1384-1393. doi: 10.1164/rccm.201605-1027OC.

Exhibit C. Lerman, et al. "Neutrophil elastase in the tumor microenvironment." Steroids., May 2018, 133, 96-101. doi: 10.1016/j.steroids.2017.11.006.

Exhibit D. Mehta, et al. "Neutrophil function in ischemic heart disease." Circulation, Mar. 1989, 79(3), 549-56. doi: 10.1161/01.cir.79.3.549.

Exhibit E. Muley, et al. "Neutrophil elastase induces inflammation and pain in mouse knee joints via activation of proteinase-activated receptor-2." Br J Pharmacol., Feb. 2016, 173(4), 766-77. doi: 10.1111/bph.13237.

Exhibit F. Gouni-Berthold, et al. "Neutrophil-elastase in chronic inflammatory bowel disease: a marker of disease activity?" Hepatogastroenterology. Jul.-Aug. 1999, 46(28), 2315-20.

Exhibit G. Mirea, et al. "Increased proteinase 3 and neutrophil elastase plasma concentrations are associated with non-alcoholic fatty liver disease (NAFLD) and type 2 diabetes." Mol Med. May 2, 2019, 25(1):16. doi: 10.1186/s10020-019-0084-3.

Exhibit H. Arafat, et al. "Elevated Neutrophil Elastase in Tears of Ocular Graft-Versus-Host Disease Patients." Am J Ophthalmol., Apr. 2017, 176, 46-52. doi: 10.1016/j.ajo.2016.12.026.

Exhibit I. Kaplan. "Neutrophils in the pathogenesis and manifestations of SLE." Nat Rev Rheumatol. Sep. 27, 2011;7(12):691-9. doi: 10.1038/nrrheum.2011.132.

Exhibit J. Wang, et al. "Increased neutrophil elastase and proteinase 3 and augmented NETosis are closely associated with β-cell autoimmunity in patients with type 1 diabetes." Diabetes, Dec. 2014, 63(12), 4239-48. doi: 10.2337/db14-0480.

Exhibit K. Nomura, et al. "Multifaceted Analyses of Epidermal Serine Protease Activity in Patients with Atopic Dermatitis." Int J Mol Sci., Jan. 30, 2020, 21(3), 913. doi: 10.3390/ijms21030913.

Fath et al. "Interaction of Secretory Leukocyte Protease Inhibitor with Heparin Inhibits Proteases Involved in Asthma." J. Biol. Chem. 1998, 273(22), 13563-13569.

Feuerstein. "Inflammation and Stroke: Therapeutic Effects of Adenoviral Expression of Secretory Leukocyte Protease Inhibitor." Front. Biosci., 2006, 11, 1750-1757.

Forteza et al. "Secretory Leukocyte Protease Inhibitor, but not α-1 Protease Inhibitor, Blocks Tryptase-Induced Bronchoconstriction." Pulm. Pharmacol. Ther., 2001, 14, 107-110.

Gura, "Systems for Identifying New Drugs Are Often Faulty," Science, Nov. 1997, 278(5340), 1041-1042.

Gast et al. "Pharmacokinetics and Distribution of Recombinant Secretory Leukocyte Proteinase Inhibitor in Rats." Am. Rev. Respir. Dis., 1990, 141, 889-894.

GenBank Accession No. AAA51546.1, Oct. 30, 1994.
GenBank Accession No. AAA51547.1, Oct. 30, 1994.
GenBank Accession No. AAB59375.1, Nov. 1, 1994.
GenBank Accession No. AAB59495.1, Aug. 8, 1995.
GenBank Accession No. ABV21360, May 20, 2010.
GenBank Accession No. AAD19661.1, May 30, 2002.

(56) References Cited

OTHER PUBLICATIONS

GenBank Accession No. AAG00546.1, Jun. 14, 2001.
GenBank Accession No. AAG00547.1, Jun. 14, 2001.
GenBank Accession No. AAG00548.1, Jun. 14, 2001.
GenBank Accession No. AAH20708.1, Jul. 15, 2006.
GenBank Accession No. AAH44829.2, Mar. 9, 2007.
GenBank Accession No. AAH53369.1, Jul. 15, 2006.
GenBank Accession No. BAA02441.1, Jul. 21, 2005.
GenBank Accession No. BAG35125.1, May 24, 2008.
GenBank Accession No. CAA25838.1, Mar. 5, 2002.
GenBank Accession No. CAA28187.1, Apr. 18, 2005.
GenBank Accession No. CAA28188.1, Oct. 7, 2008.
GenBank Accession No. CAA34982.1, Apr. 18, 2005.
GenBank Accession No. CAB64235.1, Jan. 13, 2009.
GenBank Accession No. CAJ15161.1, Jul. 8, 2007.
GenBank Accession No. EAW75813.1, Feb. 4, 2010.
GenBank Accession No. EAW75814.1, Feb. 4, 2010.
GenBank Accession No. EAW75869.1, Feb. 4, 2010.
GenBank Accession No. MHHU GI:7428607, Jun. 22, 1999.
GenBank Accession No. NP_000286.3, Jun. 27, 2012.
GenBank Accession No. NP_001002235.1, Jun. 27, 2012.
GenBank Accession No. NP_001002236.1, Jun. 27, 2012.
GenBank Accession No. NP_001121172, Jun. 27, 2012.
GenBank Accession No. NP_001121174.1, Jun. 27, 2012.
GenBank Accession No. NP_001121175.1, Jun. 27, 2012.
GenBank Accession No. NP_001121176.1, Jun. 27, 2012.
GenBank Accession No. NP_001121177.1, Jun. 27, 2012.
GenBank Accession No. NP_001121178.1, Jun. 27, 2012.
GenBank Accession No. NP_001121179.1, Jun. 27, 2012.
GenBank Accession No. NP_002629.1, Jun. 27, 2012.
GenBank Accession No. NP_003055.1, Jun. 27, 2012.
GenBank Accession No. NP_065131.1, Apr. 29, 2012.
GenBank Accession No. NP_542181.1, Mar. 25, 2012.
GenBank Accession No. 095925.1, Jun. 13, 2012.
GenBank Accession No. P01009.3, Jun. 13, 2012.
GenBank Accession No. P03973.2, Jun. 13, 2012.
GenBank Accession No. P19957.3, Jun. 13, 2012.
GenBank Accession No. Q8IUB2.1, Jun. 13, 2012.
Genbank Accession No. ABV21606.1, secretory leukocyte peptidase inhibitor precursor [synthetic construct], Munadziroh, E. et al., Sep. 16, 2007.
Genbank Accession No. CAA04844.1, immunoglobulin heavy chain, constant region, partial [*Homo sapiens*], Ellison, J., et al., Nov. 14, 2006.
GenBank: Accession No. ACD12527 "A1AT [Plastid transformation vector pAPR23]." [retrieved online Jun. 28, 2017 at https://www.ncbi.nlm.nih.gov/protein/187476087/].
Ghasemlou et al. "Beneficial Effects of Secretory Leukocyte Protease Inhibitor After Spinal Cord Injury." Brain., 2010, 133, 126-138.
Gomez et al.: "Secretory Leukocyte Protease Inhibitor—A Secreted Pattern Recognition Receptor for Mycobacteria" American Journal of Respiratory Critical Care Medicine, Nov. 14, 2008, 179, 247-253.
Gonzalez R. et al.: "Screening the mammalian extracellular proteome for regulators of embryonic human stem cell pluripotency", Proceedings of the National Academy of Sciences, Feb. 2, 2010, 107(8), 3552-3557.
Greene C. et al. "Proteases and antiproteases in chronic neutrophilic lung disease—relevance to drug discovery", British Journal of Pharmacology, 2009, 158, 1048-1058.
Grütter et al. "The 2.5 Å X-ray crystal structure of the acid stable proteinase inhibitor from human mucous secretions analysed in its complex with bovine a-chymotrypsin" The EMBO Journal, 1988, 7(2), 345-351.
Hamaker et al. "Chromatography for Rapid Buffer Exchange and Refolding of Secretory Leukocyte Protease Inhibitor." Biotechnol. Prog., 1996, 12, 184-189.
Hogenesch et al. "Challenges in pre-clinical testing of anti-cancer drugs in cell culture and in animal models," J Control Release, Dec. 10, 2012, 164(2), 183-186.

Hiemstra et al. "Antibacterial Activity of Antileukoprotease." Infect. Immun., 1996, 64(11), 4520-4524.
Hocini et al. "Secretory Leukocyte Protease Inhibitor Inhibits Infection of Monocytes and Lymphocytes with Human Immunodeficiency Virus Type 1 but Does Not Interfere with Transcytosis of Cell-Associated Virus Across Tight Epithelial Barriers." Clin. Diagn. Immunol., 2000, 7(3), 515-518.
Huang. "Receptor-Fc Fusion Therapeutics, Traps, and Mimetibody™ Technology." Curr. Opin. Biotechnol., 2009, 20, 692-699.
Ilmakunnas et al.: "Endogenous protease inhibitor uptake within the graft during reperfusion in human liver transplantation" Journal of Hepatobiliary and Pancreatic Sciences, May 19, 2010, 17, 158-165.
Instructions—Gentle Ag/Ab Binding and Elution Buffers (ThermoFisher Scientific. 2011. Last accessed at tools.thermofisher.com/content/sfs/manuals/MAN0011176_Gentle_AgAb_Bind_Elution_Buff_UG.pdf on Nov. 18, 2016).
Jain, "Barriers to Drug Delivery in Solid Tumors," Scientific American, Jul. 1994, 58-65.
Janciauskiene et al. "α1-Antitrypsin, Old Dog, New Tricks: α1-Antitrypsin Exerts in vitro Anti-Inflammatory Activity in Human Monocytes by Elevating cAMP." J. Biol. Chem., 2007, 282(12), 8573-8582.
Janciauskiene et al.: "The discovery of a1-antitrypsin and its role in health and disease" Respiratory Medicine., 2011, 105, 1129-1139.
Jazayeri et al. "Fc-Based Cytokines: Prospects for Engineering Superior Therapeutics." BioDrugs. 2008, 22(1), 11-26.
Jin et al. "Lipopolysaccharide-Related Stimuli Induce Expression of the Secretory Leukocyte Protease Inhibitor, a Macrophage-Derived Lipopolysaccharide Inhibitor." Infect. Immun. 1998, 66(6), 2447-2452.
Kabat et al. Sequences of Proteins of Immunological Interest, 5th edit. NIH Publication No. 91-3242 U.S. Dept of Health & Human Services (1991): iii-xcvi, 2130-2180.
Kalis et al. "α 1-Antitrypsin Enhances Insulin Secretion and Prevents Cytokine-Mediated Apoptosis in Pancreatic β-Cells." Islets., 2010, 2(3), 185-189.
Kalsheker, "Alpha 1-Antitrypsin: Structure, Function and Molecular Biology of the Gene," Bioscience Reports, 1989, 9, 129-138.
Karnaukhova et al. "Recombinant Human α-1 Proteinase Inhibitor: Towards Therapeutic Use." Amino Acids., 2006, 30(4), 317-332.
King et al. "Innate Immune Defences in the Human Endometrium." Reproductive Biology and Endocrinol., 2003, 1(116), 1-8.
Kontermann. "Strategies to Extend Plasma Half-Lives of Recombinant Antibodies." BioDrugs. 2009, 23(2), 93-109.
Lee et al. "Effect of Recombinant alpha 1-Antitrypsin Fe-Fused (AAT-Fc) Protein on the Inhibition of Inflammatory Cytokine Production and Streptozotocin-Induced Diabetes," Molecular Medicine., 2013, (19)1, 65-71.
Lentsch et al. "Inhibition of NF-κB Activation and Augmentation of IKBβ by Secretory Leukocyte Protease Inhibitor During Lung Inflammation." Am. J. Pathol, 1999, 154(1), 239-247.
Lewis et al. "α1-Antitrypsin Monotherapy Induces Immune Tolerance During Islet Allograft Transplantation in Mice." PNAS, 2008, 105(42), 16236-16241.
Lewis et al. "α1-Antitrypsin Monotherapy Prolongs Islet Allograft Survival in Mice." PNAS, 2005, 102(34), 12153-12158.
Li et al. "Expression and Characterization of Recombinant Human Secretory Leukocyte Protease Inhibitor (SLPI) Protein from Pichia pastoris." Protein Exp. Purif., 2009, 67, 175-181.
Libert et al. "α1-Antitrypsin Inhibits the Lethal Response to TNF in Mice." J. Immunol., 1996, 157, 5126-5129.
Lucey et al. "Recombinant Human Secretory Leukocyte-Protease Inhibitor: In Vitro Properties, and Amelioration of Human Neutrophil Elastase-Induced Emphysema and Secretory Cell Metaplasia in the Hamster." J. Lab. Clin. Med., 1990, 115, 224-232.
Lungarella et al. "The Dual Role of Neutrophil Elastase in Lung Destruction and Repair." Int. J. Biochem. Cell Biol., 2008, 40(6-7), 1287-1296.
Liu, et al. "A mechanistic study of Protein A chromatography resin lifetime." Journal of chromatography. A, Jun. 9, 2009, 1216(31), 5849-5855.

(56) References Cited

OTHER PUBLICATIONS

Ma, "Animal models of disease, these systems are becoming increasingly important secondary screens of in vitro hits," Modern Drug Discovery, 2004, 7(6), 30-36.
Marasco et al. "Design, Intracellular Expression, and Activity of a Human Anti-Human Immunodeficiency Virus Type 1 jp120 Single-Chain Antibody." PNAS., 1993, 90(16), 7889-7893.
Marcondes et al. "Inhibition of IL-32 Activation by α-1 Antitrypsin Suppresses Alloreactivity and Increases Survival in an Allogeneic Murine Marrow Transplantation Model." Blood, 2011, 118(18), 5031-5039.
Marino et al. "Secretory Leukocyte Protease Inhibitor Plays an Important Role in the Regulation of Allergic Asthma in Mice." J. Immunol., 2011, 186, 4433-4442.
Maruyama et al. "Modulation of Secretory Leukoprotease Inhibitor Gene Expression in Human Bronchial Epithelial Cells by Phorbol Ester." J. Clin. Invest., 1994, 94(1), 368-375.
Masuda et al. "Role of Fc Receptors as a Therapeutic Target" Inflammation & Allergy—Drug Targets., 2009, 8, 80-86.
McElvaney N.G. et al., "Pharmacokinetics of Recombinant Secretory Leukoprotease Inhibitor Aerosolized to Normals and Individuals with Cystic Fibrosis." Am. Rev. Respir. Dis., Oct. 31, 1993, 148(4 Pt 1), 1056-1060.
McMichael et al. "The Antimicrobial Antiproteinase Elafin Binds to Lipopolysaccharide and Modulates Macrophage Responses." Am. J. Respir. Cell Mol. Biol., 2005, 32, 443-452.
McNeely et al. "Inhibition of Human Immunodeficiency Virus Type 1 Infectivity by Secretory Leukocyte Protease Inhibitor Occurs Prior to Viral Reverse Transcription." Blood, 1997, 90(3), 1141-1149.
McNeely et al. "Secretory Leukocyte Protease Inhibitor: A Human Saliva Protein Exhibiting Anti-Human Immunodeficiency Virus 1 Activity In Vitro." J. Clin. Invest., 1995, 96(1), 456-464.
Meyer-Hoffert et al. "Supernatants of Pseudomonas aeruginosa Induce the Pseudomonas-Specific Antibiotic Elafin in Human Keratinocytes." Exp. Dermatol., 2003, 12(4), 418-425.
Michaelson et al. "Anti-tumor activity of stability-engineered IgG-like bispecific antibodies targeting TRAIL-R2 and LTβR" MAbs., 2009, 1, 128-141.
Mulligan et al. "Anti-Inflammatory Effects of Mutant Forms of Secretory Leukocyte Protease Inhibitor." Am. J. Pathol., 2000, 156(3), 1033-1039.
Nakamura et al. "Increased Susceptibility to LBS-Induced Endotoxin Shock in Secretory Leukoprotease Inhibitor (SLPI)-Deficient Mice." J. Exp. Med., 2003, 197(5), 669-674.
Nishimura et al. "Potent Antimycobacterial Activity of Mouse Secretory Leukocyte Protease Inhibitor." J. Immunol., 2008, 180, 4032-4039.
Nita et al. "α1-Antitrypsin Regulates CD14 Expression and Soluble CD14 Levels in Human Monocytes in vitro." Int. J. Biochem. Cell Biol., 2007, 39(6), 1165-1176.
Nocentini, G. et al. "Glucocorticoid-Induced Tumor Necrosis Factor Receptor-Related (GITR)-Fc Fusion Protein Inhibits GITR Triggering and Protects from the Inflammatory Response after Spinal Cord Injury", Mol. Pharmacol., 2008, 73, 1610-1621.
Notice of Reasons for Rejection (Translation) issued for Japanese Application No. JP2014-519054, dated Dec. 13, 2016.
Nukiwa et al. "Secretory leukocyte peptidase inhibitor and lung cancer" Cancer Science, Mar. 28, 2008, 99(5), 849-855.
Ohbayashi, "Current Synthetic Inhibitors of Human Neutrophil Elastase in 2005," Expert Opin. Ther. Patents, 2005, 15, 759-771.
Pillay et al. "Secretory Leukocyte Protease Inhibitor in Vaginal Fluids and Perinatal Human Immunodeficiency Virus Type 1 Transmission." J. Infect. Dis., 2001, 183(4), 653-656.
Pott et al. "α-1-Antitrypsin is an Endogenous Inhibitor of Proinflammatory Cytokine Production in Whole Blood." J. Leukoc. Biol., 2009, 85, 886-895.
Powell et al. "Compendium of Excipients for Parental Formulations." PDA J. Pharm. Sci. Technol., 1998, 52, 238-311.

Quinn, D. et al. "Antiproteases as Therapeutics to Target Inflammation in Cystic Fibrosis", The Open Respiratory Medicine Journal, 2010, 4, 20-31.
Rabinovitch. "Eve and Beyond, Retro and Prospective Insights." Am. J. Physiol. Lung Cell. Mol. Physiol., 1999, 277, L5-L12.
Ranganathan et al. "The Whey Acid Protein Family: A New Signature Motif and Three-Dimensional Structure by Comparative Modeling." J. Mol. Graphics Modell., 1999, 17(2), 106-113.
Rao et al. "Interaction of Secretory Leukocyte Protease Inhibitor with Proteinase-3." Am. J. Respir. Cell Mol. Biol., 1993, 8, 612-616.
Sallenave et al. "Regulation of Pulmonary and Systemic Bacterial Lipopolysaccharide Responses in Transgenic Mice Expressing Human Elafin." Infect. Immun., 2003, 71(7), 3766-3774.
Sallenave. "Secretory Leukocyte Protease Inhibitor and Elafin/Trappin-2: versatile mucosal antimicrobials and regulators of immunity." Am. J. Respir. Cell Mol. Biol., 2010, 42, 635-643.
Schalkwijk et al. "The Trappin Gene Family: Proteins Defined by an N-Terminal Transglutaminase Substrate Domain and a C-Terminal Four-Disulphide Core." Biochem. J. 1999, 340, 569-577.
Schmidt. "Fusions-Proteins as Biopharmaceuticals: Applications and Challenges." Curr. Opin. Drug Disc. Dev., 2009, 12(2), 284-295.
Schneeberger et al. "The Effect of Secretory Leukocyte Protease Inhibitor (SLPI) on Ischemia/Reperfusion Injury in Cardiac Transplantation." Am. J. Transplant., 2008, 8, 773-782.
Scott et al. "SLPI and Elafin: Multifunctional Antiproteases of the WFDC Family." Biochem. Soc. Trans., 2011, 39(5), 1437-1440.
Scott et al.: "Comparison of IgA-α1-Antitrypsin Levels in Rheumatoid Arthritis and Seronegative Oligoarthritis: Complex Formation is not Associated with Inflammation per SE." British Journal of Rheumatology, 1998, 37, 398-404.
Shaw et al. "Therapeutic Potential of Human Elafin." Biochem. Soc. Trans., 2011, 39(5), 1450-1454.
Sheffield et al.: "Addition of a sequence from [alpha]-2-antiplasmin transforms human serum albumin into a blood clot component that speeds clot lysis", BMC Biotechnology, Mar. 3, 2009, 9(1), p. 15.
Simpson et al. "Elafin (Elastase-Specific Inhibitor) has Anti-Microbial Activity Against Gram-Positive and Gram-Negative Respiratory Pathogens." FEBS Lett., 1999, 452(3), 309-313.
Simpson et al. "Regulation of Adenovirus-Mediated Elafin Transgene Expression by Bacterial Lipopolysaccharide." Hum. Gene Ther., 2001, 12, 1395-1406.
Si-Tahar et al. "Constitutive and Regulated Secretion of Secretory Leukocyte Proteinase Inhibitor by Human Intestinal Epithelial Cells." Gastroenterology., 2000, 118(6), 1061-1071.
Steinman et al. "Optimization of current and future therapy for autoimmune diseases," Nat Med. Jan. 2012, 18(1), 59-65.
Song et al. "Secretory Leukocyte Protease Inhibitor Suppresses the Inflammation and Joint Damage of Bacterial Cell Wall-Induced Arthritis." J. Exp. Med., 1999, 190(4), 535-542.
Stolk et al. "Lipopolysaccharide-Induced Alveolar Wall Destruction in the Hamster is Inhibited by Intratracheal Treatment With r-Secretory Leukocyte Protease Inhibitor." Ann. N.Y. Acad. Sci., 1991, 624, 350-352.
Stromatt. "Secretory Leukocyte Protease Inhibitor in Cystic Fibrosis." Agents Actions Suppl., 1993, 42, 103-110.
Subramanian et al. "Sustained Expression of Circulating Human α-1 Antitrypsin Reduces Inflammation, Increases CD4+FoxP3+ Treg Cell Population and Prevents Signs of Experimental Autoimmune Encephalomyelitis in Mice." Metab. Brain Dis., 2011, 26(2), 107-113.
Sporn et al. "Chemoprevention of Cancer," Carcinogenesis, 2000, 21(3), 525-530.
Taggart et al. "Secretory Leucoprotease Inhibitor Binds to NK-KB Binding Sites in Monocytes and Inhibits p65 Binding." J. Exp. Med., 2005, 202(12), 1659-1668.
Taggart et al.: "Oxidation of either Methionine 351 or Methionine 358 in a1-Antitrypsin Causes Loss of Anti-neutrophil Elastase Activity". J. Biol. Chem., 2000, 275, 27258-27265.
Tarawa et al. "α-1-Antitrypsin Monotherapy Reduces Graft-Versus-Host Disease After Experimental Allogeneic Bone Marrow Transplantation." PNAS., 2012 109(2), 564-569.
Therapeutic Research, 1998, 19(10), 204-208.

(56) References Cited

OTHER PUBLICATIONS

Tilg et al. "Anti-inflammatory Properties of Hepatic Acute Phase Proteins: Preferential Induction of Interleukin 1 (IL-1) Receptor Antagonist Over IL-1β Synthesis by Human Peripheral Blood Mononuclear Cells." J. Exp. Med., 1993, 178, 1629-1636.
Tomee et al. "Antileukoprotease: An Endogenous Protein in the Innate Mucosal Defense Against Fungi." J. Infect. Dis., 1997, 176(3), 740-747.
TR0027-Elution-Conditions (ThermoFisher Scientific Inc., Tech Tip#27 "Optimize elution conditions for immunoaffinity purification." 2009. Last accessed at tools.thermofisher.com/.../TR0027-Elution-conditions.pdf on Nov. 18, 2016).
UniProtKB/Swiss-Pro P01861 (IGHG4_HUMAN), Jul. 21, 1986.
Wang et al. "Up-Regulation of Secretory Leukocyte Protease Inhibitor (SLPI) in the Brain After Ischemic Stroke: Adenoviral Expression of SLPI Protects Brain from Ischemic Injury." Mol. Pharmacol., 2003, 64(4), 833-840.
Wang. "Lyophilization and Development of Solid Protein Pharmaceuticals." Int. J. Pharm., 2000, 203(1-2), 1-60.
Watterberg et al. "Secretory Leukocyte Protease Inhibitor and Lung Inflammation in Developing Bronchopulmonary Dysplasia." J. Pediatr., 1994, 125, 264-269.
Weldon et al. "The Role of Secretory Leucoprotease Inhibitor in the Resolution of Inflammatory Responses." Biochem. Soc. Trans., 2007, 35, 273-276.
Wiedow et al. "Antileukoprotease in Human Skin: An Antibiotic Peptide Constitutively Produced by Keratinocytes." Biochem. Biophys. Res. Commun., 1998, 248(3), 904-909.
Williams et al. "SLPI and Elafin: One Glove, Many Fingers." Clin. Sci., 2006, 110(1), 21-35.
Wright et al. "Secretory Leukocyte Protease Inhibitor Prevents Allergen-Induced Pulmonary Responses in Animal Models of Asthma." J. Pharmacol. Exp. Ther., 1999, 289(2), 1007-1014.
Ying et al. "Kinetics of the Inhibition of Proteinase 3 by Elafin." Am. J. Respir. Cell Mol. Biol., 2001, 24, 83-89.
Ying et al. "Soluble Monomeric IgG1 Fc." J. Biol. Chem., 2012, 287(23), 19399-19408.
Zalevsky et al. "Enhanced antibody half-life improves in vivo activity", Nature Biotechnology, 2010, 28(2), 157-159.
Zhang et al. "α1-Antitrypsin Protects B-Cells from Apoptosis." Diabetes., 2007, 56, 1316-1323.
GenBank Accession No. P01861.1, Aug. 12, 2020, 5 pages.
Gonzalez et al., "Supporting Information," retrieved from www.pnas.org/cgi/content/short/0914019107, PNAS, Feb. 23, 2010, 4 pages.
Graslund, et al. "Protein production and purification." Nat Methods. Feb. 2008, 5(2):135-146 (25 pages total).
Lazar, E. et al., "Transforming Growth Factor α: Mutation of Aspartic Acid 47 and Leucine 48 Results in Different Biological Activities," Molecular and Cellular Biology, Mar. 1988, 8(3):1247-1252.
Pina, et al. "Challenges and opportunities in the purification of recombinant tagged proteins." Biotechnol Adv. Mar.-Apr. 2014, 32(2):366-381.
Colman, P.M. et al. "Effects of amino acid sequence changes on antibody-antigen interactions", Research in Immunology, 1994, vol. 145, Issue 1, pp. 33-36.
Nezlin, R. "General Characteristics of Immunoglobulin Molecules", The Immunoglobulins, 1998, pp. 3-73. doi:10.1016/b978-012517970-6 /50001-1.
Sampei, Z. et al. "Nonantigen-contacting region of an asymmetric bispecific antibody to factors IXa/X significantly affects factor VIII-mimetic activity", MAbs, 2015, vol. 7, Issue 1, pp. 120-128. doi: 10.4161/19420862.2015.989028.
Torres, M. et al. "The immunoglobulin constant region contributes to affinity and specificity", Trends Immunol., 2008, vol. 29, Issue 2, pp. 91-97. doi:10.1016/j.it.2007.11.004.
Congote, F.L. et al., "Comparison of the effects of serpin A1, a recombinant serpin A1-IGF chimera and serpin A1 C-terminal peptide on wound healing", Peptides, Jan. 2008, vol. 29(1), pp. 39-46.

\* cited by examiner 1. sdAAT
2. AAT-Fc
3. AAT-EL-Fc

1. AAT-hFc-Elafin
2. AAT-hFc-SLPI

NE activity assay

SEQUENCE LISTING

```
<160> NUMBER OF SEQ ID NOS: 46

<210> SEQ ID NO 1
<211> LENGTH: 25
<212> TYPE: PRT
<213> ORGANISM: Artificial Sequence
<220> FEATURE:
<223> OTHER INFORMATION: reactive site loop portion of the alpha-1
      antitrypsin (AAT) protein

<400> SEQUENCE: 1
```

Gly Thr Glu Ala Ala Gly Ala Met Phe Leu Glu Ala Ile Pro Met Ser
1               5                   10                  15

Ile Pro Pro Glu Val Lys Phe Asn Lys
                20                  25

<210> SEQ ID NO 2
<211> LENGTH: 394
<212> TYPE: PRT
<213> ORGANISM: Homo sapiens

<400> SEQUENCE: 2

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
                20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe

```
            340                 345                 350
Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
        370                 375                 380

Met Gly Lys Val Val Asn Pro Thr Gln Lys
385                 390

<210> SEQ ID NO 3
<211> LENGTH: 217
<212> TYPE: PRT
<213> ORGANISM: Homo sapiens

<400> SEQUENCE: 3

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 4
<211> LENGTH: 216
<212> TYPE: PRT
<213> ORGANISM: Homo sapiens

<400> SEQUENCE: 4

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
```

```
            50                  55                  60
Phe Asn Ser Thr Phe Arg Val Val Ser Val Leu Thr Val His Gln
 65                  70                  75                  80

Asp Trp Leu Asn Gly Lys Glu Tyr Lys Cys Lys Val Ser Asn Lys Gly
                 85                  90                  95

Leu Pro Ala Pro Ile Glu Lys Thr Ile Ser Lys Thr Lys Gly Gln Pro
                100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 5
<211> LENGTH: 217
<212> TYPE: PRT
<213> ORGANISM: Homo sapiens

<400> SEQUENCE: 5

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205
```

```
Lys Ser Leu Ser Leu Ser Pro Gly Lys
    210                 215
```

<210> SEQ ID NO 6
<211> LENGTH: 216
<212> TYPE: PRT
<213> ORGANISM: Homo sapiens

<400> SEQUENCE: 6

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Arg Leu Thr Val Asp Lys Ser Arg Trp Gln Glu Gly Asn Val Phe
            180                 185                 190

Ser Cys Ser Val Met His Glu Ala Leu His Asn His Tyr Thr Gln Lys
        195                 200                 205

Ser Leu Ser Leu Ser Leu Gly Lys
    210                 215
```

<210> SEQ ID NO 7
<211> LENGTH: 218
<212> TYPE: PRT
<213> ORGANISM: Homo sapiens

<400> SEQUENCE: 7

```
Ile Ala Glu Leu Pro Pro Lys Val Ser Val Phe Val Pro Pro Arg Asp
1               5                   10                  15

Gly Phe Phe Gly Asn Pro Arg Lys Ser Lys Leu Ile Cys Gln Ala Thr
            20                  25                  30

Gly Phe Ser Pro Arg Gln Ile Gln Val Ser Trp Leu Arg Glu Gly Lys
        35                  40                  45

Gln Val Gly Ser Gly Val Thr Thr Asp Gln Val Gln Ala Glu Ala Lys
    50                  55                  60

Glu Ser Gly Pro Thr Thr Tyr Lys Val Thr Ser Thr Leu Thr Ile Lys
65                  70                  75                  80

Glu Ser Asp Trp Leu Gly Gln Ser Met Phe Thr Cys Arg Val Asp His
                85                  90                  95
```

```
Arg Gly Leu Thr Phe Gln Gln Asn Ala Ser Ser Met Cys Val Pro Asp
                100                 105                 110

Gln Asp Thr Ala Ile Arg Val Phe Ala Ile Pro Pro Ser Phe Ala Ser
            115                 120                 125

Ile Phe Leu Thr Lys Ser Thr Lys Leu Thr Cys Leu Val Thr Asp Leu
        130                 135                 140

Thr Thr Tyr Asp Ser Val Thr Ile Ser Trp Thr Arg Gln Asn Gly Glu
145                 150                 155                 160

Ala Val Lys Thr His Thr Asn Ile Ser Glu Ser His Pro Asn Ala Thr
                165                 170                 175

Phe Ser Ala Val Gly Glu Ala Ser Ile Cys Glu Asp Asp Trp Asn Ser
            180                 185                 190

Gly Glu Arg Phe Thr Cys Thr Val Thr His Thr Asp Leu Pro Ser Pro
        195                 200                 205

Leu Lys Gln Thr Ile Ser Arg Pro Lys Gly
        210                 215

<210> SEQ ID NO 8
<211> LENGTH: 132
<212> TYPE: PRT
<213> ORGANISM: Homo sapiens

<400> SEQUENCE: 8

Met Lys Ser Ser Gly Leu Phe Pro Phe Leu Val Leu Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                85                  90                  95

Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
        115                 120                 125

Pro Val Lys Ala
    130

<210> SEQ ID NO 9
<211> LENGTH: 107
<212> TYPE: PRT
<213> ORGANISM: Homo sapiens

<400> SEQUENCE: 9

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
    50                  55                  60
```

```
Pro Val Thr Tyr Gly Gln Cys Leu Met Leu Asn Pro Pro Asn Phe Cys
 65                  70                  75                  80

Glu Met Asp Gly Gln Cys Lys Arg Asp Leu Lys Cys Cys Met Gly Met
                 85                  90                  95

Cys Gly Lys Ser Cys Val Ser Pro Val Lys Ala
            100                 105
```

<210> SEQ ID NO 10
<211> LENGTH: 51
<212> TYPE: PRT
<213> ORGANISM: Homo sapiens

<400> SEQUENCE: 10

```
Thr Arg Arg Lys Pro Gly Lys Cys Pro Val Thr Tyr Gly Gln Cys Leu
1               5                  10                  15

Met Leu Asn Pro Pro Asn Phe Cys Glu Met Asp Gly Gln Cys Lys Arg
             20                  25                  30

Asp Leu Lys Cys Cys Met Gly Met Cys Gly Lys Ser Cys Val Ser Pro
         35                  40                  45

Val Lys Ala
     50
```

<210> SEQ ID NO 11
<211> LENGTH: 117
<212> TYPE: PRT
<213> ORGANISM: Homo sapiens

<400> SEQUENCE: 11

```
Met Arg Ala Ser Ser Phe Leu Ile Val Val Phe Leu Ile Ala Gly
1               5                  10                  15

Thr Leu Val Leu Glu Ala Ala Val Thr Gly Val Pro Val Lys Gly Gln
             20                  25                  30

Asp Thr Val Lys Gly Arg Val Pro Phe Asn Gly Gln Asp Pro Val Lys
         35                  40                  45

Gly Gln Val Ser Val Lys Gly Gln Asp Lys Val Lys Ala Gln Glu Pro
     50                  55                  60

Val Lys Gly Pro Val Ser Thr Lys Pro Gly Ser Cys Pro Ile Ile Leu
 65                  70                  75                  80

Ile Arg Cys Ala Met Leu Asn Pro Pro Asn Arg Cys Leu Lys Asp Thr
                 85                  90                  95

Asp Cys Pro Gly Ile Lys Lys Cys Cys Glu Gly Ser Cys Gly Met Ala
            100                 105                 110

Cys Phe Val Pro Gln
            115
```

<210> SEQ ID NO 12
<211> LENGTH: 95
<212> TYPE: PRT
<213> ORGANISM: Homo sapiens

<400> SEQUENCE: 12

```
Ala Val Thr Gly Val Pro Val Lys Gly Gln Asp Thr Val Lys Gly Arg
1               5                  10                  15

Val Pro Phe Asn Gly Gln Asp Pro Val Lys Gly Gln Val Ser Val Lys
             20                  25                  30

Gly Gln Asp Lys Val Lys Ala Gln Glu Pro Val Lys Gly Pro Val Ser
         35                  40                  45

Thr Lys Pro Gly Ser Cys Pro Ile Ile Leu Ile Arg Cys Ala Met Leu
```

```
                  50                  55                  60

Asn Pro Pro Asn Arg Cys Leu Lys Asp Thr Asp Cys Pro Gly Ile Lys
 65                  70                  75                  80

Lys Cys Cys Glu Gly Ser Cys Gly Met Ala Cys Phe Val Pro Gln
                 85                  90                  95

<210> SEQ ID NO 13
<211> LENGTH: 49
<212> TYPE: PRT
<213> ORGANISM: Homo sapiens

<400> SEQUENCE: 13

Val Ser Thr Lys Pro Gly Ser Cys Pro Ile Ile Leu Ile Arg Cys Ala
  1               5                  10                  15

Met Leu Asn Pro Pro Asn Arg Cys Leu Lys Asp Thr Asp Cys Pro Gly
                 20                  25                  30

Ile Lys Lys Cys Cys Glu Gly Ser Cys Gly Met Ala Cys Phe Val Pro
                 35                  40                  45

Gln

<210> SEQ ID NO 14
<211> LENGTH: 585
<212> TYPE: PRT
<213> ORGANISM: Homo sapiens

<400> SEQUENCE: 14

Asp Ala His Lys Ser Glu Val Ala His Arg Phe Lys Asp Leu Gly Glu
  1               5                  10                  15

Glu Asn Phe Lys Ala Leu Val Leu Ile Ala Phe Ala Gln Tyr Leu Gln
                 20                  25                  30

Gln Cys Pro Phe Glu Asp His Val Lys Leu Val Asn Glu Val Thr Glu
                 35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
                115                 120                 125

Asp Asn Glu Glu Thr Phe Leu Lys Lys Tyr Leu Tyr Glu Ile Ala Arg
                130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
                210                 215                 220

Lys Ala Glu Phe Ala Glu Val Ser Lys Leu Val Thr Asp Leu Thr Lys
225                 230                 235                 240
```

```
Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 15
<211> LENGTH: 196
<212> TYPE: PRT
<213> ORGANISM: Homo sapiens

<400> SEQUENCE: 15

Glu Glu Pro Gln Asn Leu Ile Lys Gln Asn Cys Glu Leu Phe Glu Gln
1               5                   10                  15

Leu Gly Glu Tyr Lys Phe Gln Asn Ala Leu Leu Val Arg Tyr Thr Lys
```

```
            20                  25                  30
Lys Val Pro Gln Val Ser Thr Pro Thr Leu Val Glu Val Ser Arg Asn
            35                  40                  45

Leu Gly Lys Val Gly Ser Lys Cys Cys Lys His Pro Glu Ala Lys Arg
            50                  55                  60

Met Pro Cys Ala Glu Asp Tyr Leu Ser Val Val Leu Asn Gln Leu Cys
 65                  70                  75                  80

Val Leu His Glu Lys Thr Pro Val Ser Asp Arg Val Thr Lys Cys Cys
                85                  90                  95

Thr Glu Ser Leu Val Asn Arg Arg Pro Cys Phe Ser Ala Leu Glu Val
            100                 105                 110

Asp Glu Thr Tyr Val Pro Lys Glu Phe Asn Ala Glu Thr Phe Thr Phe
            115                 120                 125

His Ala Asp Ile Cys Thr Leu Ser Glu Lys Glu Arg Gln Ile Lys Lys
            130                 135                 140

Gln Thr Ala Leu Val Glu Leu Val Lys His Lys Pro Lys Ala Thr Lys
145                 150                 155                 160

Glu Gln Leu Lys Ala Val Met Asp Asp Phe Ala Ala Phe Val Glu Lys
                165                 170                 175

Cys Cys Lys Ala Asp Asp Lys Glu Thr Cys Phe Ala Glu Glu Gly Lys
            180                 185                 190

Lys Leu Val Ala
            195
```

<210> SEQ ID NO 16
<211> LENGTH: 626
<212> TYPE: PRT
<213> ORGANISM: Artificial Sequence
<220> FEATURE:
<223> OTHER INFORMATION: AAT-hFc1 fusion protein

<400> SEQUENCE: 16

```
Glu Asp Pro Gln Gly Asp Ala Ala Gln Lys Thr Asp Thr Ser His His
 1                   5                  10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
            50                  55                  60

Ser Leu Gly Thr Lys Ala Asp Thr His Asp Glu Ile Leu Glu Gly Leu
 65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
            115                 120                 125

Lys Phe Leu Glu Asp Val Lys Lys Leu Tyr His Ser Glu Ala Phe Thr
            130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
```

```
                180                 185                 190
Lys Trp Glu Arg Pro Phe Glu Val Lys Asp Thr Glu Glu Asp Phe
                195                 200                 205

His Val Asp Gln Val Thr Thr Val Lys Val Pro Met Met Lys Arg Leu
                210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
                260                 265                 270

Thr Lys Phe Leu Glu Asn Glu Asp Arg Arg Ser Ala Ser Leu His Leu
                275                 280                 285

Pro Lys Leu Ser Ile Thr Gly Thr Tyr Asp Leu Lys Ser Val Leu Gly
                290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
                340                 345                 350

Leu Glu Ala Ile Pro Met Ser Ile Pro Pro Glu Val Lys Phe Asn Lys
                355                 360                 365

Pro Phe Val Phe Leu Met Ile Glu Gln Asn Thr Lys Ser Pro Leu Phe
                370                 375                 380

Met Gly Lys Val Val Asn Pro Thr Gln Lys Glu Pro Lys Ser Cys Asp
385                 390                 395                 400

Lys Thr His Thr Cys Pro Pro Cys Pro Ala Pro Glu Leu Leu Gly Gly
                405                 410                 415

Pro Ser Val Phe Leu Phe Pro Pro Lys Pro Lys Asp Thr Leu Met Ile
                420                 425                 430

Ser Arg Thr Pro Glu Val Thr Cys Val Val Val Asp Val Ser His Glu
                435                 440                 445

Asp Pro Glu Val Lys Phe Asn Trp Tyr Val Asp Gly Val Glu Val His
                450                 455                 460

Asn Ala Lys Thr Lys Pro Arg Glu Glu Gln Tyr Asn Ser Thr Tyr Arg
465                 470                 475                 480

Val Val Ser Val Leu Thr Val Leu His Gln Asp Trp Leu Asn Gly Lys
                485                 490                 495

Glu Tyr Lys Cys Lys Val Ser Asn Lys Ala Leu Pro Ala Pro Ile Glu
                500                 505                 510

Lys Thr Ile Ser Lys Ala Lys Gly Gln Pro Arg Glu Pro Gln Val Tyr
                515                 520                 525

Thr Leu Pro Pro Ser Arg Asp Glu Leu Thr Lys Asn Gln Val Ser Leu
                530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
                565                 570                 575

Leu Asp Ser Asp Gly Ser Phe Phe Leu Tyr Ser Lys Leu Thr Val Asp
                580                 585                 590

Lys Ser Arg Trp Gln Gln Gly Asn Val Phe Ser Cys Ser Val Met His
                595                 600                 605
```

```
Glu Ala Leu His Asn His Tyr Thr Gln Lys Ser Leu Ser Leu Ser Pro
        610                 615                 620
Gly Lys
625

<210> SEQ ID NO 17
<211> LENGTH: 622
<212> TYPE: PRT
<213> ORGANISM: Artificial Sequence
<220> FEATURE:
<223> OTHER INFORMATION: AAT-hFc2 fusion protein

<400> SEQUENCE: 17

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335
```

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys Glu Arg Lys Cys Cys Val
385                 390                 395                 400

Glu Cys Pro Pro Cys Pro Ala Pro Pro Val Ala Gly Pro Ser Val Phe
                405                 410                 415

Leu Phe Pro Pro Lys Pro Lys Asp Thr Leu Met Ile Ser Arg Thr Pro
            420                 425                 430

Glu Val Thr Cys Val Val Val Asp Val Ser His Glu Asp Pro Glu Val
        435                 440                 445

Gln Phe Asn Trp Tyr Val Asp Gly Val Glu Val His Asn Ala Lys Thr
    450                 455                 460

Lys Pro Arg Glu Glu Gln Phe Asn Ser Thr Phe Arg Val Val Ser Val
465                 470                 475                 480

Leu Thr Val Val His Gln Asp Trp Leu Asn Gly Lys Glu Tyr Lys Cys
                485                 490                 495

Lys Val Ser Asn Lys Gly Leu Pro Ala Pro Ile Glu Lys Thr Ile Ser
            500                 505                 510

Lys Thr Lys Gly Gln Pro Arg Glu Pro Gln Val Tyr Thr Leu Pro Pro
        515                 520                 525

Ser Arg Glu Glu Met Thr Lys Asn Gln Val Ser Leu Thr Cys Leu Val
    530                 535                 540

Lys Gly Phe Tyr Pro Ser Asp Ile Ala Val Glu Trp Glu Ser Asn Gly
545                 550                 555                 560

Gln Pro Glu Asn Asn Tyr Lys Thr Thr Pro Pro Met Leu Asp Ser Asp
                565                 570                 575

Gly Ser Phe Phe Leu Tyr Ser Lys Leu Thr Val Asp Lys Ser Arg Trp
            580                 585                 590

Gln Gln Gly Asn Val Phe Ser Cys Ser Val Met His Glu Ala Leu His
        595                 600                 605

Asn His Tyr Thr Gln Lys Ser Leu Ser Leu Ser Pro Gly Lys
    610                 615                 620

<210> SEQ ID NO 18
<211> LENGTH: 626
<212> TYPE: PRT
<213> ORGANISM: Artificial Sequence
<220> FEATURE:
<223> OTHER INFORMATION: AAT-MM-EL-hFc1 fusion protein

<400> SEQUENCE: 18

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

-continued

Asn Phe Asn Leu Thr Glu Ile Pro Glu Ala Gln Ile His Glu Gly Phe
            85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
            115                 120                 125

Lys Phe Leu Glu Asp Val Lys Lys Leu Tyr His Ser Glu Ala Phe Thr
        130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
                180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
        210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
                260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Glu Phe
                340                 345                 350

Leu Glu Ala Ile Pro Leu Ser Ile Pro Pro Glu Val Lys Phe Asn Lys
        355                 360                 365

Pro Phe Val Phe Leu Met Ile Glu Gln Asn Thr Lys Ser Pro Leu Phe
        370                 375                 380

Met Gly Lys Val Val Asn Pro Thr Gln Lys Glu Pro Lys Ser Cys Asp
385                 390                 395                 400

Lys Thr His Thr Cys Pro Pro Cys Pro Ala Pro Glu Leu Leu Gly Gly
                405                 410                 415

Pro Ser Val Phe Leu Phe Pro Pro Lys Pro Lys Asp Thr Leu Met Ile
                420                 425                 430

Ser Arg Thr Pro Glu Val Thr Cys Val Val Val Asp Val Ser His Glu
        435                 440                 445

Asp Pro Glu Val Lys Phe Asn Trp Tyr Val Asp Gly Val Glu Val His
        450                 455                 460

Asn Ala Lys Thr Lys Pro Arg Glu Glu Gln Tyr Asn Ser Thr Tyr Arg
465                 470                 475                 480

Val Val Ser Val Leu Thr Val Leu His Gln Asp Trp Leu Asn Gly Lys
                485                 490                 495

```
Glu Tyr Lys Cys Lys Val Ser Asn Lys Ala Leu Pro Ala Pro Ile Glu
            500                 505                 510

Lys Thr Ile Ser Lys Ala Lys Gly Gln Pro Arg Glu Pro Gln Val Tyr
        515                 520                 525

Thr Leu Pro Pro Ser Arg Asp Glu Leu Thr Lys Asn Gln Val Ser Leu
    530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
                565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
        595                 600                 605

Glu Ala Leu His Asn His Tyr Thr Gln Lys Ser Leu Ser Leu Ser Pro
    610                 615                 620

Gly Lys
625

<210> SEQ ID NO 19
<211> LENGTH: 622
<212> TYPE: PRT
<213> ORGANISM: Artificial Sequence
<220> FEATURE:
<223> OTHER INFORMATION: AAT-MM-EL-hFc2 fusion protein

<400> SEQUENCE: 19

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220
```

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
        260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Glu Phe
        340                 345                 350

Leu Glu Ala Ile Pro Leu Ser Ile Pro Pro Glu Val Lys Phe Asn Lys
    355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys Glu Arg Lys Cys Cys Val
385                 390                 395                 400

Glu Cys Pro Pro Cys Pro Ala Pro Pro Val Ala Gly Pro Ser Val Phe
            405                 410                 415

Leu Phe Pro Pro Lys Pro Lys Asp Thr Leu Met Ile Ser Arg Thr Pro
        420                 425                 430

Glu Val Thr Cys Val Val Val Asp Val Ser His Glu Asp Pro Glu Val
    435                 440                 445

Gln Phe Asn Trp Tyr Val Asp Gly Val Glu Val His Asn Ala Lys Thr
450                 455                 460

Lys Pro Arg Glu Glu Gln Phe Asn Ser Thr Phe Arg Val Val Ser Val
465                 470                 475                 480

Leu Thr Val Val His Gln Asp Trp Leu Asn Gly Lys Glu Tyr Lys Cys
            485                 490                 495

Lys Val Ser Asn Lys Gly Leu Pro Ala Pro Ile Glu Lys Thr Ile Ser
        500                 505                 510

Lys Thr Lys Gly Gln Pro Arg Glu Pro Gln Val Tyr Thr Leu Pro Pro
    515                 520                 525

Ser Arg Glu Glu Met Thr Lys Asn Gln Val Ser Leu Thr Cys Leu Val
530                 535                 540

Lys Gly Phe Tyr Pro Ser Asp Ile Ala Val Glu Trp Glu Ser Asn Gly
545                 550                 555                 560

Gln Pro Glu Asn Asn Tyr Lys Thr Thr Pro Pro Met Leu Asp Ser Asp
            565                 570                 575

Gly Ser Phe Phe Leu Tyr Ser Lys Leu Thr Val Asp Lys Ser Arg Trp
        580                 585                 590

Gln Gln Gly Asn Val Phe Ser Cys Ser Val Met His Glu Ala Leu His
    595                 600                 605

Asn His Tyr Thr Gln Lys Ser Leu Ser Leu Ser Pro Gly Lys
610                 615                 620

<210> SEQ ID NO 20
<211> LENGTH: 622
<212> TYPE: PRT

<213> ORGANISM: Artificial Sequence
<220> FEATURE:
<223> OTHER INFORMATION: AAT-MM:LL-hFc2 fusion protein

<400> SEQUENCE: 20

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Leu Phe
            340                 345                 350

Leu Glu Ala Ile Pro Leu Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys Glu Arg Lys Cys Cys Val
```

```
                385                 390                 395                 400
Glu Cys Pro Pro Cys Pro Ala Pro Pro Val Ala Gly Pro Ser Val Phe
                    405                 410                 415

Leu Phe Pro Pro Lys Pro Lys Asp Thr Leu Met Ile Ser Arg Thr Pro
                420                 425                 430

Glu Val Thr Cys Val Val Val Asp Val Ser His Glu Asp Pro Glu Val
            435                 440                 445

Gln Phe Asn Trp Tyr Val Asp Gly Val Glu Val His Asn Ala Lys Thr
        450                 455                 460

Lys Pro Arg Glu Glu Gln Phe Asn Ser Thr Phe Arg Val Val Ser Val
465                 470                 475                 480

Leu Thr Val Val His Gln Asp Trp Leu Asn Gly Lys Glu Tyr Lys Cys
                485                 490                 495

Lys Val Ser Asn Lys Gly Leu Pro Ala Pro Ile Glu Lys Thr Ile Ser
                500                 505                 510

Lys Thr Lys Gly Gln Pro Arg Glu Pro Gln Val Tyr Thr Leu Pro Pro
            515                 520                 525

Ser Arg Glu Glu Met Thr Lys Asn Gln Val Ser Leu Thr Cys Leu Val
530                 535                 540

Lys Gly Phe Tyr Pro Ser Asp Ile Ala Val Glu Trp Glu Ser Asn Gly
545                 550                 555                 560

Gln Pro Glu Asn Asn Tyr Lys Thr Thr Pro Pro Met Leu Asp Ser Asp
                565                 570                 575

Gly Ser Phe Phe Leu Tyr Ser Lys Leu Thr Val Asp Lys Ser Arg Trp
            580                 585                 590

Gln Gln Gly Asn Val Phe Ser Cys Ser Val Met His Glu Ala Leu His
        595                 600                 605

Asn His Tyr Thr Gln Lys Ser Leu Ser Leu Ser Pro Gly Lys
            610                 615                 620

<210> SEQ ID NO 21
<211> LENGTH: 1025
<212> TYPE: PRT
<213> ORGANISM: Artificial Sequence
<220> FEATURE:
<223> OTHER INFORMATION: AAT-hFc1-AAT fusion protein

<400> SEQUENCE: 21

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
```

```
                130                 135                 140
Val Asn Phe Gly Asp Thr Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
                180                 185                 190

Lys Trp Glu Arg Pro Phe Glu Val Lys Asp Thr Glu Glu Asp Phe
                195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
                260                 265                 270

Thr Lys Phe Leu Glu Asn Glu Asp Arg Arg Ser Ala Ser Leu His Leu
                275                 280                 285

Pro Lys Leu Ser Ile Thr Gly Thr Tyr Asp Leu Lys Ser Val Leu Gly
                290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
                340                 345                 350

Leu Glu Ala Ile Pro Met Ser Ile Pro Pro Glu Val Lys Phe Asn Lys
                355                 360                 365

Pro Phe Val Phe Leu Met Ile Glu Gln Asn Thr Lys Ser Pro Leu Phe
                370                 375                 380

Met Gly Lys Val Val Asn Pro Thr Gln Lys Glu Pro Lys Ser Cys Asp
385                 390                 395                 400

Lys Thr His Thr Cys Pro Pro Cys Pro Ala Pro Glu Leu Leu Gly Gly
                405                 410                 415

Pro Ser Val Phe Leu Phe Pro Pro Lys Pro Lys Asp Thr Leu Met Ile
                420                 425                 430

Ser Arg Thr Pro Glu Val Thr Cys Val Val Val Asp Val Ser His Glu
                435                 440                 445

Asp Pro Glu Val Lys Phe Asn Trp Tyr Val Asp Gly Val Glu Val His
                450                 455                 460

Asn Ala Lys Thr Lys Pro Arg Glu Glu Gln Tyr Asn Ser Thr Tyr Arg
465                 470                 475                 480

Val Val Ser Val Leu Thr Val Leu His Gln Asp Trp Leu Asn Gly Lys
                485                 490                 495

Glu Tyr Lys Cys Lys Val Ser Asn Lys Ala Leu Pro Ala Pro Ile Glu
                500                 505                 510

Lys Thr Ile Ser Lys Ala Lys Gly Gln Pro Arg Glu Pro Gln Val Tyr
                515                 520                 525

Thr Leu Pro Pro Ser Arg Asp Glu Leu Thr Lys Asn Gln Val Ser Leu
                530                 535                 540

Thr Cys Leu Val Lys Gly Phe Tyr Pro Ser Asp Ile Ala Val Glu Trp
545                 550                 555                 560
```

-continued

```
Glu Ser Asn Gly Gln Pro Glu Asn Asn Tyr Lys Thr Thr Pro Pro Val
            565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
            595                 600                 605

Glu Ala Leu His Asn His Tyr Thr Gln Lys Ser Leu Ser Leu Ser Pro
            610                 615                 620

Gly Lys Ala Ser Thr Gly Ser Glu Asp Pro Gln Gly Asp Ala Ala Gln
625                 630                 635                 640

Lys Thr Asp Thr Ser His His Asp Gln Asp His Pro Thr Phe Asn Lys
            645                 650                 655

Ile Thr Pro Asn Leu Ala Glu Phe Ala Phe Ser Leu Tyr Arg Gln Leu
            660                 665                 670

Ala His Gln Ser Asn Ser Thr Asn Ile Phe Phe Ser Pro Val Ser Ile
            675                 680                 685

Ala Thr Ala Phe Ala Met Leu Ser Leu Gly Thr Lys Ala Asp Thr His
            690                 695                 700

Asp Glu Ile Leu Glu Gly Leu Asn Phe Asn Leu Thr Glu Ile Pro Glu
705                 710                 715                 720

Ala Gln Ile His Glu Gly Phe Gln Glu Leu Leu Arg Thr Leu Asn Gln
            725                 730                 735

Pro Asp Ser Gln Leu Gln Leu Thr Thr Gly Asn Gly Leu Phe Leu Ser
            740                 745                 750

Glu Gly Leu Lys Leu Val Asp Lys Phe Leu Glu Asp Val Lys Lys Leu
            755                 760                 765

Tyr His Ser Glu Ala Phe Thr Val Asn Phe Gly Asp Thr Glu Glu Ala
            770                 775                 780

Lys Lys Gln Ile Asn Asp Tyr Val Glu Lys Gly Thr Gln Gly Lys Ile
785                 790                 795                 800

Val Asp Leu Val Lys Glu Leu Asp Arg Asp Thr Val Phe Ala Leu Val
            805                 810                 815

Asn Tyr Ile Phe Phe Lys Gly Lys Trp Glu Arg Pro Phe Glu Val Lys
            820                 825                 830

Asp Thr Glu Glu Glu Asp Phe His Val Asp Gln Val Thr Thr Val Lys
            835                 840                 845

Val Pro Met Met Lys Arg Leu Gly Met Phe Asn Ile Gln His Cys Lys
850                 855                 860

Lys Leu Ser Ser Trp Val Leu Leu Met Lys Tyr Leu Gly Asn Ala Thr
865                 870                 875                 880

Ala Ile Phe Phe Leu Pro Asp Glu Gly Lys Leu Gln His Leu Glu Asn
            885                 890                 895

Glu Leu Thr His Asp Ile Ile Thr Lys Phe Leu Glu Asn Glu Asp Arg
            900                 905                 910

Arg Ser Ala Ser Leu His Leu Pro Lys Leu Ser Ile Thr Gly Thr Tyr
            915                 920                 925

Asp Leu Lys Ser Val Leu Gly Gln Leu Gly Ile Thr Lys Val Phe Ser
            930                 935                 940

Asn Gly Ala Asp Leu Ser Gly Val Thr Glu Glu Ala Pro Leu Lys Leu
945                 950                 955                 960

Ser Lys Ala Val His Lys Ala Val Leu Thr Ile Asp Glu Lys Gly Thr
            965                 970                 975
```

Glu Ala Ala Gly Ala Met Phe Leu Glu Ala Ile Pro Met Ser Ile Pro
                980                 985                 990

Pro Glu Val Lys Phe Asn Lys Pro Phe Val Phe Leu Met Ile Glu Gln
            995                1000                1005

Asn Thr Lys Ser Pro Leu Phe Met Gly Lys Val Val Asn Pro Thr
        1010                1015                1020

Gln Lys
    1025

<210> SEQ ID NO 22
<211> LENGTH: 616
<212> TYPE: PRT
<213> ORGANISM: Artificial Sequence
<220> FEATURE:
<223> OTHER INFORMATION: D2E7-Light Chain-AAT fusion protein

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Ser Glu Asp
    210                 215                 220

Pro Gln Gly Asp Ala Ala Gln Lys Thr Asp Thr Ser His His Asp Gln
225                 230                 235                 240

Asp His Pro Thr Phe Asn Lys Ile Thr Pro Asn Leu Ala Glu Phe Ala
                245                 250                 255

Phe Ser Leu Tyr Arg Gln Leu Ala His Gln Ser Asn Ser Thr Asn Ile
            260                 265                 270

Phe Phe Ser Pro Val Ser Ile Ala Thr Ala Phe Ala Met Leu Ser Leu
        275                 280                 285

Gly Thr Lys Ala Asp Thr His Asp Glu Ile Leu Glu Gly Leu Asn Phe
    290                 295                 300

```
Asn Leu Thr Glu Ile Pro Glu Ala Gln Ile His Glu Gly Phe Gln Glu
305                 310                 315                 320

Leu Leu Arg Thr Leu Asn Gln Pro Asp Ser Gln Leu Gln Leu Thr Thr
            325                 330                 335

Gly Asn Gly Leu Phe Leu Ser Glu Gly Leu Lys Leu Val Asp Lys Phe
                340                 345                 350

Leu Glu Asp Val Lys Lys Leu Tyr His Ser Glu Ala Phe Thr Val Asn
            355                 360                 365

Phe Gly Asp Thr Glu Glu Ala Lys Lys Gln Ile Asn Asp Tyr Val Glu
370                 375                 380

Lys Gly Thr Gln Gly Lys Ile Val Asp Leu Val Lys Glu Leu Asp Arg
385                 390                 395                 400

Asp Thr Val Phe Ala Leu Val Asn Tyr Ile Phe Phe Lys Gly Lys Trp
                405                 410                 415

Glu Arg Pro Phe Glu Val Lys Asp Thr Glu Glu Glu Asp Phe His Val
                420                 425                 430

Asp Gln Val Thr Thr Val Lys Val Pro Met Met Lys Arg Leu Gly Met
            435                 440                 445

Phe Asn Ile Gln His Cys Lys Lys Leu Ser Ser Trp Val Leu Leu Met
450                 455                 460

Lys Tyr Leu Gly Asn Ala Thr Ala Ile Phe Phe Leu Pro Asp Glu Gly
465                 470                 475                 480

Lys Leu Gln His Leu Glu Asn Glu Leu Thr His Asp Ile Ile Thr Lys
                485                 490                 495

Phe Leu Glu Asn Glu Asp Arg Arg Ser Ala Ser Leu His Leu Pro Lys
                500                 505                 510

Leu Ser Ile Thr Gly Thr Tyr Asp Leu Lys Ser Val Leu Gly Gln Leu
            515                 520                 525

Gly Ile Thr Lys Val Phe Ser Asn Gly Ala Asp Leu Ser Gly Val Thr
530                 535                 540

Glu Glu Ala Pro Leu Lys Leu Ser Lys Ala Val His Lys Ala Val Leu
545                 550                 555                 560

Thr Ile Asp Glu Lys Gly Thr Glu Ala Ala Gly Ala Met Phe Leu Glu
                565                 570                 575

Ala Ile Pro Met Ser Ile Pro Pro Glu Val Lys Phe Asn Lys Pro Phe
                580                 585                 590

Val Phe Leu Met Ile Glu Gln Asn Thr Lys Ser Pro Leu Phe Met Gly
            595                 600                 605

Lys Val Val Asn Pro Thr Gln Lys
    610                 615

<210> SEQ ID NO 23
<211> LENGTH: 613
<212> TYPE: PRT
<213> ORGANISM: Artificial Sequence
<220> FEATURE:
<223> OTHER INFORMATION: D2E7-Light Chain-AAT ASTGS Linker fusion
      protein

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45
```

```
Tyr Ala Ala Ser Thr Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Val Ala Thr Tyr Tyr Cys Gln Arg Tyr Asn Arg Ala Pro Tyr
                 85                  90                  95
Thr Phe Gly Gln Gly Thr Lys Val Glu Ile Lys Arg Thr Val Ala Ala
             100                 105                 110
Pro Ser Val Phe Ile Phe Pro Pro Ser Asp Glu Gln Leu Lys Ser Gly
         115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
             180                 185                 190
Ala Cys Glu Val Thr His Gln Gly Leu Ser Ser Pro Val Thr Lys Ser
         195                 200                 205
Phe Asn Arg Gly Glu Cys Ala Ser Thr Gly Ser Glu Asp Pro Gln Gly
210                 215                 220
Asp Ala Ala Gln Lys Thr Asp Thr Ser His His Asp Gln Asp His Pro
225                 230                 235                 240
Thr Phe Asn Lys Ile Thr Pro Asn Leu Ala Glu Phe Ala Phe Ser Leu
                245                 250                 255
Tyr Arg Gln Leu Ala His Gln Ser Asn Ser Thr Asn Ile Phe Phe Ser
             260                 265                 270
Pro Val Ser Ile Ala Thr Ala Phe Ala Met Leu Ser Leu Gly Thr Lys
         275                 280                 285
Ala Asp Thr His Asp Glu Ile Leu Glu Gly Leu Asn Phe Asn Leu Thr
290                 295                 300
Glu Ile Pro Glu Ala Gln Ile His Glu Gly Phe Gln Glu Leu Leu Arg
305                 310                 315                 320
Thr Leu Asn Gln Pro Asp Ser Gln Leu Gln Leu Thr Thr Gly Asn Gly
                325                 330                 335
Leu Phe Leu Ser Glu Gly Leu Lys Leu Val Asp Lys Phe Leu Glu Asp
             340                 345                 350
Val Lys Lys Leu Tyr His Ser Glu Ala Phe Thr Val Asn Phe Gly Asp
         355                 360                 365
Thr Glu Glu Ala Lys Lys Gln Ile Asn Asp Tyr Val Glu Lys Gly Thr
370                 375                 380
Gln Gly Lys Ile Val Asp Leu Val Lys Glu Leu Asp Arg Asp Thr Val
385                 390                 395                 400
Phe Ala Leu Val Asn Tyr Ile Phe Phe Lys Gly Lys Trp Glu Arg Pro
                405                 410                 415
Phe Glu Val Lys Asp Thr Glu Glu Asp Phe His Val Asp Gln Val
             420                 425                 430
Thr Thr Val Lys Val Pro Met Met Lys Arg Leu Gly Met Phe Asn Ile
             435                 440                 445
Gln His Cys Lys Lys Leu Ser Ser Trp Val Leu Leu Met Lys Tyr Leu
450                 455                 460
```

Gly Asn Ala Thr Ala Ile Phe Phe Leu Pro Asp Glu Gly Lys Leu Gln
465                 470                 475                 480

His Leu Glu Asn Glu Leu Thr His Asp Ile Ile Thr Lys Phe Leu Glu
            485                 490                 495

Asn Glu Asp Arg Arg Ser Ala Ser Leu His Leu Pro Lys Leu Ser Ile
        500                 505                 510

Thr Gly Thr Tyr Asp Leu Lys Ser Val Leu Gly Gln Leu Gly Ile Thr
    515                 520                 525

Lys Val Phe Ser Asn Gly Ala Asp Leu Ser Gly Val Thr Glu Glu Ala
530                 535                 540

Pro Leu Lys Leu Ser Lys Ala Val His Lys Ala Val Leu Thr Ile Asp
545                 550                 555                 560

Glu Lys Gly Thr Glu Ala Ala Gly Ala Met Phe Leu Glu Ala Ile Pro
                565                 570                 575

Met Ser Ile Pro Pro Glu Val Lys Phe Asn Lys Pro Phe Val Phe Leu
            580                 585                 590

Met Ile Glu Gln Asn Thr Lys Ser Pro Leu Phe Met Gly Lys Val Val
        595                 600                 605

Asn Pro Thr Gln Lys
    610

<210> SEQ ID NO 24
<211> LENGTH: 853
<212> TYPE: PRT
<213> ORGANISM: Artificial Sequence
<220> FEATURE:
<223> OTHER INFORMATION: D2E7-Heavy Chain-AAT (G3S)2 Linker fusion
      protein

<400> SEQUENCE: 24

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

```
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys Gly Gly Gly Ser Gly Gly Gly Ser Glu Asp Pro Gln Gly
450                 455                 460
Asp Ala Ala Gln Lys Thr Asp Thr Ser His His Asp Gln Asp His Pro
465                 470                 475                 480
Thr Phe Asn Lys Ile Thr Pro Asn Leu Ala Glu Phe Ala Phe Ser Leu
                485                 490                 495
Tyr Arg Gln Leu Ala His Gln Ser Asn Ser Thr Asn Ile Phe Phe Ser
            500                 505                 510
Pro Val Ser Ile Ala Thr Ala Phe Ala Met Leu Ser Leu Gly Thr Lys
        515                 520                 525
Ala Asp Thr His Asp Glu Ile Leu Glu Gly Leu Asn Phe Asn Leu Thr
530                 535                 540
Glu Ile Pro Glu Ala Gln Ile His Glu Gly Phe Gln Glu Leu Leu Arg
545                 550                 555                 560
Thr Leu Asn Gln Pro Asp Ser Gln Leu Gln Leu Thr Thr Gly Asn Gly
                565                 570                 575
Leu Phe Leu Ser Glu Gly Leu Lys Leu Val Asp Lys Phe Leu Glu Asp
            580                 585                 590
Val Lys Lys Leu Tyr His Ser Glu Ala Phe Thr Val Asn Phe Gly Asp
        595                 600                 605
Thr Glu Glu Ala Lys Lys Gln Ile Asn Asp Tyr Val Glu Lys Gly Thr
610                 615                 620
```

```
Gln Gly Lys Ile Val Asp Leu Val Lys Glu Leu Asp Arg Asp Thr Val
625                 630                 635                 640

Phe Ala Leu Val Asn Tyr Ile Phe Phe Lys Gly Lys Trp Glu Arg Pro
            645                 650                 655

Phe Glu Val Lys Asp Thr Glu Glu Asp Phe His Val Asp Gln Val
            660                 665                 670

Thr Thr Val Lys Val Pro Met Met Lys Arg Leu Gly Met Phe Asn Ile
        675                 680                 685

Gln His Cys Lys Lys Leu Ser Ser Trp Val Leu Leu Met Lys Tyr Leu
    690                 695                 700

Gly Asn Ala Thr Ala Ile Phe Phe Leu Pro Asp Glu Gly Lys Leu Gln
705                 710                 715                 720

His Leu Glu Asn Glu Leu Thr His Asp Ile Ile Thr Lys Phe Leu Glu
                725                 730                 735

Asn Glu Asp Arg Arg Ser Ala Ser Leu His Leu Pro Lys Leu Ser Ile
                740                 745                 750

Thr Gly Thr Tyr Asp Leu Lys Ser Val Leu Gly Gln Leu Gly Ile Thr
            755                 760                 765

Lys Val Phe Ser Asn Gly Ala Asp Leu Ser Gly Val Thr Glu Glu Ala
770                 775                 780

Pro Leu Lys Leu Ser Lys Ala Val His Lys Ala Val Leu Thr Ile Asp
785                 790                 795                 800

Glu Lys Gly Thr Glu Ala Ala Gly Ala Met Phe Leu Glu Ala Ile Pro
                805                 810                 815

Met Ser Ile Pro Pro Glu Val Lys Phe Asn Lys Pro Phe Val Phe Leu
                820                 825                 830

Met Ile Glu Gln Asn Thr Lys Ser Pro Leu Phe Met Gly Lys Val Val
            835                 840                 845

Asn Pro Thr Gln Lys
            850

<210> SEQ ID NO 25
<211> LENGTH: 850
<212> TYPE: PRT
<213> ORGANISM: Artificial Sequence
<220> FEATURE:
<223> OTHER INFORMATION: D2E7-Heavy Chain-AAT ASTGS Linker fusion
      protein

<400> SEQUENCE: 25

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125
```

-continued

```
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys Ala Ser Thr Gly Ser Glu Asp Pro Gln Gly Asp Ala Ala
    450                 455                 460
Gln Lys Thr Asp Thr Ser His His Asp Gln Asp His Pro Thr Phe Asn
465                 470                 475                 480
Lys Ile Thr Pro Asn Leu Ala Glu Phe Ala Phe Ser Leu Tyr Arg Gln
                485                 490                 495
Leu Ala His Gln Ser Asn Ser Thr Asn Ile Phe Phe Ser Pro Val Ser
            500                 505                 510
Ile Ala Thr Ala Phe Ala Met Leu Ser Leu Gly Thr Lys Ala Asp Thr
        515                 520                 525
His Asp Glu Ile Leu Glu Gly Leu Asn Phe Asn Leu Thr Glu Ile Pro
    530                 535                 540
```

```
Glu Ala Gln Ile His Glu Gly Phe Gln Glu Leu Leu Arg Thr Leu Asn
545                 550                 555                 560

Gln Pro Asp Ser Gln Leu Gln Leu Thr Thr Gly Asn Gly Leu Phe Leu
            565                 570                 575

Ser Glu Gly Leu Lys Leu Val Asp Lys Phe Leu Glu Asp Val Lys Lys
        580                 585                 590

Leu Tyr His Ser Glu Ala Phe Thr Val Asn Phe Gly Asp Thr Glu Glu
    595                 600                 605

Ala Lys Lys Gln Ile Asn Asp Tyr Val Glu Lys Gly Thr Gln Gly Lys
610                 615                 620

Ile Val Asp Leu Val Lys Glu Leu Asp Arg Asp Thr Val Phe Ala Leu
625                 630                 635                 640

Val Asn Tyr Ile Phe Phe Lys Gly Lys Trp Glu Arg Pro Phe Glu Val
            645                 650                 655

Lys Asp Thr Glu Glu Glu Asp Phe His Val Asp Gln Val Thr Thr Val
        660                 665                 670

Lys Val Pro Met Met Lys Arg Leu Gly Met Phe Asn Ile Gln His Cys
    675                 680                 685

Lys Lys Leu Ser Ser Trp Val Leu Leu Met Lys Tyr Leu Gly Asn Ala
690                 695                 700

Thr Ala Ile Phe Phe Leu Pro Asp Glu Gly Lys Leu Gln His Leu Glu
705                 710                 715                 720

Asn Glu Leu Thr His Asp Ile Ile Thr Lys Phe Leu Glu Asn Glu Asp
            725                 730                 735

Arg Arg Ser Ala Ser Leu His Leu Pro Lys Leu Ser Ile Thr Gly Thr
        740                 745                 750

Tyr Asp Leu Lys Ser Val Leu Gly Gln Leu Gly Ile Thr Lys Val Phe
    755                 760                 765

Ser Asn Gly Ala Asp Leu Ser Gly Val Thr Glu Glu Ala Pro Leu Lys
770                 775                 780

Leu Ser Lys Ala Val His Lys Ala Val Leu Thr Ile Asp Glu Lys Gly
785                 790                 795                 800

Thr Glu Ala Ala Gly Ala Met Phe Leu Glu Ala Ile Pro Met Ser Ile
            805                 810                 815

Pro Pro Glu Val Lys Phe Asn Lys Pro Phe Val Phe Leu Met Ile Glu
        820                 825                 830

Gln Asn Thr Lys Ser Pro Leu Phe Met Gly Lys Val Val Asn Pro Thr
    835                 840                 845

Gln Lys
    850
```

<210> SEQ ID NO 26
<211> LENGTH: 869
<212> TYPE: PRT
<213> ORGANISM: Artificial Sequence
<220> FEATURE:
<223> OTHER INFORMATION: TNFR2-ECD-Fc1-AAT(G3S)2 Linker fusion protein

<400> SEQUENCE: 26

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45
```

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
             100                 105                 110

Arg Leu Cys Ala Pro Leu Arg Lys Cys Arg Pro Gly Phe Gly Val Ala
         115                 120                 125

Arg Pro Gly Thr Glu Thr Ser Asp Val Val Cys Lys Pro Cys Ala Pro
     130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Gln Val Lys Phe Asn Trp Tyr Val Asp Gly Val Gln Val
    290                 295                 300

His Asn Ala Lys Thr Lys Pro Arg Glu Gln Gln Tyr Asn Ser Thr Tyr
305                 310                 315                 320

Arg Val Val Ser Val Leu Thr Val Leu His Gln Asn Trp Leu Asp Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Gly Gly Gly Ser Gly Gly Gly Ser Glu Asp Pro Gln Gly

```
                465                 470                 475                 480
Asp Ala Ala Gln Lys Thr Asp Thr Ser His His Asp Gln Asp His Pro
                    485                 490                 495
Thr Phe Asn Lys Ile Thr Pro Asn Leu Ala Glu Phe Ala Phe Ser Leu
                500                 505                 510
Tyr Arg Gln Leu Ala His Gln Ser Asn Ser Thr Asn Ile Phe Phe Ser
            515                 520                 525
Pro Val Ser Ile Ala Thr Ala Phe Ala Met Leu Ser Leu Gly Thr Lys
        530                 535                 540
Ala Asp Thr His Asp Glu Ile Leu Glu Gly Leu Asn Phe Asn Leu Thr
545                 550                 555                 560
Glu Ile Pro Glu Ala Gln Ile His Glu Gly Phe Gln Glu Leu Leu Arg
                565                 570                 575
Thr Leu Asn Gln Pro Asp Ser Gln Leu Gln Leu Thr Thr Gly Asn Gly
                580                 585                 590
Leu Phe Leu Ser Glu Gly Leu Lys Leu Val Asp Lys Phe Leu Glu Asp
            595                 600                 605
Val Lys Lys Leu Tyr His Ser Glu Ala Phe Thr Val Asn Phe Gly Asp
        610                 615                 620
Thr Glu Glu Ala Lys Lys Gln Ile Asn Asp Tyr Val Glu Lys Gly Thr
625                 630                 635                 640
Gln Gly Lys Ile Val Asp Leu Val Lys Glu Leu Asp Arg Asp Thr Val
                645                 650                 655
Phe Ala Leu Val Asn Tyr Ile Phe Phe Lys Gly Lys Trp Glu Arg Pro
                660                 665                 670
Phe Glu Val Lys Asp Thr Glu Glu Asp Phe His Val Asp Gln Val
            675                 680                 685
Thr Thr Val Lys Val Pro Met Met Lys Arg Leu Gly Met Phe Asn Ile
        690                 695                 700
Gln His Cys Lys Lys Leu Ser Ser Trp Val Leu Leu Met Lys Tyr Leu
705                 710                 715                 720
Gly Asn Ala Thr Ala Ile Phe Phe Leu Pro Asp Glu Gly Lys Leu Gln
                725                 730                 735
His Leu Glu Asn Glu Leu Thr His Asp Ile Ile Thr Lys Phe Leu Glu
                740                 745                 750
Asn Glu Asp Arg Arg Ser Ala Ser Leu His Leu Pro Lys Leu Ser Ile
            755                 760                 765
Thr Gly Thr Tyr Asp Leu Lys Ser Val Leu Gly Gln Leu Gly Ile Thr
        770                 775                 780
Lys Val Phe Ser Asn Gly Ala Asp Leu Ser Gly Val Thr Glu Glu Ala
785                 790                 795                 800
Pro Leu Lys Leu Ser Lys Ala Val His Lys Ala Val Leu Thr Ile Asp
                805                 810                 815
Glu Lys Gly Thr Glu Ala Ala Gly Ala Met Phe Leu Glu Ala Ile Pro
                820                 825                 830
Met Ser Ile Pro Pro Glu Val Lys Phe Asn Lys Pro Phe Val Phe Leu
            835                 840                 845
Met Ile Glu Gln Asn Thr Lys Ser Pro Leu Phe Met Gly Lys Val Val
        850                 855                 860
Asn Pro Thr Gln Lys
865

<210> SEQ ID NO 27
```

<211> LENGTH: 866
<212> TYPE: PRT
<213> ORGANISM: Artificial Sequence
<220> FEATURE:
<223> OTHER INFORMATION: TNFR2-ECD-Fc1-AAT ASTGS Linker fusion protein

<400> SEQUENCE: 27

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Gln Val Lys Phe Asn Trp Tyr Val Asp Gly Val Gln Val
    290                 295                 300

His Asn Ala Lys Thr Lys Pro Arg Glu Gln Gln Tyr Asn Ser Thr Tyr
305                 310                 315                 320

Arg Val Val Ser Val Leu Thr Val Leu His Gln Asn Trp Leu Asp Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380
```

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys Ala Ser Thr Gly Ser Glu Asp Pro Gln Gly Asp Ala Ala
465                 470                 475                 480

Gln Lys Thr Asp Thr Ser His His Asp Gln Asp His Pro Thr Phe Asn
                485                 490                 495

Lys Ile Thr Pro Asn Leu Ala Glu Phe Ala Phe Ser Leu Tyr Arg Gln
            500                 505                 510

Leu Ala His Gln Ser Asn Ser Thr Asn Ile Phe Phe Ser Pro Val Ser
        515                 520                 525

Ile Ala Thr Ala Phe Ala Met Leu Ser Leu Gly Thr Lys Ala Asp Thr
530                 535                 540

His Asp Glu Ile Leu Glu Gly Leu Asn Phe Asn Leu Thr Glu Ile Pro
545                 550                 555                 560

Glu Ala Gln Ile His Glu Gly Phe Gln Glu Leu Leu Arg Thr Leu Asn
                565                 570                 575

Gln Pro Asp Ser Gln Leu Gln Leu Thr Thr Gly Asn Gly Leu Phe Leu
            580                 585                 590

Ser Glu Gly Leu Lys Leu Val Asp Lys Phe Leu Glu Asp Val Lys Lys
        595                 600                 605

Leu Tyr His Ser Glu Ala Phe Thr Val Asn Phe Gly Asp Thr Glu Glu
610                 615                 620

Ala Lys Lys Gln Ile Asn Asp Tyr Val Glu Lys Gly Thr Gln Gly Lys
625                 630                 635                 640

Ile Val Asp Leu Val Lys Glu Leu Asp Arg Asp Thr Val Phe Ala Leu
                645                 650                 655

Val Asn Tyr Ile Phe Phe Lys Gly Lys Trp Glu Arg Pro Phe Glu Val
            660                 665                 670

Lys Asp Thr Glu Glu Glu Asp Phe His Val Asp Gln Val Thr Thr Val
        675                 680                 685

Lys Val Pro Met Met Lys Arg Leu Gly Met Phe Asn Ile Gln His Cys
        690                 695                 700

Lys Lys Leu Ser Ser Trp Val Leu Leu Met Lys Tyr Leu Gly Asn Ala
705                 710                 715                 720

Thr Ala Ile Phe Phe Leu Pro Asp Glu Gly Lys Leu Gln His Leu Glu
                725                 730                 735

Asn Glu Leu Thr His Asp Ile Ile Thr Lys Phe Leu Glu Asn Glu Asp
            740                 745                 750

Arg Arg Ser Ala Ser Leu His Leu Pro Lys Leu Ser Ile Thr Gly Thr
        755                 760                 765

Tyr Asp Leu Lys Ser Val Leu Gly Gln Leu Gly Ile Thr Lys Val Phe
        770                 775                 780

Ser Asn Gly Ala Asp Leu Ser Gly Val Thr Glu Glu Ala Pro Leu Lys
785                 790                 795                 800
```

```
Leu Ser Lys Ala Val His Lys Ala Val Leu Thr Ile Asp Glu Lys Gly
            805                 810                 815

Thr Glu Ala Ala Gly Ala Met Phe Leu Glu Ala Ile Pro Met Ser Ile
        820                 825                 830

Pro Pro Glu Val Lys Phe Asn Lys Pro Phe Val Phe Leu Met Ile Glu
            835                 840                 845

Gln Asn Thr Lys Ser Pro Leu Phe Met Gly Lys Val Val Asn Pro Thr
850                 855                 860

Gln Lys
865

<210> SEQ ID NO 28
<211> LENGTH: 738
<212> TYPE: PRT
<213> ORGANISM: Artificial Sequence
<220> FEATURE:
<223> OTHER INFORMATION: AAT-hFc1-SLPI fusion protein

<400> SEQUENCE: 28

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285
```

```
Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
                340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys Glu Pro Lys Ser Cys Asp
385                 390                 395                 400

Lys Thr His Thr Cys Pro Pro Cys Pro Ala Pro Glu Leu Leu Gly Gly
                405                 410                 415

Pro Ser Val Phe Leu Phe Pro Pro Lys Pro Lys Asp Thr Leu Met Ile
                420                 425                 430

Ser Arg Thr Pro Glu Val Thr Cys Val Val Val Asp Val Ser His Glu
            435                 440                 445

Asp Pro Glu Val Lys Phe Asn Trp Tyr Val Asp Gly Val Glu Val His
    450                 455                 460

Asn Ala Lys Thr Lys Pro Arg Glu Glu Gln Tyr Asn Ser Thr Tyr Arg
465                 470                 475                 480

Val Val Ser Val Leu Thr Val Leu His Gln Asp Trp Leu Asn Gly Lys
                485                 490                 495

Glu Tyr Lys Cys Lys Val Ser Asn Lys Ala Leu Pro Ala Pro Ile Glu
            500                 505                 510

Lys Thr Ile Ser Lys Ala Lys Gly Gln Pro Arg Glu Pro Gln Val Tyr
            515                 520                 525

Thr Leu Pro Pro Ser Arg Asp Glu Leu Thr Lys Asn Gln Val Ser Leu
    530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
                565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
            595                 600                 605

Glu Ala Leu His Asn His Tyr Thr Gln Lys Ser Leu Ser Leu Ser Pro
610                 615                 620

Gly Lys Ala Ser Thr Gly Ser Ser Gly Lys Ser Phe Lys Ala Gly Val
625                 630                 635                 640

Cys Pro Pro Lys Lys Ser Ala Gln Cys Leu Arg Tyr Lys Lys Pro Glu
                645                 650                 655

Cys Gln Ser Asp Trp Gln Cys Pro Gly Lys Lys Arg Cys Cys Pro Asp
                660                 665                 670

Thr Cys Gly Ile Lys Cys Leu Asp Pro Val Asp Thr Pro Asn Pro Thr
            675                 680                 685

Arg Arg Lys Pro Gly Lys Cys Pro Val Thr Tyr Gly Gln Cys Leu Met
    690                 695                 700

Leu Asn Pro Pro Asn Phe Cys Glu Met Asp Gly Gln Cys Lys Arg Asp
```

-continued

```
                705                 710                 715                 720
Leu Lys Cys Cys Met Gly Met Cys Gly Lys Ser Cys Val Ser Pro Val
                    725                 730                 735

Lys Ala

<210> SEQ ID NO 29
<211> LENGTH: 726
<212> TYPE: PRT
<213> ORGANISM: Artificial Sequence
<220> FEATURE:
<223> OTHER INFORMATION: AAT-hFc1-Elafin fusion protein

<400> SEQUENCE: 29

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335
```

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys Glu Pro Lys Ser Cys Asp
385                 390                 395                 400

Lys Thr His Thr Cys Pro Pro Cys Pro Ala Pro Glu Leu Leu Gly Gly
            405                 410                 415

Pro Ser Val Phe Leu Phe Pro Pro Lys Pro Lys Asp Thr Leu Met Ile
            420                 425                 430

Ser Arg Thr Pro Glu Val Thr Cys Val Val Val Asp Val Ser His Glu
            435                 440                 445

Asp Pro Glu Val Lys Phe Asn Trp Tyr Val Asp Gly Val Glu Val His
        450                 455                 460

Asn Ala Lys Thr Lys Pro Arg Glu Glu Gln Tyr Asn Ser Thr Tyr Arg
465                 470                 475                 480

Val Val Ser Val Leu Thr Val Leu His Gln Asp Trp Leu Asn Gly Lys
            485                 490                 495

Glu Tyr Lys Cys Lys Val Ser Asn Lys Ala Leu Pro Ala Pro Ile Glu
            500                 505                 510

Lys Thr Ile Ser Lys Ala Lys Gly Gln Pro Arg Glu Pro Gln Val Tyr
            515                 520                 525

Thr Leu Pro Pro Ser Arg Asp Glu Leu Thr Lys Asn Gln Val Ser Leu
            530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
            565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
            595                 600                 605

Glu Ala Leu His Asn His Tyr Thr Gln Lys Ser Leu Ser Leu Ser Pro
        610                 615                 620

Gly Lys Ala Ser Thr Gly Ser Ala Val Thr Gly Val Pro Val Lys Gly
625                 630                 635                 640

Gln Asp Thr Val Lys Gly Arg Val Pro Phe Asn Gly Gln Asp Pro Val
            645                 650                 655

Lys Gly Gln Val Ser Val Lys Gly Gln Asp Lys Val Lys Ala Gln Glu
            660                 665                 670

Pro Val Lys Gly Pro Val Ser Thr Lys Pro Gly Ser Cys Pro Ile Ile
            675                 680                 685

Leu Ile Arg Cys Ala Met Leu Asn Pro Pro Asn Arg Cys Leu Lys Asp
            690                 695                 700

Thr Asp Cys Pro Gly Ile Lys Lys Cys Cys Glu Gly Ser Cys Gly Met
705                 710                 715                 720

Ala Cys Phe Val Pro Gln
                725

<210> SEQ ID NO 30
<211> LENGTH: 984

```
<212> TYPE: PRT
<213> ORGANISM: Artificial Sequence
<220> FEATURE:
<223> OTHER INFORMATION: AAT-HSA fusion protein

<400> SEQUENCE: 30

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380
```

-continued

```
Met Gly Lys Val Val Asn Pro Thr Gln Lys Ala Ser Thr Gly Ser Asp
385                 390                 395                 400

Ala His Lys Ser Glu Val Ala His Arg Phe Lys Asp Leu Gly Glu Glu
                405                 410                 415

Asn Phe Lys Ala Leu Val Leu Ile Ala Phe Ala Gln Tyr Leu Gln Gln
            420                 425                 430

Cys Pro Phe Glu Asp His Val Lys Leu Val Asn Glu Val Thr Glu Phe
        435                 440                 445

Ala Lys Thr Cys Val Ala Asp Glu Ser Ala Glu Asn Cys Asp Lys Ser
    450                 455                 460

Leu His Thr Leu Phe Gly Asp Lys Leu Cys Thr Val Ala Thr Leu Arg
465                 470                 475                 480

Glu Thr Tyr Gly Glu Met Ala Asp Cys Cys Ala Lys Gln Glu Pro Glu
                485                 490                 495

Arg Asn Glu Cys Phe Leu Gln His Lys Asp Asp Asn Pro Asn Leu Pro
            500                 505                 510

Arg Leu Val Arg Pro Glu Val Asp Val Met Cys Thr Ala Phe His Asp
        515                 520                 525

Asn Glu Glu Thr Phe Leu Lys Lys Tyr Leu Tyr Glu Ile Ala Arg Arg
    530                 535                 540

His Pro Tyr Phe Tyr Ala Pro Glu Leu Leu Phe Phe Ala Lys Arg Tyr
545                 550                 555                 560

Lys Ala Ala Phe Thr Glu Cys Cys Gln Ala Ala Asp Lys Ala Ala Cys
                565                 570                 575

Leu Leu Pro Lys Leu Asp Glu Leu Arg Asp Glu Gly Lys Ala Ser Ser
            580                 585                 590

Ala Lys Gln Arg Leu Lys Cys Ala Ser Leu Gln Lys Phe Gly Glu Arg
        595                 600                 605

Ala Phe Lys Ala Trp Ala Val Ala Arg Leu Ser Gln Arg Phe Pro Lys
    610                 615                 620

Ala Glu Phe Ala Glu Val Ser Lys Leu Val Thr Asp Leu Thr Lys Val
625                 630                 635                 640

His Thr Glu Cys Cys His Gly Asp Leu Leu Glu Cys Ala Asp Asp Arg
                645                 650                 655

Ala Asp Leu Ala Lys Tyr Ile Cys Glu Asn Gln Asp Ser Ile Ser Ser
            660                 665                 670

Lys Leu Lys Glu Cys Cys Glu Lys Pro Leu Leu Glu Lys Ser His Cys
        675                 680                 685

Ile Ala Glu Val Glu Asn Asp Glu Met Pro Ala Asp Leu Pro Ser Leu
    690                 695                 700

Ala Ala Asp Phe Val Glu Ser Lys Asp Val Cys Lys Asn Tyr Ala Glu
705                 710                 715                 720

Ala Lys Asp Val Phe Leu Gly Met Phe Leu Tyr Glu Tyr Ala Arg Arg
                725                 730                 735

His Pro Asp Tyr Ser Val Val Leu Leu Leu Arg Leu Ala Lys Thr Tyr
            740                 745                 750

Glu Thr Thr Leu Glu Lys Cys Cys Ala Ala Ala Asp Pro His Glu Cys
        755                 760                 765

Tyr Ala Lys Val Phe Asp Glu Phe Lys Pro Leu Val Glu Glu Pro Gln
    770                 775                 780

Asn Leu Ile Lys Gln Asn Cys Glu Leu Phe Glu Gln Leu Gly Glu Tyr
785                 790                 795                 800

Lys Phe Gln Asn Ala Leu Leu Val Arg Tyr Thr Lys Lys Val Pro Gln
```

```
                805                 810                 815
Val Ser Thr Pro Thr Leu Val Glu Val Ser Arg Asn Leu Gly Lys Val
            820                 825                 830

Gly Ser Lys Cys Cys Lys His Pro Glu Ala Lys Arg Met Pro Cys Ala
        835                 840                 845

Glu Asp Tyr Leu Ser Val Val Leu Asn Gln Leu Cys Val Leu His Glu
    850                 855                 860

Lys Thr Pro Val Ser Asp Arg Val Thr Lys Cys Cys Thr Glu Ser Leu
865                 870                 875                 880

Val Asn Arg Arg Pro Cys Phe Ser Ala Leu Glu Val Asp Glu Thr Tyr
                885                 890                 895

Val Pro Lys Glu Phe Asn Ala Glu Thr Phe Thr Phe His Ala Asp Ile
            900                 905                 910

Cys Thr Leu Ser Glu Lys Glu Arg Gln Ile Lys Lys Gln Thr Ala Leu
        915                 920                 925

Val Glu Leu Val Lys His Lys Pro Lys Ala Thr Lys Glu Gln Leu Lys
    930                 935                 940

Ala Val Met Asp Asp Phe Ala Ala Phe Val Glu Lys Cys Cys Lys Ala
945                 950                 955                 960

Asp Asp Lys Glu Thr Cys Phe Ala Glu Glu Gly Lys Lys Leu Val Ala
                965                 970                 975

Ala Ser Gln Ala Ala Leu Gly Leu
            980

<210> SEQ ID NO 31
<211> LENGTH: 595
<212> TYPE: PRT
<213> ORGANISM: Artificial Sequence
<220> FEATURE:
<223> OTHER INFORMATION: AAT-HSA Domain 3 fusion protein

<400> SEQUENCE: 31

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
```

-continued

```
                180                 185                 190
Lys Trp Glu Arg Pro Phe Glu Val Lys Asp Thr Glu Glu Asp Phe
            195                 200                 205
His Val Asp Gln Val Thr Thr Val Lys Val Pro Met Met Lys Arg Leu
        210                 215                 220
Gly Met Phe Asn Ile Gln His Cys Lys Lys Leu Ser Ser Trp Val Leu
225                 230                 235                 240
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
        275                 280                 285
Pro Lys Leu Ser Ile Thr Gly Thr Tyr Asp Leu Lys Ser Val Leu Gly
        290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Glu Lys Gly Thr Glu Ala Ala Gly Ala Met Phe
                340                 345                 350
Leu Glu Ala Ile Pro Met Ser Ile Pro Pro Glu Val Lys Phe Asn Lys
            355                 360                 365
Pro Phe Val Phe Leu Met Ile Glu Gln Asn Thr Lys Ser Pro Leu Phe
        370                 375                 380
Met Gly Lys Val Val Asn Pro Thr Gln Lys Ala Ser Thr Gly Ser Glu
385                 390                 395                 400
Glu Pro Gln Asn Leu Ile Lys Gln Asn Cys Glu Leu Phe Glu Gln Leu
                405                 410                 415
Gly Glu Tyr Lys Phe Gln Asn Ala Leu Leu Val Arg Tyr Thr Lys Lys
            420                 425                 430
Val Pro Gln Val Ser Thr Pro Thr Leu Val Glu Val Ser Arg Asn Leu
        435                 440                 445
Gly Lys Val Gly Ser Lys Cys Cys Lys His Pro Glu Ala Lys Arg Met
        450                 455                 460
Pro Cys Ala Glu Asp Tyr Leu Ser Val Val Leu Asn Gln Leu Cys Val
465                 470                 475                 480
Leu His Glu Lys Thr Pro Val Ser Asp Arg Val Thr Lys Cys Cys Thr
                485                 490                 495
Glu Ser Leu Val Asn Arg Arg Pro Cys Phe Ser Ala Leu Glu Val Asp
                500                 505                 510
Glu Thr Tyr Val Pro Lys Glu Phe Asn Ala Glu Thr Phe Thr Phe His
            515                 520                 525
Ala Asp Ile Cys Thr Leu Ser Glu Lys Glu Arg Gln Ile Lys Lys Gln
        530                 535                 540
Thr Ala Leu Val Glu Leu Val Lys His Lys Pro Lys Ala Thr Lys Glu
545                 550                 555                 560
Gln Leu Lys Ala Val Met Asp Asp Phe Ala Ala Phe Val Glu Lys Cys
                565                 570                 575
Cys Lys Ala Asp Asp Lys Glu Thr Cys Phe Ala Glu Glu Gly Lys Lys
            580                 585                 590
Leu Val Ala
        595
```

<210> SEQ ID NO 32
<211> LENGTH: 25
<212> TYPE: PRT
<213> ORGANISM: Artificial Sequence
<220> FEATURE:
<223> OTHER INFORMATION: reactive site loop of a variant of the fusion
      alpha-1 antitrypsin polypeptide

<400> SEQUENCE: 32

```
Gly Thr Glu Ala Ala Gly Ala Glu Phe Leu Glu Ala Ile Pro Leu Ser
1               5                   10                  15

Ile Pro Pro Glu Val Lys Phe Asn Lys
            20                  25
```

<210> SEQ ID NO 33
<211> LENGTH: 25
<212> TYPE: PRT
<213> ORGANISM: Artificial Sequence
<220> FEATURE:
<223> OTHER INFORMATION: reactive site loop of a variant of the fusion
      alpha-1 antitrypsin polypeptide

<400> SEQUENCE: 33

```
Gly Thr Glu Ala Ala Gly Ala Leu Phe Leu Glu Ala Ile Pro Leu Ser
1               5                   10                  15

Ile Pro Pro Glu Val Lys Phe Asn Lys
            20                  25
```

<210> SEQ ID NO 34
<211> LENGTH: 394
<212> TYPE: PRT
<213> ORGANISM: Artificial Sequence
<220> FEATURE:
<223> OTHER INFORMATION: alpha-1 antitrypsin polypeptide portion of the
      AAT-MM-EL-hFc1 fusion protein

<400> SEQUENCE: 34

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175
```

```
Asp Arg Asp Thr Val Phe Ala Leu Val Asn Tyr Ile Phe Lys Gly
            180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
        260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Glu Phe
            340                 345                 350

Leu Glu Ala Ile Pro Leu Ser Ile Pro Pro Glu Val Lys Phe Asn Lys
            355                 360                 365

Pro Phe Val Phe Leu Met Ile Glu Gln Asn Thr Lys Ser Pro Leu Phe
        370                 375                 380

Met Gly Lys Val Val Asn Pro Thr Gln Lys
385                 390

<210> SEQ ID NO 35
<211> LENGTH: 394
<212> TYPE: PRT
<213> ORGANISM: Artificial Sequence
<220> FEATURE:
<223> OTHER INFORMATION: AAT polypeptide portion of the AAT-MM-LL-hFc1
      fusion protein

<400> SEQUENCE: 35

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
            85                  90                  95

Gln Glu Leu Leu Arg Thr Leu Asn Gln Pro Asp Ser Gln Leu Gln Leu
        100                 105                 110

Thr Thr Gly Asn Gly Leu Phe Leu Ser Glu Gly Leu Lys Leu Val Asp
    115                 120                 125

Lys Phe Leu Glu Asp Val Lys Lys Leu Tyr His Ser Glu Ala Phe Thr
        130                 135                 140
```

```
Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
            165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Asp Phe
            195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Leu Phe
            340                 345                 350

Leu Glu Ala Ile Pro Leu Ser Ile Pro Pro Glu Val Lys Phe Asn Lys
            355                 360                 365

Pro Phe Val Phe Leu Met Ile Glu Gln Asn Thr Lys Ser Pro Leu Phe
            370                 375                 380

Met Gly Lys Val Val Asn Pro Thr Gln Lys
385                 390

<210> SEQ ID NO 36
<211> LENGTH: 626
<212> TYPE: PRT
<213> ORGANISM: Artificial Sequence
<220> FEATURE:
<223> OTHER INFORMATION: AAT-MM-LL-hFc1 fusion protein

<400> SEQUENCE: 36

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
            85                  90                  95

Gln Glu Leu Leu Arg Thr Leu Asn Gln Pro Asp Ser Gln Leu Gln Leu
            100                 105                 110
```

```
Thr Thr Gly Asn Gly Leu Phe Leu Ser Glu Gly Leu Lys Leu Val Asp
        115                 120                 125
Lys Phe Leu Glu Asp Val Lys Lys Leu Tyr His Ser Glu Ala Phe Thr
130                 135                 140
Val Asn Phe Gly Asp Thr Glu Ala Lys Lys Gln Ile Asn Asp Tyr
145                 150                 155                 160
Val Glu Lys Gly Thr Gln Gly Lys Ile Val Asp Leu Val Lys Glu Leu
                165                 170                 175
Asp Arg Asp Thr Val Phe Ala Leu Val Asn Tyr Ile Phe Phe Lys Gly
                180                 185                 190
Lys Trp Glu Arg Pro Phe Glu Val Lys Asp Thr Glu Glu Glu Asp Phe
            195                 200                 205
His Val Asp Gln Val Thr Thr Val Lys Val Pro Met Met Lys Arg Leu
        210                 215                 220
Gly Met Phe Asn Ile Gln His Cys Lys Lys Leu Ser Ser Trp Val Leu
225                 230                 235                 240
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
        275                 280                 285
Pro Lys Leu Ser Ile Thr Gly Thr Tyr Asp Leu Lys Ser Val Leu Gly
290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Glu Lys Gly Thr Glu Ala Ala Gly Ala Leu Phe
                340                 345                 350
Leu Glu Ala Ile Pro Leu Ser Ile Pro Pro Glu Val Lys Phe Asn Lys
            355                 360                 365
Pro Phe Val Phe Leu Met Ile Glu Gln Asn Thr Lys Ser Pro Leu Phe
        370                 375                 380
Met Gly Lys Val Val Asn Pro Thr Gln Lys Glu Pro Lys Ser Cys Asp
385                 390                 395                 400
Lys Thr His Thr Cys Pro Pro Cys Pro Ala Pro Glu Leu Leu Gly Gly
                405                 410                 415
Pro Ser Val Phe Leu Phe Pro Pro Lys Pro Lys Asp Thr Leu Met Ile
            420                 425                 430
Ser Arg Thr Pro Glu Val Thr Cys Val Val Val Asp Val Ser His Glu
        435                 440                 445
Asp Pro Glu Val Lys Phe Asn Trp Tyr Val Asp Gly Val Glu Val His
    450                 455                 460
Asn Ala Lys Thr Lys Pro Arg Glu Glu Gln Tyr Asn Ser Thr Tyr Arg
465                 470                 475                 480
Val Val Ser Val Leu Thr Val Leu His Gln Asp Trp Leu Asn Gly Lys
                485                 490                 495
Glu Tyr Lys Cys Lys Val Ser Asn Lys Ala Leu Pro Ala Pro Ile Glu
            500                 505                 510
Lys Thr Ile Ser Lys Ala Lys Gly Gln Pro Arg Glu Pro Gln Val Tyr
        515                 520                 525
```

```
Thr Leu Pro Pro Ser Arg Asp Glu Leu Thr Lys Asn Gln Val Ser Leu
            530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
                565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
            595                 600                 605

Glu Ala Leu His Asn His Tyr Thr Gln Lys Ser Leu Ser Leu Ser Pro
610                 615                 620

Gly Lys
625

<210> SEQ ID NO 37
<211> LENGTH: 107
<212> TYPE: PRT
<213> ORGANISM: Artificial Sequence
<220> FEATURE:
<223> OTHER INFORMATION: D2E7-VK portion of a fusion protein

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: antibody constant region of a fusion protein

<400> SEQUENCE: 38

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95
```

```
Pro Val Thr Lys Ser Phe Asn Arg Gly Glu Cys
            100                 105

<210> SEQ ID NO 39
<211> LENGTH: 116
<212> TYPE: PRT
<213> ORGANISM: Artificial Sequence
<220> FEATURE:
<223> OTHER INFORMATION: D2E7-VH portion of a fusion protein

<400> SEQUENCE: 39

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu
        115

<210> SEQ ID NO 40
<211> LENGTH: 335
<212> TYPE: PRT
<213> ORGANISM: Artificial Sequence
<220> FEATURE:
<223> OTHER INFORMATION: antibody constant region of a fusion protein

<400> SEQUENCE: 40

Val Thr Val Ser Ser Ala Ser Thr Lys Gly Pro Ser Val Phe Pro Leu
1               5                   10                  15

Ala Pro Ser Ser Lys Ser Thr Ser Gly Gly Thr Ala Ala Leu Gly Cys
            20                  25                  30

Leu Val Lys Asp Tyr Phe Pro Glu Pro Val Thr Val Ser Trp Asn Ser
        35                  40                  45

Gly Ala Leu Thr Ser Gly Val His Thr Phe Pro Ala Val Leu Gln Ser
    50                  55                  60

Ser Gly Leu Tyr Ser Leu Ser Ser Val Val Thr Val Pro Ser Ser Ser
65                  70                  75                  80

Leu Gly Thr Gln Thr Tyr Ile Cys Asn Val Asn His Lys Pro Ser Asn
                85                  90                  95

Thr Lys Val Asp Lys Lys Val Glu Pro Lys Ser Cys Asp Lys Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
```

```
                165                 170                 175
Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 41
<211> LENGTH: 235
<212> TYPE: PRT
<213> ORGANISM: Artificial Sequence
<220> FEATURE:
<223> OTHER INFORMATION: TNFR2-ECD portion of a fusion protein

<400> SEQUENCE: 41

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
```

```
                195                 200                 205
Pro Glu Pro Ser Thr Ala Pro Ser Thr Ser Phe Leu Leu Pro Met Gly
            210                 215                 220

Pro Ser Pro Pro Ala Glu Gly Ser Thr Gly Asp
225                 230                 235

<210> SEQ ID NO 42
<211> LENGTH: 232
<212> TYPE: PRT
<213> ORGANISM: Artificial Sequence
<220> FEATURE:
<223> OTHER INFORMATION: antibody constant region of a fusion protein

<400> SEQUENCE: 42

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Gln Val Lys Phe Asn Trp Tyr Val
50                  55                  60

Asp Gly Val Gln Val His Asn Ala Lys Thr Lys Pro Arg Glu Gln Gln
65                  70                  75                  80

Tyr Asn Ser Thr Tyr Arg Val Val Ser Val Leu Thr Val Leu His Gln
                85                  90                  95

Asn Trp Leu Asp Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 43
<211> LENGTH: 15
<212> TYPE: PRT
<213> ORGANISM: Artificial Sequence
<220> FEATURE:
<223> OTHER INFORMATION: hinge region

<400> SEQUENCE: 43

Glu Pro Lys Ser Cys Asp Lys Thr His Thr Cys Pro Pro Cys Pro
1               5                   10                  15

<210> SEQ ID NO 44
<211> LENGTH: 12
```

```
<212> TYPE: PRT
<213> ORGANISM: Artificial Sequence
<220> FEATURE:
<223> OTHER INFORMATION: hinge region

<400> SEQUENCE: 44

Glu Arg Lys Cys Cys Val Glu Cys Pro Pro Cys Pro
1               5                   10

<210> SEQ ID NO 45
<211> LENGTH: 5
<212> TYPE: PRT
<213> ORGANISM: Artificial Sequence
<220> FEATURE:
<223> OTHER INFORMATION: ASTGS linker

<400> SEQUENCE: 45

Ala Ser Thr Gly Ser
1               5

<210> SEQ ID NO 46
<211> LENGTH: 8
<212> TYPE: PRT
<213> ORGANISM: Artificial Sequence
<220> FEATURE:
<223> OTHER INFORMATION: (G3S)2 linker

<400> SEQUENCE: 46

Gly Gly Gly Ser Gly Gly Gly Ser
1               5
```

SERPIN FUSION POLYPEPTIDES AND METHODS OF USE THEREOF

RELATED APPLICATIONS

This application is a continuation of U.S. application Ser. No. 16/393,619, filed Apr. 24, 2019, which is a continuation of U.S. application Ser. No. 15/875,010, filed Jan. 19, 2018, now U.S. Pat. No. 10,723,785, issued Jul. 28, 2020 which is a continuation of U.S. application Ser. No. 14/616,363, filed Feb. 6, 2015, now U.S. Pat. No. 10,730,929, issued Aug. 4, 2020, which is a continuation of U.S. application Ser. No. 13/536,976, filed Jun. 28, 2012, now U.S. Pat. No. 8,980,266, issued Mar. 17, 2015, which claims the benefit of U.S. Provisional Application No. 61/502,055, filed Jun. 28, 2011; U.S. Provisional Application No. 61/570,394, filed Dec. 14, 2011; and U.S. Provisional Application No. 61/577,204, filed Dec. 19, 2011; and U.S. Provisional Application No. 61/638,168, filed Apr. 25, 2012. The contents of each of these applications are hereby incorporated by reference in their entirety.

INCORPORATION-BY-REFERENCE OF SEQUENCE LISTING

The contents of the text file named "INHI002C05US_SeqList.txt", which was created on Oct. 8, 2020 and is 150 KB in size, are hereby incorporated by reference in their entirety.

FIELD OF THE INVENTION

This invention relates to molecules, particularly polypeptides, more particularly fusion proteins that include a serpin polypeptide or an amino acid sequence that is derived from a serpin polypeptides and a second polypeptide. Additionally, the invention relates to fusion proteins that include a serpin polypeptide or an amino acid sequence that is derived from serpin polypeptides, a second polypeptide, and a third polypeptide. Specifically, this invention relates to fusion proteins that include at least one serpin polypeptide and a second polypeptide or fusion proteins that include at least one serpin polypeptide, a second polypeptide, and a third polypeptide, where the second and third polypeptides of the fusion proteins of the invention can be at least one the following: an Fc polypeptide or an amino acid sequence that is derived from an Fc polypeptide; a cytokine targeting polypeptide or a sequence derived from a cytokine targeting polypeptide; a WAP domain containing polypeptide or a sequence derived from a WAP containing polypeptide; or an albumin polypeptide or an amino acid sequence that is derived from a serum albumin polypeptide. This invention also relates to methods of using such molecules in a variety of therapeutic and diagnostic indications, as well as methods of producing such molecules.

BACKGROUND OF THE INVENTION

Aberrant serine protease activity or an imbalance of protease-to-protease inhibitor can lead to protease-mediated tissue destruction and inflammatory responses. Accordingly, there exists a need for therapeutics and therapies that target aberrant serine protease activity and/or imbalance of protease-to-protease inhibitor. Furthermore, enhanced therapeutic effects may be gained through the attenuation of aberrant cytokine signaling and serine protease activity. In addition, serpin proteins have demonstrated anti-infective activities while targeting inflammatory cytokines has been shown to increase the risk of infection. The fusion proteins of this invention have the potential to dampen inflammatory cytokine activity and limit the risk of infection.

SUMMARY OF THE INVENTION

The fusion proteins described herein include at least a serpin polypeptide or an amino acid sequence that is derived from a serpin polypeptide (Polypeptide 1) and second polypeptide (Polypeptide 2). Additionally, the fusion proteins described herein include a serpin polypeptide or an amino acid sequence that is derived from a serpin polypeptide (Polypeptide 1), a second polypeptide (Polypeptide 2), and a third polypeptide (Polypeptide 3). As used interchangeably herein, the terms "fusion protein" and "fusion polypeptide" refer to a serpin polypeptide or an amino acid sequence derived from a serpin polypeptide operably linked to at least a second polypeptide or an amino acid sequence derived from at least a second polypeptide. The individualized elements of the fusion protein can be linked in any of a variety of ways, including for example, direct attachment, the use of an intermediate or a spacer peptide, the use of a linker region, the use of a hinge region or the use of both a linker and a hinge region. In some embodiments, the linker region may fall within the sequence of the hinge region, or alternatively, the hinge region may fall within the sequence of the linker region. Preferably, the linker region is a peptide sequence. For example, the linker peptide includes anywhere from zero to 40 amino acids, e.g., from zero to 35 amino acids, from zero to 30 amino acids, from zero to 25 amino acids, or from zero to 20 amino acids. Preferably, the hinge region is a peptide sequence. For example, the hinge peptide includes anywhere from zero to 75 amino acids, e.g., from zero to 70 amino acids, from zero to 65 amino acids or from zero to 62 amino acids. In embodiments where the fusion protein includes both a linker region and hinge region, preferably each of the linker region and the hinge region is a peptide sequence. In these embodiments, the hinge peptide and the linker peptide together include anywhere from zero to 90 amino acids, e.g., from zero to 85 amino acids or from zero to 82 amino acids.

In some embodiments, the serpin polypeptide and the second polypeptide can be linked through an intermediate binding protein. In some embodiments, the serpin-based portion and second polypeptide portion of the fusion protein may be non-covalently linked.

In some embodiments, fusion proteins according to the invention can have one of the following formulae, in an N-terminus to C-terminus direction or in a C-terminus to N-terminus direction:

Polypeptide $1_{(a)}$-hinge$_m$-Polypeptide $2_{(b)}$
Polypeptide $1_{(a)}$-linker$_n$-Polypeptide $2_{(b)}$
Polypeptide $1_{(a)}$-linker$_n$-hinge$_m$-Polypeptide $2_{(b)}$
Polypeptide $1_{(a)}$-hinge$_m$-linker$_n$-Polypeptide $2_{(b)}$
Polypeptide $1_{(a)}$-Polypeptide $2_{(b)}$-Polypeptide $3_{(c)}$
Polypeptide $1_{(a)}$-hinge$_m$-Polypeptide $2_{(b)}$-hinge$_m$-Polypeptide $3_{(c)}$
Polypeptide $1_{(a)}$-linker$_n$-Polypeptide $2_{(b)}$-linker$_n$-Polypeptide $3_{(c)}$
Polypeptide $1_{(a)}$-hinge$_m$-linker$_n$-Polypeptide $2_{(b)}$-hinge$_m$-linker$_n$-Polypeptide $3_{(c)}$
Polypeptide $1_{(a)}$-linker$_n$-hinge$_m$-Polypeptide $2_{(b)}$-linker$_n$-hinge$_m$-Polypeptide $3_{(c)}$ where n is an integer from zero to 20, where m is an integer from 1 to 62 and where a, b, and c integers of at least 1. These embodiments include the above formulations and any variation or combination thereof. For example, the order of polypeptides in the formulae also includes Polypeptide $3_{(c)}$-Polypeptide $1_{(a)}$-Polypeptide $2_{(b)}$, Polypeptide $2_{(b)}$-Polypeptide $3_{(c)}$-Polypeptide $1_{(a)}$, or any variation or combination thereof.

In some embodiments, the Polypeptide 1 sequence includes a serpin polypeptide. Serpins are a group of proteins with similar structures that were first identified as a set of proteins able to inhibit proteases. Serpin proteins suitable for use in the fusion proteins provided herein include, by way of non-limiting example, alpha-1 antitrypsin (AAT), antitrypsin-related protein (SERPINA2), alpha 1-antichymotrypsin (SERPINA3), kallistatin (SERPINA4), monocyte neutrophil elastase inhibitor (SERPINB1), PI-6 (SERPINB6), antithrombin (SERPINC1), plasminogen activator inhibitor 1 (SERPINE1), alpha 2-antiplasmin (SERPINF2), complement 1-inhibitor (SERPING1), and neuroserpin (SERPINI1).

In some embodiments, the Polypeptide 1 sequence includes an alpha-1 antitrypsin (AAT) polypeptide sequence or an amino acid sequence that is derived from AAT. In some embodiments, the Polypeptide 1 sequence includes a portion of the AAT protein. In some embodiments, the Polypeptide 1 sequence includes at least the reactive site loop portion of the AAT protein. In some embodiments, the reactive site loop portion of the AAT protein includes at least the amino acid sequence: GTEAAGAMFLEAIPMSIPPEVKFNK SEQ ID NO: 1).

In a preferred embodiment, the AAT polypeptide sequence or an amino acid sequence that is derived from AAT is or is derived from a human AAT polypeptide sequence.

In some embodiments, the fusion protein includes a full-length human AAT polypeptide sequence having the following amino acid sequence:

least one mutation at a methionine (Met) residue in the serpin portion of the fusion protein. In these Met mutations, the Met residue can be substituted with any amino acid. For example, the Met residue can be substituted with an amino acid with a hydrophobic side chain, such as, for example, leucine (Leu, L). Without wishing to be bound by theory, the Met mutation(s) prevent oxidation and subsequent inactivation of the inhibitory activity of the fusion proteins of the invention. In some embodiments, the Met residue can be substituted with a charged residue, such as, for example, glutamate (Glu, E). In some embodiments, the Met mutation is at position 358 of an AAT polypeptide. For example, the Met mutation is Met358Leu (M358L). In some embodiments, the Met mutation is at position 351 of an AAT polypeptide. For example, the Met mutation is Met351Glu (M351E). In some embodiments, the Met mutation is at position 351 and at position 358 of an AAT polypeptide, for example, the Met mutation is Met351Glu (M351E) and Met358Leu (M358L). For example, the reactive site loop of this variant of the fusion AAT polypeptide has the following sequence: GTEAAGAEFLEAIPLSIPPEVKFNK (SEQ ID NO: 32). In some embodiments, the Met mutation is at position 351 and at position 358 of an AAT polypeptide, for example, the Met mutation is Met351Leu (M351L) and Met358Leu (M358L). For example, the reactive site loop of this variant of the fusion AAT polypeptide has the following sequence:

```
                                              (SEQ ID NO: 33)
               GTEAAGALFLEAIPLSIPPEVKFNK.
```

In some embodiments, the second polypeptide (Polypeptide 2) of the serpin fusion protein is an Fc polypeptide or derived from an Fc polypeptide. These embodiments are

```
                                                        (SEQ ID NO: 2)
  1  EDPQGDAAQK  TDTSHHDQDH  PTFNKITPNL  AEFAFSLYRQ  LAHQSNSTNI  FFSPVSIATA

61  FAMLSLGTKA  DTHDEILEGL  NFNLTEIPEA  QIHEGFQELL  RTLNQPDSQL  QLTTGNGLFL

121  SEGLKLVDKF  LEDVKKLYHS  EAFTVNFGDT  EEAKKQINDY  VEKGTQGKIV  DLVKELDRDT

181  VFALVNYIFF  KGKWERPFEV  KDTEEEDFHV  DQVTTVKVPM  MKRLGMFNIQ  HCKKLSSWVL

241  LMKYLGNATA  IFFLPDEGKL  QHLENELTHD  IITKFLENED  RRSASLHLPK  LSITGTYDLK

301  SVLGQLGITK  VFSNGADLSG  VTEEAPLKLS  KAVHKAVLTI  DEKGTEAAGA  MFLEAIPMSI

361  PPEVKFNKPF  VFLMIEQNTK  SPLFMGKVVN  PTQK
```

In some embodiments, the fusion protein includes a human AAT polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 2.

In some embodiments, the AAT polypeptide sequence is, or the amino acid sequence derived from an AAT polypeptide is derived from, one or more of the human AAT polypeptide sequences shown in GenBank Accession Nos. AAB59495.1, CAJ15161.1, P01009.3, AAB59375.1, AAA51546.1, CAA25838.1, NP_001002235.1, CAA34982.1, NP_001002236.1, NP_000286.3, NP_001121179.1, NP_001121178.1, NP_001121177.1, NP_001121176.16, NP_001121175.1, NP_001121174.1, NP_001121172.1, and/or AAA51547.1.

In some embodiments, the fusion proteins contain one or more mutations. For example, the fusion protein contains at referred to collectively herein as "serpin-Fc fusion proteins." The serpin-Fc fusion proteins described herein include at least a serpin polypeptide or an amino acid sequence that is derived from a serpin and an Fc polypeptide or an amino acid sequence that is derived from an Fc polypeptide. In some embodiments, the serpin-Fc fusion protein includes a single serpin polypeptide. In other embodiments, the serpin-Fc fusion proteins includes more than one serpin polypeptide, and these embodiments are collectively referred to herein as "serpin$_{(a')}$-Fc fusion protein," wherein (a') is an integer of at least 2. In some embodiments, each serpin polypeptides in a serpin$_{(a')}$-Fc fusion protein includes the same amino acid sequence. In other embodiments, each serpin polypeptide in a serpin$_{(a')}$-Fc fusion protein includes serpin polypeptides with distinct amino acid sequences. The serpin polypeptides of serpin$_{(a')}$-Fc fusion proteins can be located at any position within the fusion protein.

In some embodiments, the serpin polypeptide of the serpin-Fc fusion protein includes at least the amino acid sequence of the reactive site loop portion of the AAT protein. In some embodiments, the reactive site loop portion of the AAT protein includes at least the amino acid sequence of SEQ ID NO:1. In some embodiments, the serpin polypeptide of the serpin-Fc fusion protein includes at least the amino acid sequence of a variant of the reactive site loop portion of the AAT protein. In some embodiments, the variant of the reactive site loop portion of the AAT protein includes at least the amino acid sequence of SEQ ID NO:32 or SEQ ID NO:33. In some embodiments, the serpin polypeptide of the serpin-Fc fusion protein includes at least the full-length human AAT polypeptide sequence having amino acid sequence of SEQ ID NO: 2. In some embodiments the serpin polypeptide of the serpin-Fc fusion protein includes human AAT polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 2 or 32 or 33.

In some embodiments, the serpin polypeptide of the serpin-Fc fusion protein includes the AAT polypeptide sequence is or the amino acid sequence derived from an AAT polypeptide is derived from one or more of the human AAT polypeptide sequences shown in GenBank Accession Nos. AAB59495.1, CAJ15161.1, P01009.3, AAB59375.1, AAA51546.1, CAA25838.1, NP_001002235.1, CAA34982.1, NP_001002236.1, NP_000286.3, NP_001121179.1, NP_001121178.1, NP_001121177.1, NP_001121176.16, NP_001121175.1, NP_001121174.1, NP_001121172.1, and/or AAA51547.1.

In some embodiments, the Fc polypeptide of the fusion protein is a human Fc polypeptide, for example, a human IgG Fc polypeptide sequence or an amino acid sequence that is derived from a human IgG Fc polypeptide sequence. For example, in some embodiments, the Fc polypeptide is a human IgG1 Fc polypeptide or an amino acid sequence that is derived from a human IgG1 Fc polypeptide sequence. In some embodiments, the Fc polypeptide is a human IgG2 Fc polypeptide or an amino acid sequence that is derived from a human IgG2 Fc polypeptide sequence. In some embodiments, the Fc polypeptide is a human IgG3 Fc polypeptide or an amino acid sequence that is derived from a human IgG3 Fc polypeptide sequence. In some embodiments, the Fc polypeptide is a human IgG4 Fc polypeptide or an amino acid sequence that is derived from a human IgG4 Fc polypeptide sequence. In some embodiments, the Fc polypeptide is a human IgM Fc polypeptide or an amino acid sequence that is derived from a human IgM Fc polypeptide sequence.

In some embodiments where the fusion protein of the invention includes an Fc polypeptide, the Fc polypeptide of the fusion protein includes a human IgG1 Fc polypeptide sequence having the following amino acid sequence:

```
                                                          (SEQ ID NO: 3)
  1 APELLGGPSV FLFPPKPKDT LMISRTPEVT CVVVDVSHED PEVKFNWYVD GVEVHNAKTK
 61 PREEQYNSTY RVVSVLTVLH QDWLNGKEYK CKVSNKALPA PIEKTISKAK GQPREPQVYT
121 LPPSRDELTK NQVSLTCLVK GFYPSDIAVE WESNGQPENN YKTTPPVLDS DGSFFLYSKL
181 TVDKSRWQQG NVFSCSVMHE ALHNHYTQKS LSLSPGK
```

In some embodiments where the fusion protein of the invention includes an Fc polypeptide, the Fc polypeptide of the fusion protein includes a human IgG1 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 3.

In some embodiments where the fusion protein of the invention includes an Fc polypeptide, the Fc polypeptide is mutated or modified to enhance FcRn binding. In these embodiments the mutated or modified Fc polypeptide includes the following mutations: Met252Tyr, Ser254Thr, Thr256Glu (M252Y, S256T, T256E) or Met428Leu and Asn434Ser (M428L, N434S) using the Kabat numbering system. In some embodiments the Fc polypeptide portion is mutated or otherwise modified so as to disrupt Fc-mediated dimerization. In these embodiments, the fusion protein is monomeric in nature.

In some embodiments where the fusion protein of the invention includes an Fc polypeptide, the Fc polypeptide of the fusion protein includes a human IgG2 Fc polypeptide sequence having the following amino acid sequence:

```
                                                          (SEQ ID NO: 4)
  1 APPVAGPSVF LFPPKPKDTL MISRTPEVTC VVVDVSHEDP EVQFNWYVDG VEVHNAKTKP
 61 REEQFNSTFR VVSVLTVVHQ DWLNGKEYKC KVSNKGLPAP IEKTISKTKG QPREPQVYTL
121 PPSREEMTKN QVSLTCLVKG FYPSDIAVEW ESNGQPENNY KTTPPMLDSD GSFFLYSKLT
181 VDKSRWQQGN VFSCSVMHEA LHNHYTQKSL SLSPGK
```

In some embodiments where the fusion protein of the invention includes an Fc polypeptide, the Fc polypeptide of the fusion protein includes a human IgG2 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 4.

In some embodiments where the fusion protein of the invention includes an Fc polypeptide, the Fc polypeptide of the fusion protein includes a human IgG3 Fc polypeptide sequence having the following amino acid sequence:

```
                                                              (SEQ ID NO: 5)
  1  APELLGGPSV  FLFPPKPKDT  LMISRTPEVT  CVVVDVSHED  PEVQFKWYVD  GVEVHNAKTK

61  PREEQYNSTF  RVVSVLTVLH  QDWLNGKEYK  CKVSNKALPA  PIEKTISKTK  GQPREPQVYT

121  LPPSREEMTK  NQVSLTCLVK  GFYPSDIAVE  WESSGQPENN  YNTTPPMLDS  DGSFFLYSKL

181  TVDKSRWQQG  NIFSCSVMHE  ALHNRFTQKS  LSLSPGK
```

In some embodiments where the fusion protein of the invention includes an Fc polypeptide, the Fc polypeptide of the fusion protein includes a human IgG3 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 5.

In some embodiments where the fusion protein of the invention includes an Fc polypeptide, the Fc polypeptide of the fusion protein includes a human IgG4 Fc polypeptide sequence having the following amino acid sequence:

```
                                                              (SEQ ID NO: 6)
  1  APEFLGGPSV  FLFPPKPKDT  LMISRTPEVT  CVVVDVSQED  PEVQFNWYVD  GVEVHNAKTK

61  PREEQFNSTY  RVVSVLTVLH  QDWLNGKEYK  CKVSNKGLPS  SIEKTISKAK  GQPREPQVYT

121  LPPSQEEMTK  NQVSLTCLVK  GFYPDIAVEW  ESNGQPENNY  KTTPPVLDSD  GSFFLYSRLT

181  VDKSRWQEGN  VFSCSVMHEA  LHNHYTQKSL  SLSLGK
```

In some embodiments where the fusion protein of the invention includes an Fc polypeptide, the Fc polypeptide of the fusion protein includes a human IgG4 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 6.

In some embodiments where the fusion protein of the invention includes an Fc polypeptide, the Fc polypeptide of the fusion protein includes a human IgM Fc polypeptide sequence having the following amino acid sequence:

```
                                                              (SEQ ID NO: 7)
  1  IAELPPKVSV  FVPPRDGFFG  NPRKSKLICQ  ATGFSPRQIQ  VSWLREGKQV  GSGVTTDQVQ

61  AEAKESGPTT  YKVTSTLTIK  ESDWLGQSMF  TCRVDHRGLT  FQQNASSMCV  PDQDTAIRVF

121  AIPPSFASIF  LTKSTKLTCL  VTDLTTYDSV  TISWTRQNGE  AVKTHTNISE  SHPNATFSAV

181  GEASICEDDW  NSGERFTCTV  THTDLPSPLK  QTISRPKG
```

In some embodiments where the fusion protein of the invention includes an Fc polypeptide, the Fc polypeptide of the fusion protein includes a human IgM Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 7.

In some embodiments of the fusion proteins provided herein, the second polypeptide (Polypeptide 2) of the serpin fusion protein is a cytokine targeting polypeptide or derived from a cytokine targeting polypeptide. These embodiments are referred to collectively herein as "serpin-cytokine targeting polypeptide fusion proteins." The serpin-cytokine targeting polypeptide fusion proteins described herein include at least a serpin polypeptide or an amino acid sequence that is derived from a serpin polypeptide and a cytokine targeting polypeptide, or derivation thereof. In some embodiments, the serpin-cytokine targeting polypeptide fusion protein includes a single serpin polypeptide. In other embodiments, the serpin-cytokine targeting polypeptide fusion protein includes more than one serpin polypeptide, and these embodiments are collectively referred to herein as "serpin$_{(a')}$-cytokine targeting polypeptide fusion proteins," wherein (a') is an integer of at least 2. In some embodiments, each serpin polypeptide in a serpin$_{(a')}$-cytokine targeting polypeptide fusion protein includes the same amino acid sequence. In other embodiments, each serpin polypeptide of a serpin$_{(a')}$-cytokine targeting polypeptide fusion protein includes serpin polypeptides with distinct amino acid sequences.

In some embodiments, the cytokine targeting polypeptide of the serpin-cytokine targeting polypeptide fusion protein is a cytokine receptor or derived from a cytokine receptor. In a preferred embodiment, the cytokine targeting polypeptide or an amino acid sequence that is derived from the cytokine receptor is or is derived from a human cytokine receptor sequence. In other embodiments, the cytokine targeting polypeptide is an antibody or an antibody fragment, for example an anti-cytokine antibody or anti-cytokine antibody fragment. In a preferred embodiment, the cytokine targeting polypeptide or an amino acid sequence that is derived from the antibody or antibody fragment is derived from a chimeric, humanized, or fully human antibody sequence. The term antibody fragment includes single chain, Fab fragment, a F(ab')$_2$ fragment, a scFv, a scAb, a dAb, a single domain heavy chain antibody, and a single domain light chain antibody.

In other embodiments, the cytokine targeting polypeptide binds a cytokine receptor and prevents binding of a cytokine to the receptor. In other embodiments, the cytokine targeting polypeptide is an antibody or an antibody fragment, for example an anti-cytokine receptor antibody or anti-cytokine receptor antibody fragment.

In some embodiments, the serpin polypeptide of the serpin-cytokine targeting polypeptide fusion proteins includes at least the amino acid sequence of the reactive site loop portion of the AAT protein. In some embodiments, the reactive site loop portion of the AAT protein includes at least the amino acid sequence of SEQ ID NO:1. In some embodiments, the serpin polypeptide of the serpin-cytokine targeting fusion proteins includes at least the amino acid sequence of a variant of the reactive site loop portion of the AAT protein. In some embodiments, the variant of the reactive site loop portion of the AAT protein includes at least the amino acid sequence of SEQ ID NO:32 or SEQ ID NO:33. In some embodiments, the serpin polypeptide of the serpin-cytokine targeting fusion protein includes or is derived from at least the full-length human AAT polypeptide sequence having amino acid sequence of SEQ ID NO: 2. In some embodiments the serpin polypeptide of the serpin-cytokine targeting fusion protein includes human AAT polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 2 or 32 or 33.

In some embodiments, the serpin polypeptide of the serpin-cytokine targeting fusion protein includes an AAT polypeptide sequence or an amino acid sequence derived from an AAT polypeptide that is or is derived from one or more of the human AAT polypeptide sequences shown in GenBank Accession Nos. AAB59495.1, CAJ15161.1, P01009.3, AAB59375.1, AAA51546.1, CAA25838.1, NP 001002235.1, CAA34982.1, NP_001002236.1, NP_000286.3, NP_001121179.1, NP_001121178.1, NP_001121177.1, NP_001121176.16, NP_001121175.1, NP_001121174.1, NP_001121172.1, and/or AAA51547.1.

The serpin-cytokine targeting polypeptide fusion protein can incorporate a portion of the serpin-Fc fusion protein. For example, an antibody contains an Fc polypeptide. Therefore, in some embodiments where the cytokine targeting polypeptide is a cytokine-targeting antibody, the serpin-cytokine targeting polypeptide fusion protein will incorporate a portion of the serpin-Fc fusion protein. Furthermore, most receptor fusion proteins that are of therapeutic utility are Fc fusion proteins. Thus, in some embodiments, wherein the serpin-cytokine targeting polypeptide fusion protein is a serpin-cytokine receptor fusion protein, the serpin-cytokine targeting polypeptide fusion protein may incorporate an Fc polypeptide in addition to the serpin portion and the cytokine receptor portion.

In some embodiments, where the serpin-cytokine targeting polypeptide fusion protein includes an Fc polypeptide sequence, the Fc polypeptide sequence includes or is derived from the amino acid sequence of any one of SEQ ID NO: 3, 4, 5, 6, or 7. In some embodiments where the serpin-cytokine targeting fusion protein includes an Fc polypeptide sequence, the Fc polypeptide sequence has at least 50%, 60%, 65%, 70%, 75%, 80%, 85%, 90%, 91%, 92%, 93%, 94%, 95%, 96%, 97%, 98% or 99% identity to any one of the amino acid sequence of SEQ ID NO: 3, 4, 5, 6, or 7. In some embodiments, the serpin polypeptide and the cytokine targeting polypeptide are operably linked via a linker region, for example, a glycine-serine linker or glycine-serine based linker. In some embodiments, the serpin polypeptide and the cytokine targeting polypeptide are operably linked via a hinge region. In some embodiments, the serpin polypeptide and the cytokine targeting polypeptide are operably linked via a linker region and a hinge region. In other embodiments, the serpin polypeptide and the cytokine targeting polypeptide are directly attached.

In some embodiments of the fusion proteins provided herein, the second polypeptide (Polypeptide 2) of the serpin fusion protein is a whey acidic protein (WAP) domain containing polypeptide, or an amino acid sequence that is derived from a WAP domain containing polypeptide. These embodiments are referred to collectively herein as "serpin-WAP domain fusion proteins." The serpin-WAP domain fusion proteins include at least a serpin polypeptide or at least an amino acid sequence that is derived from a serpin, a WAP domain-containing polypeptide or an amino acid sequence that is derived from a WAP domain-containing polypeptide. In some embodiments, the serpin-WAP domain fusion protein includes a single serpin polypeptide. In other embodiments, the serpin-WAP targeting polypeptide fusion protein includes more than one serpin polypeptide. These embodiments are collectively referred to herein as "serpin$_{(a')}$-WAP domain fusion proteins," wherein (a') is an integer of at least 2. In some embodiments, serpin polypeptides of the serpin$_{(a')}$-WAP domain fusion protein includes the same amino acid sequence. In other embodiments, the serpin polypeptides of the serpin$_{(a')}$-cytokine targeting polypeptide fusion protein, includes serpin polypeptides with distinct amino acid sequences.

These serpin-WAP domain fusion proteins include a WAP domain containing polypeptide or polypeptide sequence that is or is derived from a WAP domain containing polypeptide. The WAP domain is an evolutionarily conserved sequence motif of 50 amino acids containing eight cysteines found in a characteristic 4-disulfide core arrangement (also called a four-disulfide core motif). The WAP domain sequence motif is a functional motif characterized by serine protease inhibition activity in a number of proteins.

WAP domain-containing polypeptides suitable for use in the fusion proteins provided herein include, by way of non-limiting example, secretory leukocyte protease inhibitor (SLPI), Elafin, and Eppin.

In some embodiments, the WAP domain-containing polypeptide sequence of the fusion protein includes a secretory leukocyte protease inhibitor (SLPI) polypeptide sequence or an amino acid sequence that is derived from SLPI. These embodiments are referred to herein as "serpin-SLPI-derived fusion proteins." In some embodiments, the SLPI polypeptide sequence comprises a portion of the SLPI protein, such as for example, the WAP2 domain or a sub-portion thereof. In a preferred embodiment, the SLPI polypeptide sequence or an amino acid sequence that is derived from SLPI is or is derived from a human SLPI polypeptide sequence.

In some embodiments of the serpin-SLPI fusion proteins of the invention, the SLPI sequence or a SLPI-derived sequence of the fusion protein includes a full-length human SLPI polypeptide sequence having the following amino acid sequence:

(SEQ ID NO: 8)
```
  1 MKSSGLFPFL VLLALGTLAP WAVEGSGKSF KAGVCPPKKS AQCLRYKKPE CQSDWQCPGK
 61 KRCCPDTCGI KCLDPVDTPN PTRRKPGKCP VTYGQCLMLN PPNFCEMDGQ CKRDLKCCMG
121 MCGKSCVSPV KA
```

In some embodiments of the serpin-SLPI fusion protein of the invention, the SLPI sequence or a SLPI-derived sequence of the fusion protein includes a human SLPI polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 8.

In some embodiments of the serpin-SLPI fusion protein of the invention, the SLPI sequence or a SLPI-derived sequence of the fusion protein includes a portion of the full-length human SLPI polypeptide sequence, where the portion has the following amino acid sequence:

(SEQ ID NO: 9)
1 SGKSFKAGVC PPKKSAQCLR YKKPECQSDW QCPGKKRCCP DTCGIKCLDP VDTPNPTRRK
61 PGKCPVTYGQ CLMLNPPNFC EMDGQCKRDL KCCMGMCGKS CVSPVKA

In some embodiments of the serpin-SLPI fusion protein of the invention, the SLPI sequence or a SLPI-derived sequence of the fusion protein includes a human SLPI polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 9.

In some embodiments of the serpin-SLPI fusion protein of the invention, the SLPI sequence or a SLPI-derived sequence of the fusion protein includes the WAP2 domain of the full-length human SLPI polypeptide sequence, where the WAP2 domain has the following amino acid sequence:

(SEQ ID NO: 10)
1 TRRKPGKCPV TYGQCLMLNP PNFCEMDGQC KRDLKCCMGM CGKSCVSPVK A

In some embodiments of the serpin-SLPI fusion protein of the invention, the SLPI sequence or a SLPI-derived sequence of the fusion protein includes a human SLPI polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 10.

In some embodiments of the serpin-SLPI fusion proteins of the invention, the SLPI polypeptide sequence or the amino acid sequence derived from an SLPI polypeptide is or is derived from, one or more of the human SLPI polypeptide sequences shown in GenBank Accession Nos. CAA28187.1, NP_003055.1, EAW75869.1, P03973.2, AAH20708.1, CAB64235.1, CAA28188.1, AAD19661.1, and/or BAG35125.1.

In some embodiments of the serpin-SLPI fusion proteins of the invention, the SLPI polypeptide sequence or a SLPI-derived sequence of the fusion protein includes a human SLPI polypeptide sequence that is modified at a Methoine (Met) residue. In these Met mutations, the Met residue can be substituted with any amino acid. For example, the Met residue can be substituted with an amino acid with a hydrophobic side chain, such as, for example, leucine (Leu, L) or valine (Val, V). Without wishing to be bound by theory, the Met mutation(s) prevent oxidation and subsequent inactivation of the inhibitory activity of the fusion proteins of the invention. In some embodiments, the Met mutation is at position 98 of an SLPI polypeptide. For example, the modified SLPI polypeptide sequence of the serpin-SLPI includes mutations M98L or M98V in SEQ ID NO: 8.

In other embodiments, the WAP domain-containing polypeptide sequence of the fusion protein includes an elafin polypeptide sequence or an amino acid sequence that is derived from elafin. These embodiments are referred to herein as "serpin-elafin fusion proteins. In some embodiments, the elafin polypeptide sequence includes a portion of the elafin protein, such as for example, the WAP domain or a sub-portion thereof. In a preferred embodiment, the elafin polypeptide sequence or an amino acid sequence that is derived from elafin is or is derived from a human elafin polypeptide sequence.

In some embodiments of the serpin-elafin fusion proteins, the fusion protein includes a full-length human elafin polypeptide sequence having the following amino acid sequence:

(SEQ ID NO: 11)
1 MRASSFLIVV VFLIAGTLVL EAAVTGVPVK GQDTVKGRVP FNGQDPVKGQ VSVKGQDKVK
61 AQEPVKGPVS TKPGSCPIIL IRCAMLNPPN RCLKDTDCPG IKKCCEGSCG MACFVPQ

In some embodiments of the serpin-elafin fusion proteins, the fusion protein includes a human elafin polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 11.

In some embodiments of the serpin-elafin fusion proteins, the fusion protein includes a portion of the full-length human elafin polypeptide sequence, where the portion has the following amino acid sequence:

```
                                                            (SEQ ID NO: 12)
  1 AVTGVPVKGQ DTVKGRVPFN GQDPVKGQVS VKGQDKVKAQ EPVKGPVSTK PGSCPIILIR

61 CAMLNPPNRC LKDTDCPGIK KCCEGSCGMA CFVPQ
```

In some embodiments of the serpin-elafin fusion proteins, the fusion protein includes a human elafin polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 12.

In some embodiments of the serpin-elafin fusion proteins, the fusion protein includes the WAP domain of the full-length human elafin polypeptide sequence, where the WAP domain has the following amino acid sequence:

```
                                                            (SEQ ID NO: 13)
  1 VSTKPGSCPI ILIRCAMLNP PNRCLKDTDC PGIKKCCEGS CGMACFVPQ
```

In some embodiments of the serpin-elafin fusion proteins, the fusion protein includes a human elafin polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 13.

In some embodiments of the serpin-elafin fusion proteins, the elafin polypeptide sequence or the amino acid sequence derived from an elafin polypeptide is derived from one or more of the human elafin polypeptide sequences shown in GenBank Accession Nos. P19957.3, NP_002629.1, BAA02441.1, EAW75814.1, EAW75813.1, Q8IUB2.1, and/or NP_542181.1.

In other embodiments, the WAP domain-containing polypeptide sequence of the fusion protein includes an Eppin polypeptide sequence or an amino acid sequence that is derived from Eppin. These embodiments are referred to herein as "serpin$_{(a)}$-Eppin fusion proteins. In some embodiments, the Eppin polypeptide sequence of the serpin-Eppin fusion protein includes a portion of the Eppin protein, such as for example, the WAP domain or a sub-portion thereof. In a preferred embodiment, the Eppin polypeptide sequence or an amino acid sequence that is derived from Eppin is or is derived from a human Eppin polypeptide sequence.

In some embodiments of the serpin-Eppin fusion proteins, the Eppin polypeptide sequence or amino acid sequence derived from an Eppin polypeptide is or is derived from one or more of the human Eppin polypeptide sequences shown in GenBank Accession Nos. O95925.1, NP_065131.1, AAH44829.2, AAH53369.1, AAG00548.1, AAG00547.1, and/or AAG00546.1.

In some embodiments, the serpin polypeptide of the serpin-WAP domain fusion protein includes at least the amino acid sequence of the reactive site loop portion of the AAT protein. In some embodiments, the reactive site loop portion of the AAT protein includes at least the amino acid sequence of SEQ ID NO:1. In some embodiments, the serpin polypeptide of the serpin-WAP fusion protein includes at least the amino acid sequence of a variant of the reactive site loop portion of the AAT protein. In some embodiments, the variant of the reactive site loop portion of the AAT protein includes at least the amino acid sequence of SEQ ID NO:32 or SEQ ID NO:33. In some embodiments, the serpin polypeptide of the serpin-WAP domain fusion protein includes at least the full-length human AAT polypeptide sequence having amino acid sequence of SEQ ID NO: 2. In some embodiments the serpin polypeptide of the serpin-WAP domain fusion protein includes human AAT polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 2 or 32 or 33.

In some embodiments, the serpin polypeptide of the serpin-WAP domain fusion protein includes the AAT polypeptide sequence is, or the amino acid sequence derived from an AAT polypeptide is derived from, one or more of the human AAT polypeptide sequences shown in GenBank Accession Nos. AAB59495.1, CAJ15161.1, P01009.3, AAB59375.1, AAA51546.1, CAA25838.1, NP_001002235.1, CAA34982.1, NP_001002236.1, NP_000286.3, NP_001121179.1, NP_001121178.1, NP_001121177.1, NP_001121176.16, NP_001121175.1, NP_001121174.1, NP_001121172.1, and/or AAA51547.1.

In some embodiments, the serpin-WAP domain fusion protein can also include an Fc polypeptide or an amino acid sequence that is derived from an Fc polypeptide. These embodiments are referred to collectively herein as "serpin-Fc-WAP domain fusion proteins." In these embodiments, no particular order is to be construed by this terminology. For example, the order of the fusion protein can be serpin-Fc-WAP domain, serpin-WAP domain-Fc, or any variation combination thereof. The serpin-Fc-WAP domain fusion proteins described herein include at least a serpin polypeptide or an amino acid sequence that is derived from a serpin, WAP domain-containing polypeptide or an amino acid sequence that is derived from a WAP domain-containing polypeptide, and an Fc polypeptide or an amino acid sequence that is derived from an Fc polypeptide.

In some embodiments, where the serpin-WAP domain fusion protein includes an Fc polypeptide sequence, the Fc polypeptide sequence can have the amino acid sequence of SEQ ID NO: 3-7. In other embodiments, where the serpin-WAP domain fusion protein includes an Fc polypeptide sequence, the Fc polypeptide sequence can have at least 50%, 60%, 65%, 70%, 75%, 80%, 85%, 90%, 91%, 92%, 93%, 94%, 95%, 96%, 97%, 98% or 99% identical to the amino acid sequence of SEQ ID NOs. 3-7. In some embodiments, the serpin-WAP domain fusion protein can also include an albumin polypeptide, or an amino acid sequence that is derived from an albumin polypeptide. These embodiments are referred to collectively herein as "serpin-albumin-WAP domain fusion proteins." In these embodiments, no particular order is to be construed by this terminology. For example, the order of the fusion protein can be serpin-albumin-WAP domain, serpin-WAP domain-albumin, or any variation combination thereof. The serpin-albumin-WAP domain fusion proteins described herein include at least a serpin polypeptide or an amino acid sequence that is derived from a serpin, WAP domain-containing polypeptide, or an amino acid sequence that is derived from a WAP domain-containing polypeptide, and an albumin polypeptide, or an amino acid sequence that is derived from an albumin polypeptide.

In some embodiments where the serpin-WAP domain fusion protein includes an albumin polypeptide sequence, the albumin polypeptide sequence includes the amino acid sequence of SEQ ID NO: 14-15, described herein. In other embodiments, where the serpin-WAP domain fusion protein includes an albumin polypeptide sequence, the albumin polypeptide sequence has at least 50%, 60%, 65%, 70%, 75%, 80%, 85%, 90%, 91%, 92%, 93%, 94%, 95%, 96%, 97%, 98% or 99% identity to the any one of the amino acid sequences having SEQ ID NO: 14 or 15.

In some embodiments, the second polypeptide (Polypeptide 2) of the serpin fusion protein is an albumin polypeptide or is derived from an albumin polypeptide. These embodiments are referred to collectively herein as "serpin$_{(a')}$-albumin fusion proteins." The serpin-albumin fusion proteins described herein include at least a serpin polypeptide or an amino acid sequence that is derived from a serpin and an albumin polypeptide or an amino acid sequence that is derived from an albumin polypeptide. In addition this invention relates to serpin albumin binding polypeptide fusion proteins, wherein the albumin is operably linked to the serpin via an intermediate binding molecule. Herein, the serpin is non-covalently or covalently bound to human serum albumin.

In embodiments where the fusion protein of the invention includes an albumin polypeptide sequence, the albumin polypeptide sequence of the fusion protein is a human serum albumin (HSA) polypeptide or an amino acid sequence derived from HSA. In some embodiments, the fusion protein includes a HSA polypeptide sequence having the following amino acid sequence:

(SEQ ID NO: 14)
DAHKSEVAHRFKDLGEENFKALVLIAFAQYLQQCPFEDHVKLVNEVT

EFAKTCVADESAENCDKSLHTLFGDKLCTVATLRETYGEMADCCAKQ

EPERNECFLQHKDDNPNLPRLVRPEVDVMCTAFHDNEETFLKKYLYE

IARRHPYFYAPELLFFAKRYKAAFTECCQAADKAACLLPKLDELRDE

GKASSAKQRLKCASLQKFGERAFKAWAVARLSQRFPKAEFAEVSKLV

TDLTKVHTECCHGDLLECADDRADLAKYICENQDSISSKLKECCEKP

LLEKSHCIAEVENDEMPADLPSLAADFVESKDVCKNYAEAKDVFLGM

FLYEYARRHPDYSVVLLLRLAKTYETTLEKCCAAADPHECYAKVFDE

FKPLVEEPQNLIKQNCELFEQLGEYKFQNALLVRYTKKVPQVSTPTL

VEVSRNLGKVGSKCCKHPEAKRMPCAEDYLSVVLNQLCVLHEKTPVS

DRVTKCCTESLVNRRPCFSALEVDETYVPKEFNAETFTFHADICTLS

EKERQIKKQTALVELVKHKPKATKEQLKAVMDDFAAFVEKCCKADDK

ETCFAEEGKKLVAASQAALGL

In embodiments where the fusion protein of the invention includes an albumin polypeptide sequence, the albumin polypeptide sequence of the fusion protein includes a human serum albumin polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 14.

In embodiments where the fusion protein of the invention includes an albumin polypeptide sequence, the albumin polypeptide sequence of the fusion protein fusion protein includes a domain 3 of human serum albumin polypeptide sequence having the following amino acid sequence:

(SEQ ID NO: 15)
EEPQNLIKQNCELFEQLGEYKFQNALLVRYTKKVPQVSTPTLVEVSR

NLGKVGSKCCKHPEAKRMPCAEDYLSVVLNQLCVLHEKTPVSDRVTK

CCTESLVNRRPCFSALEVDETYVPKEFNAETFTFHADICTLSEKERQ

IKKQTALVELVKHKPKATKEQLKAVMDDFAAFVEKCCKADDKETCFA

EEGKKLVA

In embodiments where the fusion protein of the invention includes an albumin polypeptide sequence, the albumin polypeptide sequence of the fusion protein includes a human serum albumin polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 15.

In some embodiments where the fusion protein of the invention includes an albumin polypeptide sequence, the fusion protein is linked to the human serum albumin via an intermediate albumin binding polypeptide. The albumin binding polypeptide can be an antibody or an antibody fragment or derived from an antibody or antibody fragment. In a preferred embodiment, the albumin binding polypeptide or an amino acid sequence that is derived from the antibody or antibody fragment is derived from a chimeric, humanized, or fully human antibody sequence. The term antibody fragment includes single chain, Fab fragment, a F(ab')$_2$ fragment, a scFv, a scAb, a dAb, a single domain heavy chain antibody, and a single domain light chain antibody. In addition, the albumin binding polypeptide can be an albumin binding peptide. Another embodiment of the invention is a serpin albumin binding polypeptide fusion, wherein the albumin binding polypeptide is domain 3 of *Streptococcal* protein G or a sequence derived from domain 3 of *Streptococcal* protein G.

In some embodiments, the serpin polypeptide of the serpin$_{(a')}$-albumin fusion proteins includes at least the amino acid sequence of the reactive site loop portion of the AAT protein. In some embodiments, the reactive site loop portion of the AAT protein includes at least the amino acid sequence of SEQ ID NO:1. In some embodiments, the serpin polypeptide of the serpin-albumin fusion protein includes at least the amino acid sequence of a variant of the reactive site loop portion of the AAT protein. In some embodiments, the variant of the reactive site loop portion of the AAT protein includes at least the amino acid sequence of SEQ ID NO:32 or SEQ ID NO:33. In some embodiments, the serpin polypeptide of the serpin-albumin fusion proteins includes at least the full-length human AAT polypeptide sequence having amino acid sequence of SEQ ID NO: 2. In some embodiments the serpin polypeptide of the serpin-albumin fusion proteins includes human AAT polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 2 or 32 or 33.

In some embodiments, the serpin polypeptide of the serpin-albumin fusion proteins includes the AAT polypeptide sequence or the amino acid sequence derived from an AAT polypeptide is or is derived from one or more of the human AAT polypeptide sequences shown in GenBank Accession Nos. AAB59495.1, CAJ15161.1, P01009.3, AAB59375.1, AAA51546.1, CAA25838.1, NP_001002235.1, CAA34982.1, NP_001002236.1, NP_000286.3, NP_001121179.1, NP_001121178.1, NP_001121177.1, NP_001121176.16, NP_001121175.1, NP_001121174.1, NP_001121172.1, and/or AAA51547.1.

In some embodiments, the fusion proteins are modified to increase or otherwise inhibit proteolytic cleavage, for example, by mutating one or more proteolytic cleavage sites. In some embodiments, the fusion proteins are modified to alter or otherwise modulate an Fc effector function of the fusion protein, while simultaneously retaining binding and inhibitory function as compared to an unaltered fusion protein. Fc effector functions include, by way of non-limiting examples, Fc receptor binding, prevention of proinflammatory mediator release upon binding to the Fc receptor, phagocytosis, modified antibody-dependent cell-mediated cytotoxicity (ADCC), modified complement-dependent cytotoxicity (CDC), modified glycosylation at Asn297 residue (EU index of Kabat numbering, Kabat et al 1991 *Sequences of Proteins of Immunological Interest*) of the Fc polypeptide. In some embodiments, the fusion proteins are mutated or otherwise modified to influence Fc receptor binding. In some embodiments, the Fc polypeptide is modified to enhance FcRn binding. Examples of Fc polypeptide mutations that enhance binding to FcRn are Met252Tyr, Ser254Thr, Thr256Glu (M252Y, S256T, T256E) (Kabat numbering, Dall'Acqua et al 2006, *J. Biol Chem* Vol 281(33) 23514-23524), or Met428Leu and Asn434Ser (M428L, N434S) (Zalevsky et al 2010 *Nature Biotech*, Vol. 28(2) 157-159). (EU index of Kabat et al 1991 *Sequences of Proteins of Immunological Interest*). In some embodiments the Fc polypeptide portion is mutated or otherwise modified so as to disrupt Fc-mediated dimerization (Ying et al 2012 *J. Biol Chem* 287(23): 19399-19408). In these embodiments, the fusion protein is monomeric in nature.

The fusion proteins and variants thereof provided herein exhibit inhibitory activity, for example by inhibiting a serine protease such as human neutrophil elastase (NE), a chemotrypsin-fold serine protease that is secreted by neutrophils during an inflammatory response. The fusion proteins provided herein completely or partially reduce or otherwise modulate serine protease expression or activity upon binding to, or otherwise interacting with, a serine protease, e.g., a human serine protease. The reduction or modulation of a biological function of a serine protease is complete or partial upon interaction between the fusion proteins and the human serine protease protein, polypeptide and/or peptide. The fusion proteins are considered to completely inhibit serine protease expression or activity when the level of serine protease expression or activity in the presence of the fusion protein is decreased by at least 95%, e.g., by 96%, 97%, 98%, 99% or 100% as compared to the level of serine protease expression or activity in the absence of interaction, e.g., binding, with a fusion protein described herein. The fusion proteins are considered to partially inhibit serine protease expression or activity when the level of serine protease expression or activity in the presence of the fusion protein is decreased by less than 95%, e.g., 10%, 20%, 25%, 30%, 40%, 50%, 60%, 75%, 80%, 85% or 90% as compared to the level of serine protease expression or activity in the absence of interaction, e.g., binding, with a fusion protein described herein.

The fusion proteins described herein are useful in a variety of therapeutic, diagnostic and prophylactic indications. For example, the fusion proteins are useful in treating a variety of diseases and disorders in a subject. In some embodiments, the serpin fusion proteins, including, fusion proteins described herein, are useful in treating, alleviating a symptom of, ameliorating and/or delaying the progression of a disease or disorder in a subject suffering from or identified as being at risk for a disease or disorder selected from alpha-1-antitrypsin (AAT) deficiency, emphysema, chronic obstructive pulmonary disease (COPD), acute respiratory distress sydrome (ARDS), allergic asthma, cystic fibrosis, cancers of the lung, ischemia-reperfusion injury, including, e.g., ischemia/reperfusion injury following cardiac transplantation, myocardial infarction, rheumatoid arthritis, septic arthritis, psoriatic arthritis, ankylosing spondylitis, Crohn's disease, psoriasis, type I and/or type II diabetes, bacterial infections, fungal infections, viral infections, pneumonia, sepsis, graft versus host disease (GVHD), wound healing, Systemic lupus erythematosis, and Multiple sclerosis.

Pharmaceutical compositions according to the invention include a fusion protein of the invention, including modified fusion proteins and other variants, along with a suitable carrier. These pharmaceutical compositions can be included in kits, such as, for example, diagnostic kits.

DETAILED DESCRIPTION OF THE INVENTION

Figure 1A:
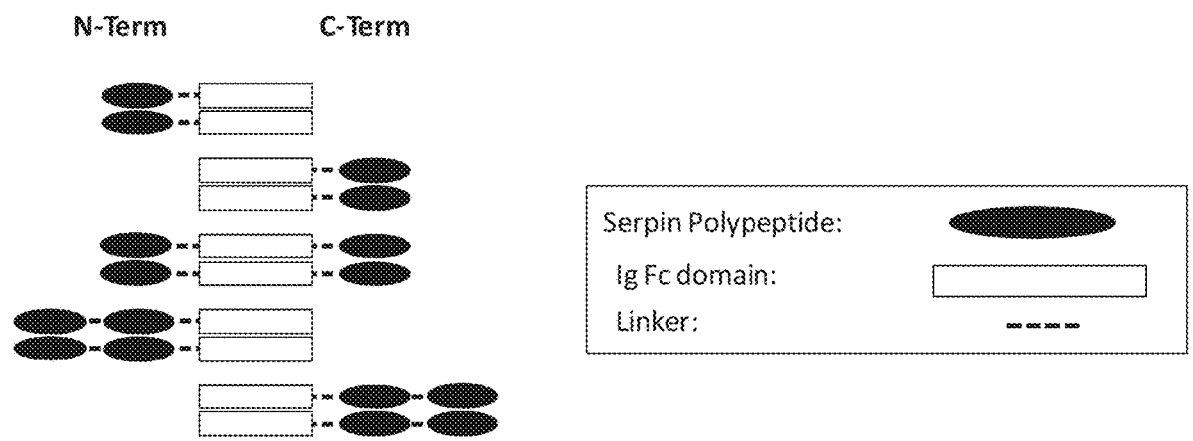
FIG. 1A is a schematic representation of some embodiments of serpin-Fc fusion proteins according to the invention. The serpin can be located at any position within the fusion protein. Serpin-Fc fusion protein incorporating more than one serpin polypeptide are also represented.

Human neutrophil elastase (NE) is a chymotrypsin-fold serine protease, secreted by neutrophils during inflammation. Aberrant activity of NE results in a progressive degradation of elastin tissues and the slow destruction of the alveolar structures of the lungs leading to emphysema and lung fibrosis (Lungarella et al 2008 *Int. J. Biochem Cell Biol* 40:1287). Often, misguided NE activity is due to an imbalance of the protease with its natural inhibitor, alpha1-antitrypsin (AAT). This imbalance can result from enhanced neutrophil infiltration into the lungs, as observed in the lungs of smokers and patients with Cystic Fibrosis (CF), or Acute Respiratory Distress Syndrome (ARDS). Conversely, a deficiency of AAT, usually as a result of a point mutation that causes ATT to aggregate and accumulate in the liver, leaves the lungs exposed to unchecked NE activity. Individuals with AAT deficiencies are at increased the risk of emphysema, COPD, liver disease, and numerous other conditions.

AAT deficiency affects approximately 100,000 Americans (according to estimates from the Alpha-1 Foundation), and many of the afflicted people die in their 30's and 40's. There are currently only a few FDA-approved drugs for treatment of ATT deficiency (Prolastin®, Aralast™, Zemaira®, Glassia™). Each drug is the natural AAT derived from pooled human plasma, which appears to be insufficient to meet the anticipated clinical demand. Furthermore, these products have short serum half-lives ($T_{1/2}$ of approximately 5 days) and require high dose (60 mg/kg body weight) weekly infusions. The current market for these drugs is estimated at approximately $400 million. The market for AAT-like drugs is likely substantially larger, based on the estimation that as many as 95% of individuals with AAT-deficiencies go undiagnosed, and the fact that these drugs have the potential to be effective therapies for pathologies characterized by enhanced NE activity in individuals that are not AAT-deficient (e.g., cystic fibrosis (CF), acute respiratory distress syndrome (ARDS), smoking-induced emphysema and/or COPD).

AAT has been suggested to have broad spectrum anti-inflammatory activity (Tilg et al 1993 *J Exp Med* 178:1629-1636, Libert et al 1996 *Immunol* 157:5126-5129, Pott et al, Journal of Leukocyte Biology 85 2009, Janciauskiene et al 2007 *J. Biol Chem* 282(12): 8573-8582, Nita et al 2007 *Int J Biochem* Cell Biol 39:1165-1176). Recently, evidence has mounted that AAT may be useful in treating numerous human pathologies, outside of the commonly suggested inflammatory pulmonary conditions. Human AAT has shown to protect mice from clinical and histopathological signs of experimental autoimmune encephalomyelitis (EAE), suggesting it could be a potential treatment of autoimmune diseases, such as multiple sclerosis or systemic lupus erythematosus (SLE) (Subramanian et al 2011 Metab Brain Dis 26:107-113): Serum AAT has shown activity in rodent models of Graft Versus Host Disease (GVHD) (Tawara et al 2011 *Proc. Natl. Acad. Sci.* USA 109: 564-569, Marcondes et al 2011 *Blood* November 3; 118(18):5031-9), which has led to a human clinical trial using AAT to treat individuals with Steroid Non-responsive Acute GVHD (NCT01523821). Additionally, AAT has been effective in animal models of type I and type II diabetes, dampening inflammation, protecting islet cells from apoptosis and enabling durable islet cell allograft (Zhang et al 2007 *Diabetes* 56:1316-1323, Lewis et al 2005 *Proc Natl Acad Sci* USA 102:12153-12158, Lewis et al 2008 *Proc Natl Acad Sci* USA 105:16236-16241, Kalis et al 2010 *Islets* 2:185-189). Currently, there are numerous early human clinical trials of type I diabetes using serum derived AAT products (NCT01183468, NCT01319331, NCT01304537).

The current serum-derived AAT products undergo extensive purification and testing to ensure the removal of pathogenic viruses, however, the risk of transmission of infectious agents cannot be completely eliminated. Moreover, serum is limited, which limits the production capacity of serum derived AAT. Attempts to address the concerns of serum derived products and production issues have been aimed at the expression of recombinant AAT. However, after 20 years of work, the generation of a therapeutically viable recombinant AAT has yet to reach the market (Karnaukhova et al 2006 Amino Acids 30: 317). Like the plasma-derived products, recombinant versions of AAT suffer from short serum half-lives, low production yields, and poor lung distribution.

Figure 1B:
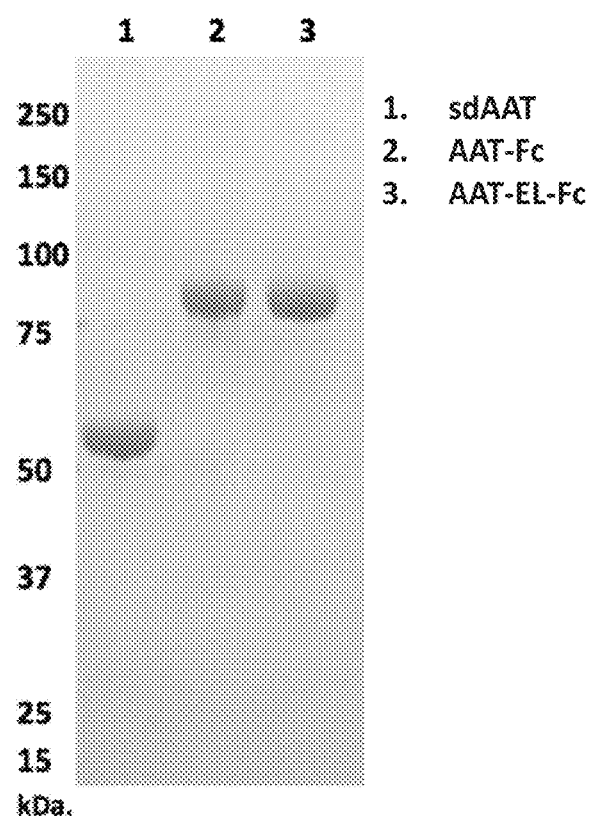
FIG. 1B is a photograph of a SDS-PAGE gel showing serum derived AAT (lane 1), AAT-Fc1 (lane 2, human IgG1 Fc), and AAT-EL-Fc1 (lane 3, Met351Glu, Met358Leu mutations within AAT, human IgG1 Fc).
Figure 1C:
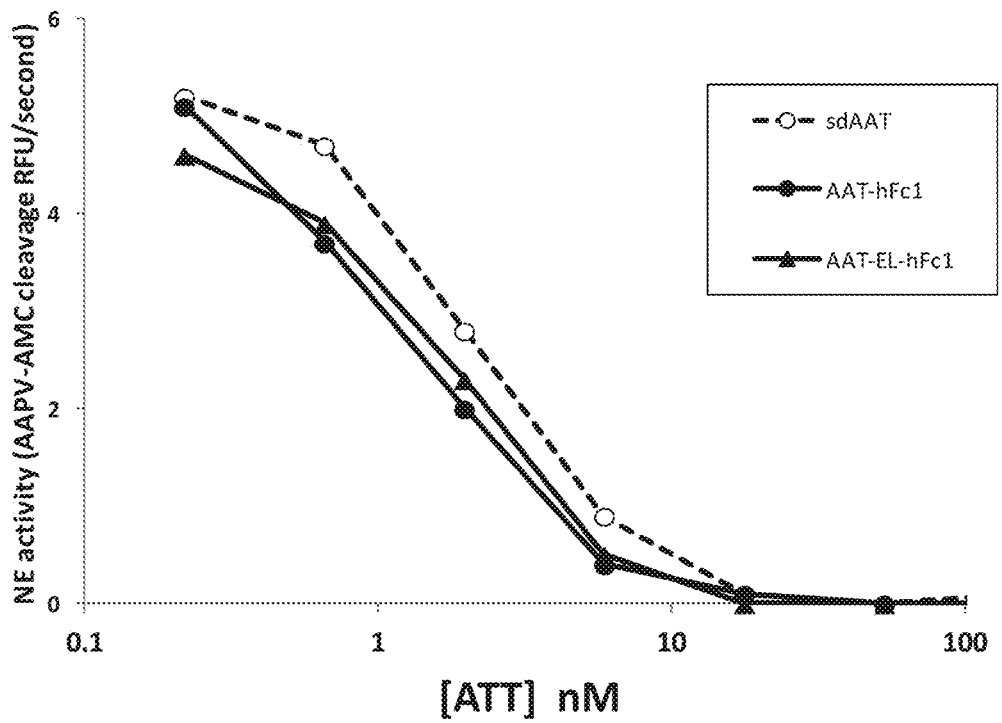
FIG. 1C is a graph showing the inhibition of neutrophil elastase activity by AAT-Fc fusion proteins.
Figure 1D:
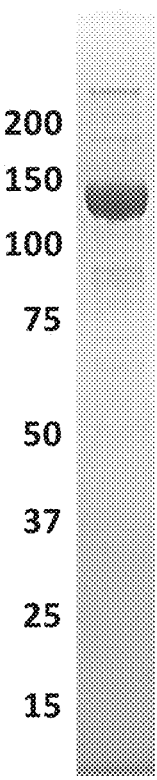
FIG. 1D is a photograph of a SDS-PAGE gel showing tetravalent AAT-Fc-AAT, having two AAT polypeptides per Fc polypeptide.
Figure 1E:
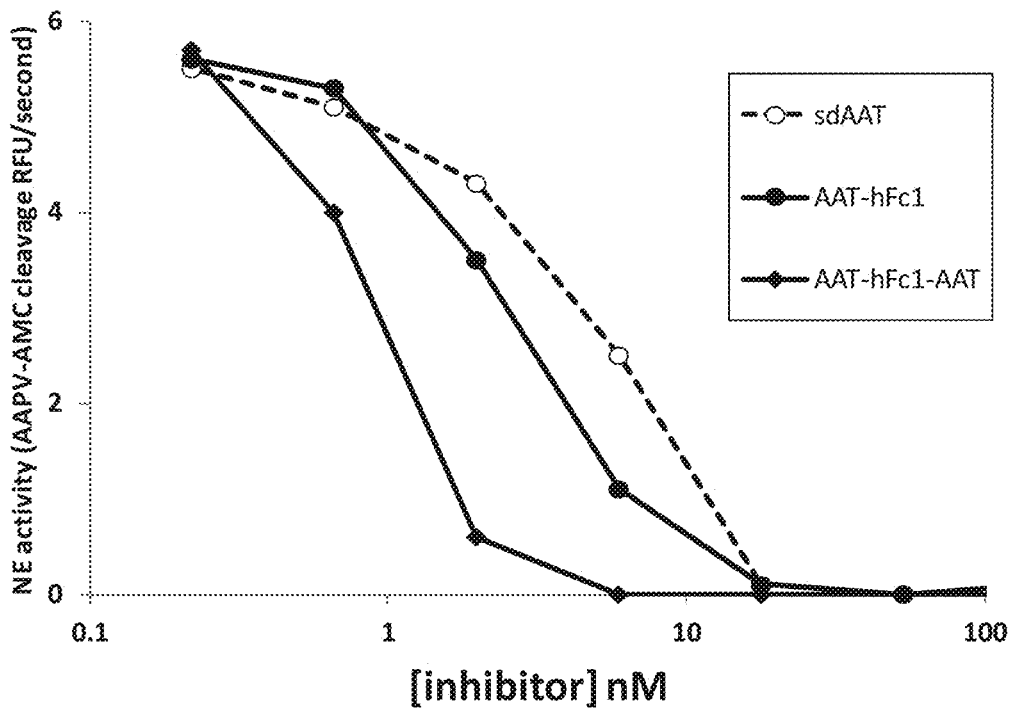
FIG. 1E is a graph showing the inhibition of neutrophil elastase activity by a tetravalent AAT-Fc-AAT fusion protein.
Figure 1F:
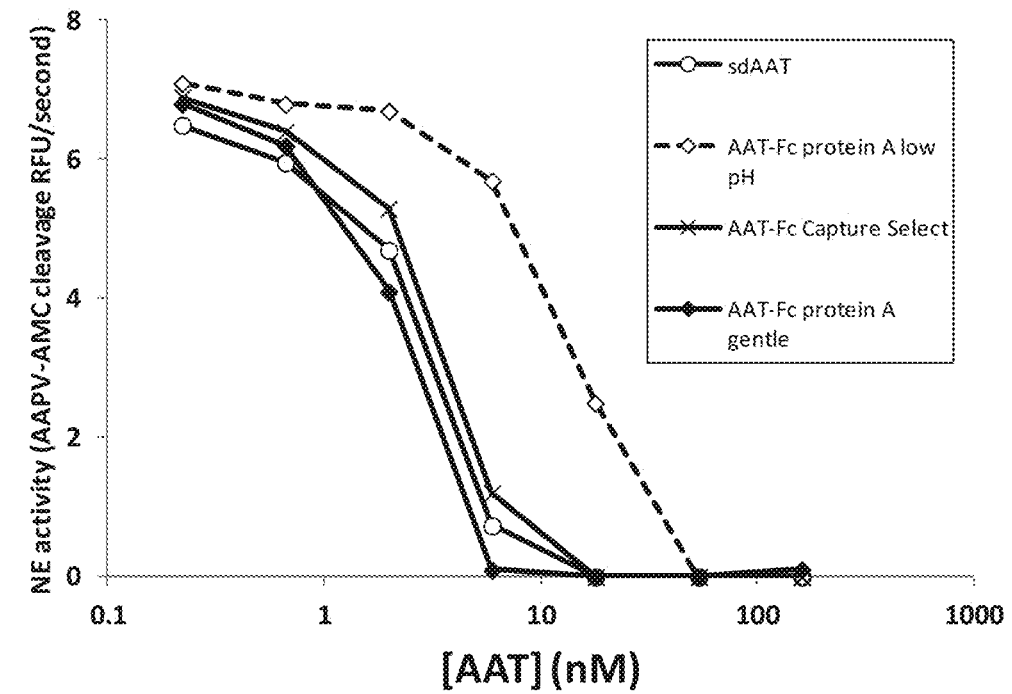
FIG. 1F is a graphing demonstrating the effect of low pH elution from protein A resin, wherein the NE inhibiting capacity of the AAT-Fc fusion protein eluted at low pH is drastically reduced.
Figure 1G:
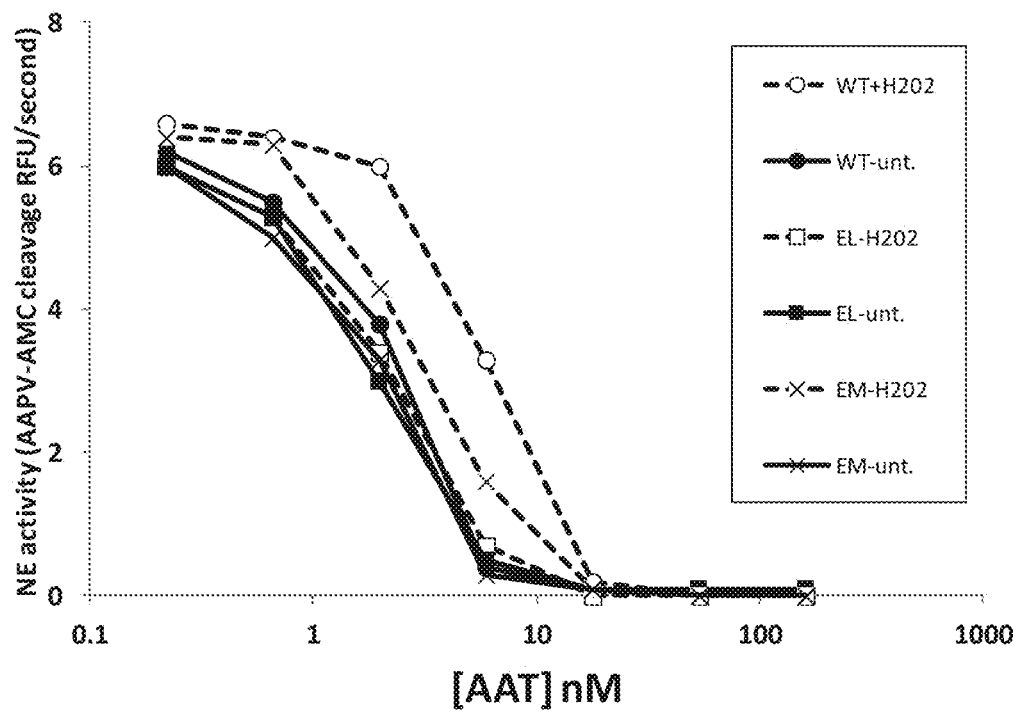
FIG. 1G is a graph showing that the double mutant, AAT-EL-Fc (Met351Glu, Met358Leu mutations) is resistant to $H_2O_2$ inactivation (conc.), compared to wild type AAT and the single mutant AAT-EM-Fc (Met351Glu).

The fusion proteins of the present invention have enhanced functionalities compared to the unmodified AAT molecule. The fusion of an AAT polypeptide with a second polypeptide that interacts with the neonatal Fc receptor (FcRn), serves to increase the serum half-life, providing a much needed dosing benefit for patients. These FcRn interacting polypeptides of the fusion protein include immunoglobulin (Ig) Fc polypeptides derived from human IgG1, IgG2, IgG3, IgG4, or IgM, and derivatives of human albumin. In some embodiments, the fusion protein incorporates mutations with the AAT portion that render the molecule more resistant to inactivation by oxidation. For example Met351Glu, Met358Leu (AAT-EL-Fc), demonstrates resistance inactivation by $H_2O_2$ oxidation (FIG. 1G). While AAT is a natural anti-inflammatory protein, some embodiments of the invention provide enhanced inflammation dampening capacity through the fusion of an AAT polypeptide and a cytokine targeting polypeptide. The coupling of dual anti-inflammatory functionalities from AAT and a second polypeptide, will provide more a potent therapeutic protein than either polypeptide on their own. Additionally, the coupling the anti-infective activity of AAT will mitigate the infection risk of most cytokine targeting biologics. Some embodiments provide for more potent anti-inflammatory and anti-infective proteins through the fusion an AAT-polypeptide and WAP domain contain polypeptide. The fusion proteins of the present invention are expected to be a great therapeutic utility and be superior to the current serum derived AAT products.

To extend the half-life of recombinant AAT, recombinant DNA technology was used to create a AAT gene fusion with the Fc domain of human IgG1, IgG2, IgG3, IgG4, IgM, or HSA, such that the expected protein product would be AAT followed by an Fc domain ((AAT-Fc (IgG1), AAT-Fc (IgG2), AAT-Fc (IgG3), AAT-Fc (IgG4), AAT-Fc (IgM)) or AAT followed by HSA. While it was known that fusion of Fc domains of HSA to some proteins, protein domains or peptides could extend their half-lives (see e.g., Jazayeri et al. BioDrugs 22, 11-26, Huang et al. (2009) Curr Opin Biotechnol 20, 692-699, Kontermann et al. (2009) BioDrugs 23, 93-109, Schmidt et al. (2009) Curr Opin Drug Discov Devel 12, 284-295), it was unknown if an Fc domain or HSA fused to AAT would allow for proper folding and maintenance of NE inhibitory activity, or could extend the half-life of recombinant AAT. The fusion proteins of the present invention are shown to be potent inhibitors of NE, have extended serum half lives, and in some embodiments resistant to oxidation. In other embodiments, the fusion proteins described herein have distinct properties by the incorporation of other functional polypeptides, including cytokine targeting polypeptides, and WAP domain containing polypeptides.

The fusion proteins described herein include at least a serpin polypeptide or an amino acid sequence that is derived from a serpin and a second polypeptide. In some embodiments, for example, the invention provides a serpin polypeptide fused to human IgG1-Fc, IgG2-Fc, IgG3-Fc, IgG4-Fc, IgM-Fc, or HSA derivatives. The serpin-fusion described herein are expected to be useful in treating a variety of indications, including, by way of non-limiting example, alpha-1-antitrypsin (AAT) deficiency, emphysema, chronic obstructive pulmonary disease (COPD), acute respiratory distress syndrome (ARDS), allergic asthma, cystic fibrosis, cancers of the lung, ischemia-reperfusion injury, including, e.g., ischemia/reperfusion injury following cardiac transplantation, myocardial infarction, rheumatoid arthritis, septic arthritis, psoriatic arthritis, ankylosing spondylitis, Crohn's disease, psoriasis, type I and/or type II diabetes, bacterial infections, fungal infections, viral infections, pneumonia, sepsis, graft versus host disease (GVHD), wound healing, Systemic lupus erythematosis, and Multiple sclerosis.

In some embodiments, the fusion proteins described herein include at least an alpha-1-antitrypsin (AAT) polypeptide or an amino acid sequence that is derived from AAT and second polypeptide. For example, the invention provides alpha-1-antitrypsin (AAT) fused to human IgG1-Fc, IgG2-Fc, IgG3-Fc, IgG4-Fc, IgM-Fc, or HSA derivatives.

In some embodiments, the fusion proteins described herein include at least a serpin polypeptide or an amino acid sequence that is derived from a serpin polypeptide and a cytokine targeting polypeptide or an amino acid sequence that is derived from a cytokine targeting polypeptide. For example, the invention provides serpin polypeptide or a sequence derived from a serpin polypeptide fused to a human cytokine receptor or derivative thereof. Another embodiment of the invention provides serpin polypeptide or a sequence derived from a serpin polypeptide fused to a cytokine targeting antibody, e.g., an anti-cytokine antibody, or a sequence derived from of a cytokine targeting antibody, e.g., an anti-cytokine antibody, or sequence derived from a fragment of cytokine targeting antibody, e.g., a fragment of an anti-cytokine antibody. For example, the invention provides a serpin polypeptide or a sequence derived from a serpin polypeptide fused to a cytokine targeting polypeptide in which the cytokine targeting polypeptide binds any of the following human cytokines: TNFα, IgE, IL-12, IL-23, IL-6, IL-1α, IL-1β, IL-17, IL-13, IL-4, IL-10, IL-2, IL-18, IL-27, or IL-32.

For example, in some embodiments, the cytokine targeting polypeptide targets TNFα and includes any of the following TNFα-targeting polypeptide or sequences derived from the following TNFα-targeting polypeptides: Remicade®, Humira®, Simponi®, Cimiza®, Enbrel® or ATN-103 and ATN-192.

For example, in some embodiments, the cytokine targeting polypeptide targets IgE and includes any of the following IgE-targeting polypeptide or sequences derived from the following IgE-targeting polypeptides: Xolair or FcεRI.

For example, in some embodiments, the cytokine targeting polypeptide targets the shared p40 subunit of IL-12 and IL-23 and includes the Stelara® polypeptide or sequences derived from the Stelara® polypeptide.

For example Stelara® the cytokine targeting polypeptide targets IL-13 and includes the CDP7766 polypeptide or sequences derived from the CDP7766 polypeptide.

In some embodiments, the fusion proteins described herein include at least a alpha-1-antitrypsin (AAT) polypeptide or an amino acid sequence that is derived from AAT and a cytokine targeting polypeptide or an amino acid sequence that is derived from a cytokine targeting polypeptide. For example, the invention provides alpha-1-antitrypsin inhibitor (AAT) fused a cytokine targeting polypeptide in which the cytokine targeting polypeptide binds any of the following human cytokines: TNFα, IgE, IL-6, IL-1α, IL-1β, IL-12, IL-17, IL-13, IL-23, IL-4, IL-10, IL-2, IL-18, IL-27, or IL-32.

In some embodiments the cytokine targeting polypeptide binds a cytokine receptor and prevents binding of the cytokine. For example, the present invention includes a serpin fused to a cytokine receptor targeting antibody. For example, the invention provides alpha-1-antitrypsin inhibitor (AAT) fused a cytokine targeting polypeptide in which the cytokine targeting polypeptide binds the receptor of any of the following human cytokines: TNFα, IgE, IL-6, IL-1α, IL-1β, IL-12, IL-17, IL-13, IL-23, the p40 subunit of IL-12 and IL-23, IL-4, IL-10, IL-2, IL-18, IL-27, or IL-32.

For example, in some embodiments, the cytokine targeting polypeptide targets the IL-6 receptor and includes the Actemra® polypeptide (as described in patent publication EP0628639), or the ALX-0061 polypeptide (as described in WO2010/115998), or sequences derived from the Actemra® polypeptide, or ALX-0061 polypeptide.

For example, Actemra® the cytokine targeting polypeptide targets the IL-6 receptor and includes the tocilizumab polypeptide or sequences derived from the tocilizumab polypeptide.

The targeting of inflammatory cytokines and immune-stimulating agents by protein therapeutics has demonstrated clinical success in numerous inflammatory conditions. The most common proteins used as cytokine targeting agents are the soluble cytokine receptors and monoclonal antibodies and fragments thereof. A significant drawback with targeting cytokines is the increased risk of infection in these patients, as evidenced by the TNFα targeting biologics, Remicade®, Humira®, Simponi®, Cimiza®, and Enbrel®, and the IL-12/23 p40 targeting antibody, Stelara®. This is likely to be a common problem of targeting inflammatory cytokines leading to immune suppression in patients. AAT and other serpin proteins are interesting in that they demonstrate both anti-infective and anti-inflammatory activities. Thus, the serpin-cytokine targeting polypeptide fusion proteins of this invention can dampen aberrant cytokine activities while alleviating the risk of infections.

In some embodiments, the fusion proteins described herein include a serpin polypeptide or an amino acid sequence that is derived from a serpin, a WAP domain-containing polypeptide or an amino acid sequence that is derived from a WAP domain-containing polypeptide, and an Fc polypeptide or an amino acid sequence that is derived from an Fc polypeptide. For example, the invention provides a serpin polypeptide, a WAP domain-containing polypeptide and human IgG1-Fc, IgG2-Fc, IgG3-Fc, IgG4-Fc or IgM-Fc derivatives operably linked together in any functional combination. In some embodiments, the WAP domain containing protein is human SLPI or derived from human SLPI. In other embodiments, the WAP domain containing protein is human ELAFIN or derived from human ELAFIN. In some embodiments, the fusion proteins described herein include at least an alpha-1-antitrypsin (AAT) polypeptide or an amino acid sequence that is derived from AAT and a SLPI polypeptide or an amino acid sequence that is derived from SLPI. In some embodiments, the fusion proteins described herein include at least an AAT polypeptide or an amino acid sequence that is derived from AAT and an ELAFIN polypeptide or an amino acid sequence that is derived from Elafin.

SPLI and Elafin are WAP domain containing proteins that display serine protease inhibitory activity. Both of these proteins are anti-inflammatory in function. In addition these proteins possess broad anti-infective capacities toward numerous strains of bacteria, viruses, and fungi.

In some embodiments, the fusion proteins described herein include at least a serpin polypeptide or an amino acid sequence that is derived from a serpin and a human serum albumin (HSA) polypeptide or an amino acid sequence that is derived from a HSA polypeptide. Further embodiments of invention include serpin-albumin binding polypeptide fusion proteins, wherein the albumin binding polypeptide is responsible for the association of the serpin and HSA. Thereby the invention includes both covalent and non-covalent linkages of the serpin polypeptide and the HSA polypeptide or sequences derived from the serpin polypeptide or a HSA polypeptide. For example, the invention provides a serpin polypeptide fused to human HSA, or HSA derivatives, or HSA binding peptide or polypeptides.

In some embodiments, the fusion proteins described herein include at least an alpha-1-antitrypsin (AAT) polypeptide or an amino acid sequence that is derived from AAT and a HSA polypeptide or an amino acid sequence that is derived from a HSA polypeptide. For example, the invention provides alpha-1-antitrypsin (AAT) fused to HSA or a fragment derived from HSA, or an albumin binding polypeptide.

In some embodiments, the fusion proteins described herein include a serpin polypeptide or an amino acid sequence that is derived from a serpin, a HSA polypeptide or or an amino acid sequence that is derived from a HSA polypeptide, and a WAP domain-containing polypeptide or an amino acid sequence that is derived from a WAP domain-containing polypeptide. In some embodiments, the fusion proteins described herein include at least an alpha-1-antitrypsin (AAT) polypeptide or an amino acid sequence that is derived from AAT and a HSA polypeptide or an amino acid sequence that is derived from a HSA polypeptide, and a SLPI polypeptide or amino acid sequence derived from SLPI. In other embodiments, the fusion proteins described herein include at least an alpha-1-antitrypsin (AAT) polypeptide or an amino acid sequence that is derived from AAT and a HSA polypeptide or an amino acid sequence that is derived from a HSA polypeptide, and an Elafin polypeptide or amino acid sequence derived from Elafin.

The fusion proteins of the present invention can be readily produced in mammalian cell expression systems. For example Chinese Hamster Ovary (CHO) cells, Human Embryonic Kidney (HEK) 293 cells, COS cells, PER.C6®, NS0 cells, SP2/0, YB2/0 can readily be used for the expression of the serpin fusion proteins described herein. Importantly, mammalian cell expression systems produce proteins that are generally more optimal for therapeutic use. In contrast to bacterial, insect, or yeast-based expression systems, mammalian cell expression systems yield proteins with glycosylation patterns that are similar or the same as those found in natural human proteins. Proper gylcosylation of a protein can greatly influence serum stability, pharmacokinetics, biodistribution, protein folding, and functionality. Therefore, the ability to produce therapeutic proteins in mammalian expression systems has distinct advantages over other systems. Furthermore, most of the mammalian cell expression systems (e.g., CHO, NS0, PER.C6® cells) can be readily scaled in commercial manufacturing facilities to produce therapeutic proteins to meet clinical demands. The fusion proteins described herein have enhanced functionalities over the natural form of AAT and can be produced in mammalian expression systems for clinical and commercial supply. Some embodiments of the invention include a purification system that enables the isolation of serpin fusion proteins that retain their ability to inhibit NE. Importantly, the purification process of the present invention can be readily incorporated into today's commercial mammalian cell-based manufacturing processes.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. The term patient includes human and veterinary subjects.

It will be appreciated that administration of therapeutic entities in accordance with the invention will be administered with suitable carriers, buffers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a fusion protein of the invention, are used to treat or alleviate a symptom associated with a disease or disorder associated with aberrant serine protease activity in a subject. The present invention also provides methods of treating or alleviating a symptom associated with a disease or disorder associated with aberrant serine protease activity in a subject. A therapeutic regimen is carried out by identifying a subject, e.g., a human patient suffering from (or at risk of developing) a disease or disorder associated with aberrant serine protease activity, using standard methods, including any of a variety of clinical and/or laboratory procedures. The term patient includes human and veterinary subjects. The term subject includes humans and other mammals.

Efficaciousness of treatment is determined in association with any known method for diagnosing or treating the particular disease or disorder associated with aberrant serine protease activity. Alleviation of one or more symptoms of the disease or disorder associated with aberrant serine protease activity indicates that the fusion protein confers a clinical benefit.

Methods for the screening of fusion proteins that possess the desired specificity include, but are not limited to, enzyme linked immunosorbent assay (ELISA), enzymatic assays, flow cytometry, and other immunologically mediated techniques known within the art.

The fusion proteins described herein may be used in methods known within the art relating to the localization and/or quantitation of a target such as a serine protease, e.g., for use in measuring levels of these targets within appropriate physiological samples, for use in diagnostic methods, for use in imaging the protein, and the like). The terms "physiological sample" and "biological sample," used interchangeably, herein are intended to include tissues, cells and biological fluids isolated from a subject, as well as tissues, cells and fluids present within a subject. Included within the usage of the terms "physiological sample" and "biological sample", therefore, is blood and a fraction or component of blood including blood serum, blood plasma, or lymph.

In a given embodiment, fusion proteins specific for a given target, or derivative, fragment, analog or homolog thereof, that contain the target-binding domain, are utilized as pharmacologically active compounds (referred to hereinafter as "Therapeutics").

A fusion protein of the invention can be used to isolate a particular target using standard techniques, such as immunoaffinity, chromatography or immunoprecipitation. Detection can be facilitated by coupling (i.e., physically linking) the fusion protein to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{25}S$ or $^{3}H$.

A therapeutically effective amount of a fusion protein of the invention relates generally to the amount needed to achieve a therapeutic objective. As noted above, this may be a binding interaction between the fusion protein and its target that, in certain cases, interferes with the functioning of the target. The amount required to be administered will furthermore depend on the binding affinity of the fusion protein for its specific target, and will also depend on the rate at which an administered fusion protein is depleted from the free volume other subject to which it is administered. Common ranges for therapeutically effective dosing of an fusion protein or fragment thereof invention may be, by way of nonlimiting example, from about 0.1 mg/kg body weight to about 250 mg/kg body weight. Common dosing frequencies may range, for example, from twice daily to once a month.

Where fusion protein fragments are used, the smallest inhibitory fragment that specifically binds to the target is preferred. For example, peptide molecules can be designed that retain the ability to bind the target. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, growth-inhibitory agent, an anti-inflammatory agent or anti-infective agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the fusion protein, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, nondegradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

Pharmaceutical Compositions

The fusion proteins of the invention (also referred to herein as "active compounds"), and derivatives, fragments, analogs and homologs thereof, can be incorporated into pharmaceutical compositions suitable for administration. Such compositions typically comprise the fusion rotein and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1: AAT-Fc Fusion Proteins and Variants

Exemplary, but non-limiting examples of AAT-Fc fusion proteins according to the invention include the following sequences. While these examples include a hinge sequence and/or a linker sequence, fusion proteins of the invention can be made using any hinge sequence and/or a linker sequence suitable in length and/or flexibility. Alternatively fusion proteins can be made without using a hinge and/or a linker sequence. For example, the polypeptide components can be directly attached.

An exemplary AAT-Fc fusion protein is the AAT-hFc1 (human IgG1 Fc) described herein. As shown below, AAT polypeptide portion of the fusion protein is underlined (SEQ ID NO: 2), the hinge region is shown in normal text (SEQ ID NO: 43), and the IgG-Fc polypeptide portion of the fusion protein is italicized (SEQ ID NO: 3).

AAT-hFc1 (human IgG1 Fc)
(SEQ ID NO: 16)
EDPQGDAAQKTDTSHHDQDHPTFNKITPNLAEFAFSLYRQLAHQSN

STNIFFSPVSIATAFAMLSLGTKADTHDEILEGLNFNLTEIPEAQI

HEGFQELLRTLNQPDSQLQLTTGNGLFLSEGLKLVDKFLEDVKKLY

HSEAFTVNFGDTEEAKKQINDYVEKGTQGKIVDLVKELDRDTVFAL

VNYIFFKGKWERPFEVKDTEEEDFHVDQVTTVKVPMMKRLGMFNIQ

HCKKLSSWVLLMKYLGNATAIFFLPDEGKLQHLENELTHDIITKFL

ENEDRRSASLHLPKLSITGTYDLKSVLGQLGITKVFSNGADLSGVT

EEAPLKLSKAVHKAVLTIDEKGTEAAGAMFLEAIPMSIPPEVKFNK

PFVFLMIEQNTKSPLFMGKVVNPTQKEPKSCDKTHTCPPCP*APELL*

*GGPSVFLFPPKPKDTLMISRTPEVTCVVVDVSHEDPEVKFNWYVDG*

*VEVHNAKTKPREEQYNSTYRVVSVLTVLHQDWLNGKEYKCKVSNKA*

*LPAPIEKTISKAKGQPREPQVYTLPPSRDELTKNQVSLTCLVKGFY*

*PSDIAVEWESNGQPENNYKTTPPVLDSGSFFLYSKLTVDKSRWQQ*

*GNVFSCSVMHEALHNHYTQKSLSLSPGK*

An exemplary AAT-Fc fusion protein is the AAT-hFc2 (human IgG2 Fc), described herein. As shown below, AAT polypeptide portion of the fusion protein is underlined (SEQ ID NO: 2), the hinge region is shown in normal text (SEQ ID NO: 44), and the IgG-Fc polypeptide portion of the fusion protein is italicized (SEQ ID NO: 4).

AAT-hFc2 (human IgG2 Fc)
(SEQ ID NO: 17)
EDPQGDAAQKTDTSHHDQDHPTFNKITPNLAEFAFSLYRQLAHQS

NSTNIFFSPVSIATAFAMLSLGTKADTHDEILEGLNFNLTEIPEA

QIHEGFQELLRTLNQPDSQLQLTTGNGLFLSEGLKLVDKFLEDVK

KLYHSEAFTVNFGDTEEAKKQINDYVEKGTQGKIVDLVKELDRDT

VFALVNYIFFKGKWERPFEVKDTEEEDFHVDQVTTVKVPMMKRLG

MFNIQHCKKLSSWVLLMKYLGNATAIFFLPDEGKLQHLENELTHD

IITKFLENEDRRSASLHLPKLSITGTYDLKSVLGQLGITKVFSNG

ADLSGVTEEAPLKLSKAVHKAVLTIDEKGTEAAGAMFLEAIPMSI

PPEVKFNKPFVFLMIEQNTKSPLFMGKVVNPTQKERKCCVECPPC

*PAPPVAGPSVFLFPPKPKDTLMISRTPEVTCVVVDVSHEDPEVQF*

*NWYVDGVEVHNAKTKPREEQFNSTFRVVSVLTVVHQDWLNGKEYK*

*CKVSNKGLPAPIEKTISKTKGQPREPQVYTLPPSREEMTKNQVSL*

*TCLVKGFYPSDIAVEWESNGQPENNYKTTPPMLDSDGSFFLYSKL*

*TVDKSRWQQGNVFSCSVMHEALHNHYTQKSLSLSPGK*

An exemplary AAT-Fc fusion protein is the AAT-MM-EL-hFc1 (human IgG1 Fc, Met351Glu/Met358Leu), described herein. As shown below, AAT polypeptide portion of the fusion protein is underlined (SEQ ID NO: 34), the hinge region is shown in normal text (SEQ ID NO: 43), the IgG-Fc polypeptide portion of the fusion protein is italicized (SEQ ID NO: 3), and the Met351Glu mutation is boxed, and the Met358Leu mutation is shaded in grey.

AAT-MM-EL-hFc1(human IgG1 Fc, Met351Glu/Met358Leu)
(SEQ ID NO: 18)

EDPQGDAAQKTDTSHHDQDHPTFNKITPNLAEFAFSLYRQLAHQSNSTNIFFSPVSIATAFAML

SLGTKADTHDEILEGLNFNLTEIPEAQIHEGFQELLRTLNQPDSQLQLTTGNGLFLSEGLKLVD

KFLEDVKKLYHSEAFTVNFGDTEEAKKQINDYVEKGTQGKIVDLVKELDRDTVFALVNYIFFKG

KWERPFEVKDTEEEDFHVDQVTTVKVPMMKRLGMFNIQHCKKLSSWVLLMKYLGNATAIFFLPD

EGKLQHLENELTHDIITKFLENEDRRSASLHLPKLSITGTYDLKSVLGQLGITKVFSNGADLSG

VTEEAPLKLSKAVHKAVLTIDEKGTEAAGAEFLEAIPLSIPPEVKFNKPFVFLMIEQNTKSPLF

MGKVVNPTQK*EPKSCDKTHTCPPCPAPELLGGPSVFLFPPKPKDTLMISRTPEVTCVVVDVSHE*

*DPEVKFNWYVDGVEVHNAKTKPREEQYNSTYRVVSVLTVLHQDWLNGKEYKCKVSNKALPAPIE*

*KTISKAKGQPREPQVYTLPPSRDELTKNQVSLTCLVKGFYPSDIAVEWESNGQPENNYKTTPPV*

*LDSDGSFFLYSKLTVDKSRWQQGNVFSCSVMHEALHNHYTQKSLSLSPGK*

An exemplary AAT-Fc fusion protein is the AAT-MM-EL-hFc2 (human IgG2 Fc, Met351Glu/Met358Leu), described herein. As shown below, AAT polypeptide portion of the fusion protein is underlined (SEQ ID NO: 34), the hinge region is shown in normal text (SEQ ID NO: 44), the IgG-Fc polypeptide portion of the fusion protein is italicized (SEQ ID NO: 4), the Met351Glu mutation is boxed, and the Met358Leu mutation is shaded in grey.

AAT-MM-EL-hFc2(human IgG2 Fc, Met351Glu/Met358Leu)
(SEQ ID NO: 19)

EDPQGDAAQKTDTSHHDQDHPTFNKITPNLAEFAFSLYRQLAHQSNSTNIFFSPVSIATAFAML

SLGTKADTHDEILEGLNFNLTEIPEAQIHEGFQELLRTLNQPDSQLQLTTGNGLFLSEGLKLVD

KFLEDVKKLYHSEAFTVNFGDTEEAKKQINDYVEKGTQGKIVDLVKELDRDTVFALVNYIFFKG

KWERPFEVKDTEEEDFHVDQVTTVKVPMMKRLGMFNIQHCKKLSSWVLLMKYLGNATAIFFLPD

EGKLQHLENELTHDIITKFLENEDRRSASLHLPKLSITGTYDLKSVLGQLGITKVFSNGADLSG

VTEEAPLKLSKAVHKAVLTIDEKGTEAAGAEFLEAIPLSIPPEVKFNKPFVFLMIEQNTKSPLF

MGKVVNPTQK*ERKCCVECPPCPAPPVAGPSVFLFPPKPKDTLMISRTPEVTCVVVDVSHEDPEV*

*QFNWYVDGVEVHNAKTKPREEQFNSTFRVVSVLTVVHQDWLNGKEYKCKVSNKGLPAPIEKTIS*

*KTKGQPREPQVYTLPPSREEMTKNQVSLTCLVKGFYPSDIAVEWESNGQPENNYKTTPPMLDSD*

*GSFFLYSKLTVDKSRWQQGNVFSCSVMHEALHNHYTQKSLSLSPGK*

An exemplary AAT-Fc fusion protein is the AAT-MM-LL-hFc1 (human IgG1 Fc, Met351Leu/Met358Leu), described herein. As shown below, AAT polypeptide portion of the fusion protein is underlined (SEQ ID NO: 35), the hinge region is shown in normal text (SEQ ID NO: 43), the IgG-Fc polypeptide portion of the fusion protein is italicized (SEQ ID NO: 3), the Met351Leu mutation is shaded in black, and the Met358Leu mutation is shaded in grey.

AAT-MM-LL-hFc1(human IgG1 Fc, Met351Leu/Met358Leu)
(SEQ ID NO: 36)

EDPQGDAAQKTDTSHHDQDHPTFNKITPNLAEFAFSLYRQLAHQSNSTNIFFSPVSIATAFAML

SLGTKADTHDEILEGLNFNLTEIPEAQIHEGFQELLRTLNQPDSQLQLTTGNGLFLSEGLKLVD

KFLEDVKKLYHSEAFTVNFGDTEEAKKQINDYVEKGTQGKIVDLVKELDRDTVFALVNYIFFKG

KWERPFEVKDTEEEDFHVDQVTTVKVPMMKRLGMFNIQHCKKLSSWVLLMKYLGNATAIFFLPD

EGKLQHLENELTHDIITKFLENEDRRSASLHLPKLSITGTYDLKSVLGQLGITKVFSNGADLSG

VTEEAPLKLSKAVHKAVLTIDEKGTEAAGALFLEAIPLSIPPEVKFNKPFVFLMIEQNTKSPLF

MGKVVNPTQK*ERKSCDKTHTCPPCPAPELLGGPSVFLFPPKPKDTLMISRTPEVTCVVVDVSHE*

-continued

*DPEVKFNWYVDGVEVHNAKTKPREEQYNSTYRVVSVLTVLHQDWLNGKEYKCKVSNKALPAPIE*

*KTISKAKGQPREPQVYTLPPSRDELTKNQVSLTCLVKGFYPSDIAVEWESNGQPENNYKTTPPV*

*LDSDGSFFLYSKLTVDKSRWQQGNVFSCSVMHEALHNHYTQKSLSLSPGK*

An exemplary AAT-Fc fusion protein is the AAT-MM: LL-hFc2(human IgG2 Fc, Met351Leu/Met358Leu), described herein. As shown below, AAT polypeptide portion of the fusion protein is underlined (SEQ ID NO: 35), the hinge region is shown in normal text (SEQ ID NO: 44) the IgG-Fc polypeptide portion of the fusion protein is italicized (SEQ ID NO: 4), the Met351Leu mutation is shaded in black, and the Met358Leu mutation is shaded in grey.

AAT-MM:LL-hFc2(human IgG2 Fc, Met351Leu/Met358Leu)
(SEQ ID NO: 20)

EDPQGDAAQKTDTSHHDQDHPTFNKITPNLAEFAFSLYRQLAHQSNSTNIFFSPVSIATAFAML

SLGTKADTHDEILEGLNFNLTEIPEAQIHEGFQELLRTLNQPDSQLQLTTGNGLFLSEGLKLVD

KFLEDVKKLYHSEAFTVNFGDTEEAKKQINDYVEKGTQGKIVDLVKELDRDTVFALVNYIFFKG

KWERPFEVKDTEEEDFHVDQVTTVKVPMMKRLGMFNIQHCKKLSSWVLLMKYLGNATAIFFLPD

EGKLQHLENELTHDIITKFLENEDRRSASLHLPKLSITGTYDLKSVLGQLGITKVFSNGADLSG

VTEEAPLKLSKAVHKAVLTIDEKGTEAAGALFLEAIPLSIPPEVKFNKPFVFLMIEQNTKSPLF

*MGKVVNPTQKERKCCVECPPCPAPPVAGPSVFLFPPKPKDTLMISRTPEVTCVVVDVSHEDPEV*

*QFNWYVDGVEVHNAKTKPREEQFNSTFRVVSVLTVVHQDWLNGKEYKCKVSNKGLPAPIEKTIS*

*KTKGQPREPQVYTLPPSREEMTKNQVSLTCLVKGFYPSDIAVEWESNGQPENNYKTTPPMLDSD*

*GSFFLYSKLTVDKSRWQQGNVFSCSVMHEALHNHYTQKSLSLSPGK*

An exemplary AAT-Fc fusion protein is the AAT-hFc1-AAT (human IgG1), described herein. As shown below, AAT polypeptide portion of the fusion protein is underlined (SEQ ID NO: 2), the hinge region is shown in normal text (SEQ ID NO: 43), the ASTGS linker is shown in normal text (SEQ ID NO: 45), and the IgG-Fc polypeptide portion of the fusion protein is italicized (SEQ ID NO: 3).

AAT-hFc1-AAT (human IgG1)
(SEQ ID NO: 21)

EDPQGDAAQKTDTSHHDQDHPTFNKITPNLAEFAFSLYRQLAHQS

NSTNIFFSPVSIATAFAMLSLGTKADTHDEILEGLNFNLTEIPEA

QIHEGFQELLRTLNQPDSQLQLTTGNGLFLSEGLKLVDKFLEDVK

KLYHSEAFTVNFGDTEEAKKQINDYVEKGTQGKIVDLVKELDRDT

VFALVNYIFFKGKWERPFEVKDTEEEDFHVDQVTTVKVPMMKRLG

MFNIQHCKKLSSWVLLMKYLGNATAIFFLPDEGKLQHLENELTHD

IITKFLENEDRRSASLHLPKLSITGTYDLKSVLGQLGITKVFSNG

ADLSGVTEEAPLKLSKAVHKAVLTIDEKGTEAAGAMFLEAIPMSI

PPEVKFNKPFVFLMIEQNTKSPLFMGKVVNPTQKEPKSCDKTHTC

*PPCPAPELLGGPSVFLFPPKPKDTLMISRTPEVTCVVVDVSHEDP*

*EVKFNWYVDGVEVHNAKTKPREEQYNSTYRVVSVLTVLHQDWLNG*

*KEYKCKVSNKALPAPIEKTISKAKGQPREPQVYTLPPSRDELTKN*

*QVSLTCLVKGFYPSDIAVEWESNGQPENNYKTTPPVLDSDGSFFL*

-continued

*YSKLTVDKSRWQQGNVFSCSVMHEALHNHYTQKSLSLSPGK*ASTG

SEDPQGDAAQKTDTSHHDQDHPTFNKITPNLAEFAFSLYRQLAHQ

SNSTNIFFSPVSIATAFAMLSLGTKADTHDEILEGLNFNLTEIPE

AQIHEGFQELLRTLNQPDSQLQLTTGNGLFLSEGLKLVDKFLEDV

KKLYHSEAFTVNFGDTEEAKKQINDYVEKGTQGKIVDLVKELDRD

TVFALVNYIFFKGKWERPFEVKDTEEEDFHVDQVTTVKVPMMKRL

GMFNIQHCKKLSSWVLLMKYLGNATAIFFLPDEGKLQHLENELTH

DIITKFLENEDRRSASLHLPKLSITGTYDLKSVLGQLGITKVFSN

GADLSGVTEEAPLKLSKAVHKAVLTIDEKGTEAAGAMFLEAIPMS

IPPEVKFNKPFVFLMIEQNTKSPLFMGKVVNPTQK

These exemplary AAT-Fc fusion proteins were made using the following techniques.

The gene encoding human AAT was PCR amplified from human liver cDNA (Zyagen). Specific point mutations within the gene encoding AAT or the Fc region were generated by overlapping PCR. The AAT encoding gene was cloned in frame with a gene encoding the hinge region, followed by a CH2 domain, and a CH3 domain of human IgG1, IgG2, IgG3, IgG4, or IgM into a mammalian expression vector, containing a mammalian secretion signal sequence up stream of the AAT gene insertion site. These expression vectors were transfected into mammalian cells (specifically HEK293 or CHO cells) and grown for several days in 8% $CO_2$ at 37° C. The recombinant AAT-Fc fusion proteins were purified from the expression cell supernatant by protein A chromatography. Importantly, a near neutral pH buffer was used (Gentle Ag/Ab Elution Buffer, Thermo Scientific) to elute the AAT-Fc fusion protein from the protein A resin. The AAT-Fc fusion protein can not be eluted from protein A resin using a standard low pH elution, as the ability of AAT to inhibit NE is compromised following low pH treatment, likely due to a low pH mediated oligomerization of AAT. FIG. 1F shows the effects of low pH elution on the ability of AAT to inhibit neutrophil elastase. AAT-Fc fusion protein can be purified either by protein A and a near neutral pH elution buffer, by CaptureSelect® Alpha-1 Antitrypsin affinity matrix (BAC BV).

The purified AAT-Fc fusion proteins were tested for activity by determining their ability to inhibit neutrophil elastase (NE). FIGS. 1B and 1D show a reducing SDS-PAGE gel of purified serum derived AAT (sdAAT) and AAT-Fc fusion proteins (FIG. 1B-lane 1: sdAAT, lane 2: AAT-Fc (SEQ ID NO: 16), lane 3: AAT-EL-Fc (SEQ ID NO: 18), FIG. 1D AAT-Fc-AAT (SEQ ID NO: 20). The proteins were visualized by staining with coomassie blue.

To monitor human Neutrophil Elastase (NE) activity a fluorescent microplate assay was used. Inhibitory activity was measured by a concomitant decrease in the residual NE activity using the following assay. This assay buffer is composed of 100 mM Tris pH 7.4, 500 mM NaCl, and 0.0005% Triton X-100. Human NE is used at a final concentration of 5 nM (but can also be used from 1-20 nM). The fluorescent peptide substrate AAVP-AMC is used at a final concentration of 100 µM in the assay. The Gemini EM plate reader from Molecular Devices is used to read the assay kinetics using excitation and emission wavelengths of 370 nm and 440 nm respectively, and a cutoff of 420 nm. The assay is read for 10 min at room temperature scanning every 5 to 10 seconds. The Vmax per second corresponds to the residual NE activity, which is plotted for each concentration of inhibitor. The intercept with the x-axis indicates the concentration of inhibitor needed to fully inactivate the starting concentration of NE in the assay. Human serum derived AAT (sdAAT) was used as a positive control in these assays. The AAT-Fc fusion proteins display potent NE inhibitory activity as shown in FIG. 1C. The fusion wherein there are two AAT polypeptides fused to single Fc polypeptide (AAT-Fc-AAT) displays enhanced potency over both sdAAT and the AAT-Fc fusion protein comprising a single AAT polypeptide (FIG. 1E). These findings presented here demonstrate for the first time the AAT can be fused to an Fc region and maintain its ability to inhibit NE. Of particular interest, the AAT-Fc-AAT fusion protein was found to be a more potent NE inhibitor.

FIG. 1F demonstrates the resistance of the AAT-EL-Fc (M351E, M358L) fusion protein to inactivation by oxidation. AAT fusion proteins, AAT-Fc (wt), AAT-EL-Fc (M351E, M358L), and AAT-EM-Fc (M351E), were treated with 33 mM $H_2O_2$ and compared to untreated fusion proteins in the NE inhibition assays. The inhibition of NE by AAT-EL-Fc was not comprised by oxidation, converse to the other proteins tested.

Figure 1H:
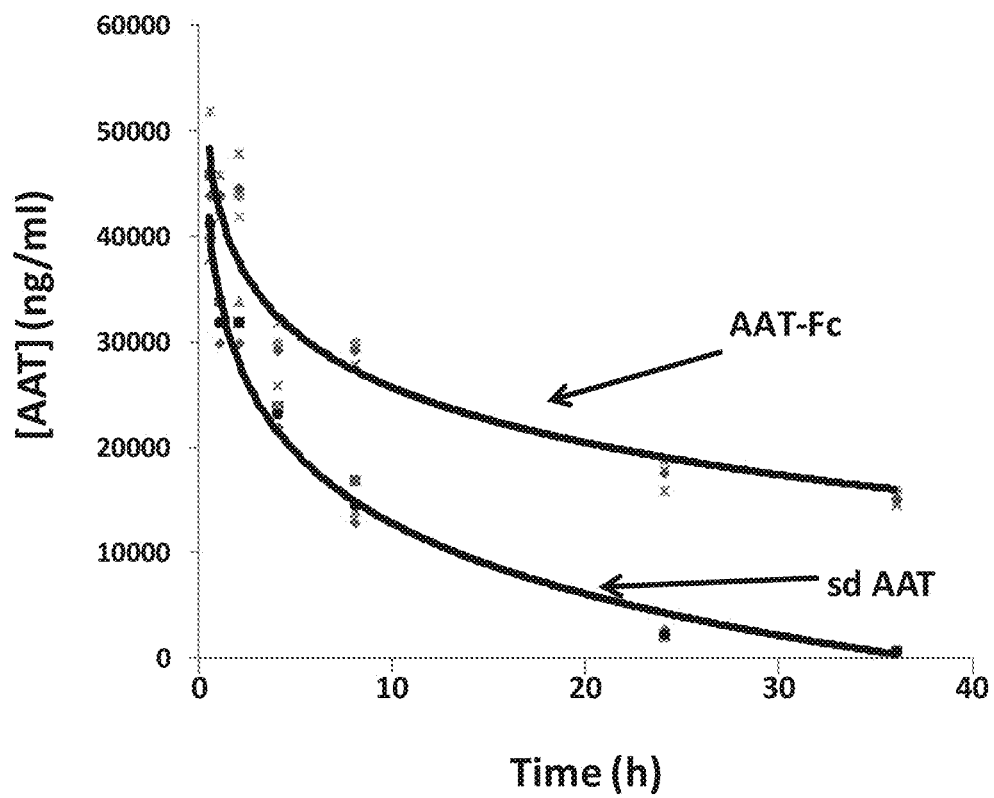
FIG. 1H is a graph depicting the serum clearance rates of serum derived AAT (sdAAT) compared to AAT-Fc in rats dosed with 10 mg/kg protein (3 rats/test protein). The half-life of AAT-Fc is substantially longer than that of sdAAT.

Furthermore, AAT-Fc fusion protein displayed a longer serum half-life in rats compared to serum derived AAT (FIG. 1H). In these studies 3 rats per each test protein were injected I.V. with 10 mg/kg of sdAAT or AAT-Fc. Serum sample were taken at various time points over a 48 period. The serum ATT concentration was using an ELISA. These findings demonstrate that the fusion proteins of the invention have improved pharmacokinetic properties and are a superior therapeutic format over serum derived AAT, for treating numerous human inflammatory conditions and infectious diseases.

Example 2: AAT-TNFα Targeting Molecule Fusion Proteins

The studies presented herein describe several, non-limiting examples of recombinant AAT derivatives comprising human AAT fused to an anti-TNFα antibody or a derivative of a TNFα receptor. These examples are provided below to further illustrate different features of the present invention. The examples also illustrate useful methodology for practicing the invention. These examples do not and are not intended to limit the claimed invention.

The fusion proteins below include cytokine targeting polypeptide sequences that are from or are derived from (i) the anti-TNFα antibody D2E7 (also known as Adalimumab or Humira®), or (ii) the extracellular domain of Type 2 TNFα Receptor (TNFR2-ECD). The AAT polypeptide portion of the fusion protein is underlined, the antibody constant regions (CH1-hinge-CH2-CH3, or CL) are italicized, and D2E7-VH, D2E7-VK, and TNFR2-ECD are denoted in bold text. While these examples include a hinge sequence and/or a linker sequence, fusion proteins of the invention can be made using any hinge sequence and/or a linker sequence suitable in length and/or flexibility. Alternatively fusion proteins can be made without using a hinge and/or a linker sequence.

An exemplary AAT-TNFα fusion protein is D2E7-Light Chain-AAT $(G_3S)_2$ Linker, described herein. As shown below, the AAT polypeptide portion of the fusion protein is underlined (SEQ ID NO: 2), D2E7-VK is denoted in bold text (SEQ ID NO: 37), the $(G_3S)_2$ linker is shown in normal text (SEQ ID NO: 46), and the antibody constant regions are italicized (SEQ ID NO: 38)

```
D2E7-Light Chain-AAT (G₃S)₂ Linker
                                     (SEQ ID NO: 22)
DIQMTQSPSSLSASVGDRVTITCRASQGIRNYLAWYQQKPGKAPK

LLIYAASTLQSGVPSRFSGSGSGTDFTLTISSLQPEDVATYYCQR

YNRAPYTFGQGTKVEIKRTVAAPSVFTFPPSDFCLKSGTASVVCL

LNNFYPREAKVQWKVDNALQSGNSQESVTEQDSKDSTYSLSSTLT

LSKADYEKHKVYACEVTHQGLSSPVTKSFNRGECGGGSGGGSEDP

QGDAAQKTDTSHHDQDHPTFNKITPNLAEFAFSLYRQLAHQSNST

NIFFSPVSIATAFAMLSLGTKADTHDEILEGLNFNLTEIPEAQIH

EGFQELLRTLNQPDSQLQLTTGNGLFLSEGLKLVDKFLEDVKKLY

HSEAFTVNFGDTEEAKKQINDYVEKGTQGKIVDLVKELDRDTVFA

LVNYIFFKGKWERPFEVKDTEEEDFHVDQVTTVKVPMMKRLGMFN

IQHCKKLSSWVLLMKYLGNATAIFFLPDEGKLQHLENELTHDIIT

KFLENEDRRSASLHLPKLSITGTYDLKSVLGQLGITKVFSNGADL

SGVTEEAPLKLSKAVHKAVLTIDEKGTEAAGAMFLEAIPMSIPPE

VKFNKPFVFLMIEQNTKSPLFMGKWNPTQK
```

An exemplary AAT-TNFα0 fusion protein is D2E7-Light Chain-AAT ASTGS Linker, described herein. As shown below, the AAT polypeptide portion of the fusion protein is underlined (SEQ ID NO: 2), D2E7-VK is denoted in bold text (SEQ ID NO: 37), the ASTGS linker is shown in normal text (SEQ ID NO: 45), and the antibody constant regions is italicized (SEQ ID NO: 38)

```
D2E7-Light Chain-AAT ASTGS Linker
                                     (SEQ ID NO: 23)
DIQMTQSPSSLSASVGDRVTITCRASQGIRNYLAWYQQKPGKAPK

LLIYAASTLQSGVPSRFSGSGSGTDFTLTISSLQPEDVATYYCQR
```

```
YNRAPYTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGECASTGSEDPQGD

AAQKTDTSHHDQDHPTFNKITPNLAEFAFSLYRQLAHQSNSTNIF

FSPVSIATAFAMLSLGTKADTHDEILEGLNFNLTEIPEAQIHEGF

QELLRTLNQPDSQLQLTTGNGLFLSEGLKLVDKFLEDVKKLYHSE

AFTVNFGDTEEAKKQINDYVEKGTQGKIVDLVKELDRDTVFALVN

YIFFKGKWERPFEVKDTEEEDFHVDQVTTVKVPMMKRLGMFNIQH

CKKLSSWVLLMKYLGNATAIFFLPDEGKLQHLENELTHDIITKFL

ENEDRRSASLHLPKLSITGTYDLKSVLGQLGITKVFSNGADLSGV

TEEAPLKLSKAVHKAVLTIDEKGTEAAGAMFLEAIPMSIPPEVKF

NKPFVFLMIEQNTKSPLFMGKVVNPTQK
```

An exemplary AAT-TNFα fusion protein is D2E7-Heavy Chain-AAT (G₃S)₂ Linker, described herein. As shown below, the AAT polypeptide portion of the fusion protein is underlined (SEQ ID NO: 2), D2E7-VH is denoted in bold text (SEQ ID NO: 39), the (G₃S)₂ linker is shown in normal text (SEQ ID NO: 46), and the antibody constant regions is italicized (SEQ ID NO: 40)

```
D2E7-Heavy Chain-AAT (G3S)2 Linker
                                      (SEQ ID NO: 24)
EVQLVESGGGLVQPGRSLRLSCAASGFTFDDYAMHWVRQAPGKGL

EWVSAITWNSGHIDYADSVEGRFTISRDNAKNSLYLQMNSLRAED

TAVYYCAKVSYLSTASSLDYWGQGTLVTVSSASTKGPSVFPLAPS

SKSTSGGTAALGCLVKDYFPEPVTVSWNSGALTSGVHTFPAVLQS

SGLYSLSSVVTVPSSSLGTQTYICNVNHKPSNTKVDKKVEPKSCD

KTHTCPPCPAPELLGGPSVFLFPPKPKDTLMISRTPEVTCVVVDV

SHEDPEVKFNWYVDGVEVHNAKTKPREEQYNSTYRVVSVLTVLHQ

DWLNGKEYKCKVSNKALPAPIEKTISKAGQPREPQVYTLPPSRD

ELTKNQVSLTCLVKGFYPSDIAVEWESNGQPENNYKTTPPVLDSD

GSFFLYSKLTVDKSRWQQGNVFSCSVMHEALHNHYTQKSLSLSPG

KGGGSGGGSEDPQGDAAQKTDTSHHDQDHPTFNKITPNLAEFAFS

LYRQLAHQSNSTNIFFSPVSIATAFAMLSLGTKADTHDEILEGLN

FNLTEIPEAQIHEGFQELLRTLNQPDSQLQLTIGNGLFLSEGLKL

VDKFLEDVKKLYHSEAFTVNFGDTEEAKKQINDYVEKGTQGKIVD

LVKELDRDTVFALVNYIFFKGKWERPFEVKDTEEEDFHVDQVTTV

KVPMMKRLGMFNIQHCKKLSSWVLLMKYLGNATAIFFLPDEGKLQ

HLENELTHDIITKFLENEDRRSASLHLPKLSITGTYDLKSVLGQL

GITKVFSNGADLSGVTEEAPLKLSKAVHKAVLTIDEKGTEAAGAM

FLEAIPMSIPPEVKFNKPFVFLMIEQNTKSPLFMGKVVNPTQK
```

An exemplary AAT-TNFα fusion protein is D2E7-Heavy Chain-AAT ASTGS Linker, described herein. As shown below, the AAT polypeptide portion of the fusion protein is underlined (SEQ ID NO: 2), D2E7-VH is denoted in bold text (SEQ ID NO: 39), the ASTGS linker is shown in normal text (SEQ ID NO: 45), and the antibody constant regions is italicized (SEQ ID NO: 40)

```
D2E7-Heavy Chain-AAT ASTGS Linker
                                      (SEQ ID NO: 25)
EVQLVESGGGLVQPGRSLRLSCAASGFTFDDYAMHWVRQAPGKGL

EWVSAITWNSGHIDYADSVEGRFTISRDNAENSLYLQMNSLRAED

TAVYYCAKVSYLSTASSLDYWGQGTLVTVSSASTKGPSVFPLAPS

SKSTSGGTAALGCLVKDYFREPVTVSWNSGALTSGVHTFPAVLQS

SGLYSLSSVVTVPSSSLGTQTYICNVNHKPSNTKVDKKVERKSCD

KTHTCPPCPAPELLGGPSVFLFPPKPKDTLMISRTPEVTCVVVDV

SHEDPEVKFNWYVDGVEVENAKTKPREEQYNSTYRVVSVLTVLHQ

DWLNGKEYKCKVSNKALPAPIEKTISKAKGQPREPQVYTLPPSRD

ELTKNQVSLTCLVKGFYPSDIAVEWESNGQPENNYKTTPPVLDSD

GSFFLYSKLTVDKSRWQQGNVFSCSVMHEALHNHYTQKSLSLSPG

KASTGSEDPQGDAAQKTDTSHHDQDHPTFNKITPNLAEFAFSLYR

QLAHQSNSTNIFFSPVSIATAFAMLSLGTKADTHDEILEGLNFNL

TEIPEAQIHEGFQELLRTLNQPDSQLQLTTGNGLFLSEGLKLVDK

FLEDVKKLYHSEAFTVNFGDTEEAKKQINDYVEKGTQGKIVDLVK

ELDRDTVFALVNYIFFKGKWERPFEVKDTEEEDFHVDQVTTVKVP

MMKRLGMFNIQHCKKLSSWVLLMKYLGNATAIFFLPDEGKLQHLE

NELTHDIITKFLENEDRRSASLHLPKLSITGTYDLKSVLGQLGIT

KVFSNGADLSGVTEEAPLKLSKAVHKAVLTIDEKGTEAAGAMFLE

AIPMSIPPEVKFNKPFVFLMIEQNTKSPLFMGKVVNPTQK
```

An exemplary AAT-TNFα fusion protein is TNFR2-ECD-Fc1-AAT(G₃S)₂ Linker, described herein. As shown below, the AAT polypeptide portion of the fusion protein is underlined (SEQ ID NO: 2), TNFR2-ECD is denoted in bold text (SEQ ID NO: 41), the hinge region is shown in normal text (SEQ ID NO: 43), the (G₃S)₂ linker is shown in normal text (SEQ ID NO: 46), and the antibody constant regions is italicized (SEQ ID NO: 42)

```
TNFR2-ECD-Fc1-AAT(G3S)2 Linker
                                      (SEQ ID NO: 26)
LPAQVAFTPYAPEPGSTCRLREYYDQTAQMCCSKCSPGQHAKVF

CTKTSDTVCDSCEDSTYTQLWNWVPECLSCGSRCSSDQVETQAC

TREQNRICTCRPGWYCALSKQEGCRLCAPLRKCRPGFGVARPGT

ETSDVVCKPCAPGTFSNTTSSTDICRPHQICNVVAIPGNASMDA

VCTSTSPTRSMAPGAVHLPQPVSTRSQHTQPTPEPSTAPSTSFL

LPMGPSPPAEGSTGDEPKSCDKTHTCPPCPAPKLLGGPSVFLFP

PKPKDTLMISRTPEVTCVVVDVSHEDPQVKFNWYVDGVQVHNAK

TKPREQQYNSTYRVVSVLTVLHQNWLDGKEYKCKVSNKALPAPI

EKTISKAKGQPREPQVYTLPPSREEMTKNQVSLTCLVKGFYPSD

IAVEWESNGQPENNYKTTPPVLDSDGSFFLYSKLTVDKSRWQQG

NVFSCSVMHEALHNHYTQKSLSLSPGKGGGSGGGSEDPQGDAAQ
```

-continued

KTDTSHHDQDHPTFNKITPNLAEFAFSLYRQLAHQSNSTNIFFS

PVSIATAFAMLSLGTKADTHDEILEGLNFNLTEIPEAQIHEGFQ

ELLRTLNQPDSQLQLTTGNGLFLSEGLKLVDKFLEDVKKLYHSE

AFTVNFGDTEEAKKQINDYVEKGTQGKIVDLVKELDRDTVFALV

NYIFFKGKWERPFEVKDTEEEDFHVDQVTTVKVPMMKRLGMFNI

QHCKKLSSWVLLMKYLGNATAIFFLPDEGKLQHLENELTHDIIT

KFLENEDRRSASLHLPKLSITGTYDLKSVLGQLGITKVFSNGAD

LSGVTEEAPLKLSKAVHKAVLTIDEKGTEAAGAMFLEAIPMSIP

PEVKFNKPFVFLMIEQNTKSPLFMGKWNPTQK

An exemplary AAT-TNFα fusion protein is TNFR2-ECD-Fc1-AAT ASTGS Linker, described herein. As shown below, the AAT polypeptide portion of the fusion protein is underlined (SEQ ID NO: 2), TNFR2-ECD is denoted in bold text (SEQ ID NO: 41), the hinge region is shown in normal text (SEQ ID NO: 43), the ASTGS linker is shown in normal text (SEQ ID NO: 45), and the antibody constant regions is italicized (SEQ ID NO: 42)

TNFR2-ECD-Fc1-AAT ASTGS Linker
(SEQ ID NO: 27)
LPAQVAFTPYAPEPGSTCRLREYYDQTAQMCCSKCSPGQHAK

VFCTKTSDTVCDSCEDSTYTQLWNWVPECLSCGSRCSSDQVE

TQACTREQNRICTCRPGWYCALSKQEGCRLCAPLRKCRPGFG

VARPGTETSDVVCKPCAPGTFSNTTSSTDICRPHQICNVVAI

PGNASMDAVCTSTSPTRSMAPGAVHLPQPVSTRSQHTQPTPE

PSTAPSTSFLLPMGPSPPAEGSTGDEPKSCDKTHTCPPCPAP

ELLGGPSVFLFPPKPKDTLMISRTPEVTCVVVDVSREDPQVK

FNWYVDGVQVHNAKTKPREQQYNSTYRVVSVLTVLHQNWLDG

KEYKCKVSNKALPAPIEKTISKAKGQPREPQVYTLPPSREEM

TKNQVSLTCLVKGFYPSDIAVEWESNGQPENNYKTTPPVLDS

DGSFFLYSKLTVDKSRWQQGNVFSCSVMREALHNHYTQKSLS

LSPGKASTGSEDPQGDAAQKTDTSHHDQDHPTFNKITPNLAE

FAFSLYRQLAHQSNSTNIFFSPVSIATAFAMLSLGTKADTHD

EILEGLNFNLTEIPEAQIHEGFQELLRTLNQPDSQLQLTTGN

GLFLSEGLKLVDKFLEDVKKLYHSEAFTVNFGDTEEAKKQIN

DYVEKGTQGKIVDLVKELDRDTVFALVNYIFFKGKWERPFEV

KDTEEEDFHVDQVTTVKVPMMKRLGMFNIQHCKKLSSWVLLM

KYLGNATAIFFLPDEGKLQHLENELTHDIITKFLENEDRRSA

SLHLPKLSITGTYDLKSVLGQLGITKVFSNGADLSGVTEEAP

LKLSKAVHKAVLTIDEKGTEAAGAMFLEAIPMSIPPEVKFNK

PFVFLMIEQNTKSPLFMGKVVNPTQK

These exemplary AAT-TNFα targeting molecule fusion proteins were made using the following techniques.

The genes encoding the variable heavy (VH) and variable kappa (VK) regions of the anti-TNFα antibody, D2E7, were generated by gene synthesis. The D2E7-VH gene was cloned in frame with a gene encoding a human IgG1 antibody heavy chain constant region, consisting of a CH1 domain, a hinge domain, a CH2 domain, and a CH3 domain, into a mammalian expression vector, containing a mammalian secretion signal sequence up stream of the VH domain insertion site (D2E7-HC). The D2E7-VK gene was cloned in frame with a human antibody kappa light chain constant (CL) domain, into a mammalian expression vector, containing a mammalian secretion signal sequence up stream of the VK domain insertion site (D2E7-LC). The AAT encoding gene and the adjacent 5' linker sequence were cloned in frame into the 3' end of either, the CH3 domain of the D2E7 heavy chain gene (D2E7-HC-AAT), or the CL domain of the D2E7 light chain gene (D2E7-LC-AAT) coding sequences in the above described mammalian expression vectors. The extracellular domain of the TNFα Receptor 2 (TNFR2-ECD) was generated by gene synthesis and cloned in frame with a gene encoding the hinge region, followed by a CH2 domain and a CH3 domain of human IgG1 (hFc1) into a mammalian expression, containing a mammalian secretion signal sequence up stream of the TNFR2-ECD insertion site. The AAT encoding gene and the adjacent 5' linker sequence were cloned in frame into the 3' end of the gene encoding TNFR2-ECD-hFc1 into a mammalian expression vector (TNFR2-ECD-hFc1-AAT).

The D2E7-HC-AAT expression vector was co-transfected with either the D2E7-LC or the D2E7-LC-AAT expression vector into mammalian cells (specifically HEK293 or CHO cells) to generate the D2E7 antibody with AAT fused to the C-terminus of the heavy chain or to the C-terminus of both the heavy chain and light chain, respectively. The D2E7-LC-AAT was co-transfected with the D2E7-HC expression vector into mammalian cells to generate the D2E7 antibody with AAT fused to the C-terminus of the light chain. The TNFR2-hFc1-AAT expression vector was transfected into mammalian cells. Transfected cells were grown for several days in 8% CO2 at 37° C.

The recombinant AAT-TNFα targeting fusion proteins were purified from the expression cell supernatant by protein A chromatography. A near neutral pH buffer was used (Gentle Ag/Ab Elution Buffer, Thermo Scientific) to elute the AAT-TNFα targeting fusion proteins from the protein A resin.

Figure 2A:
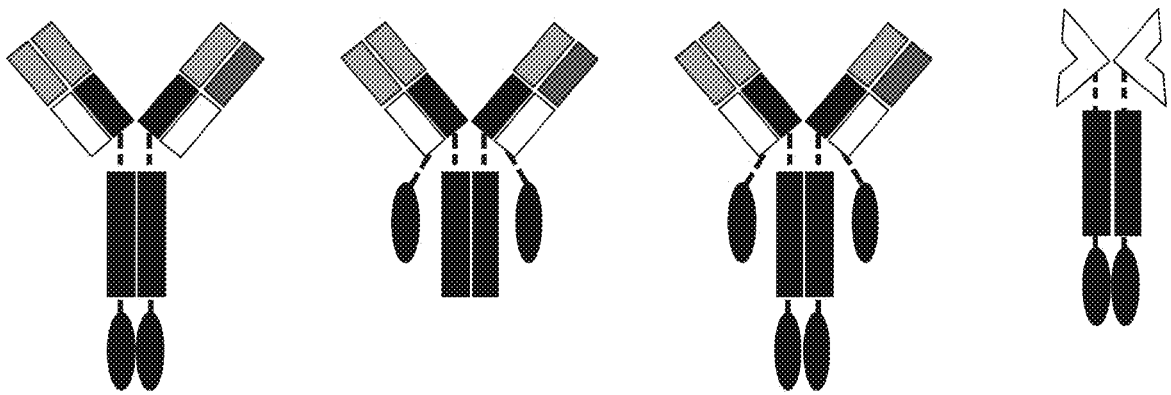
FIG. 2A is a schematic representation of some embodiments of the serpin-cytokine targeting fusion proteins of the invention. The serpin can be fused to either the heavy chain, the light chain, or both of an antibody. Serpin-cytokine receptor fusion proteins are also depicted.
Figure 2B:
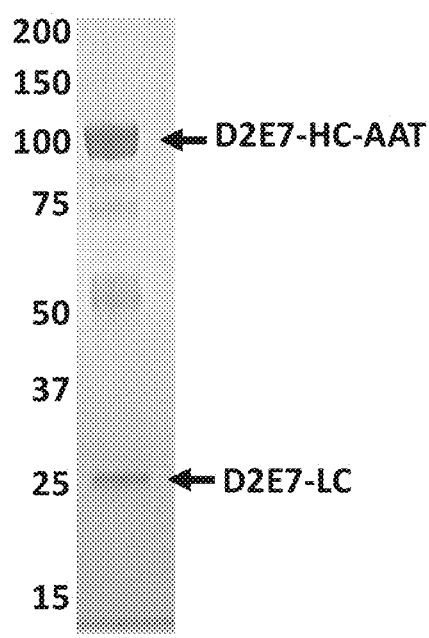
FIG. 2B is a photograph of a SDS-PAGE gel showing the D2E7 antibody (lane 1), and the D2E7 antibody with-AAT fused to heavy chain (lane 2).

FIG. 2B shows an SDS-PAGE gel of the D2E7 antibody alone (lane 1) and variant wherein AAT is fused to the heavy chain of D2E7 (lane 2). The proteins were visualized by staining with coomassie blue.

Figure 2C:
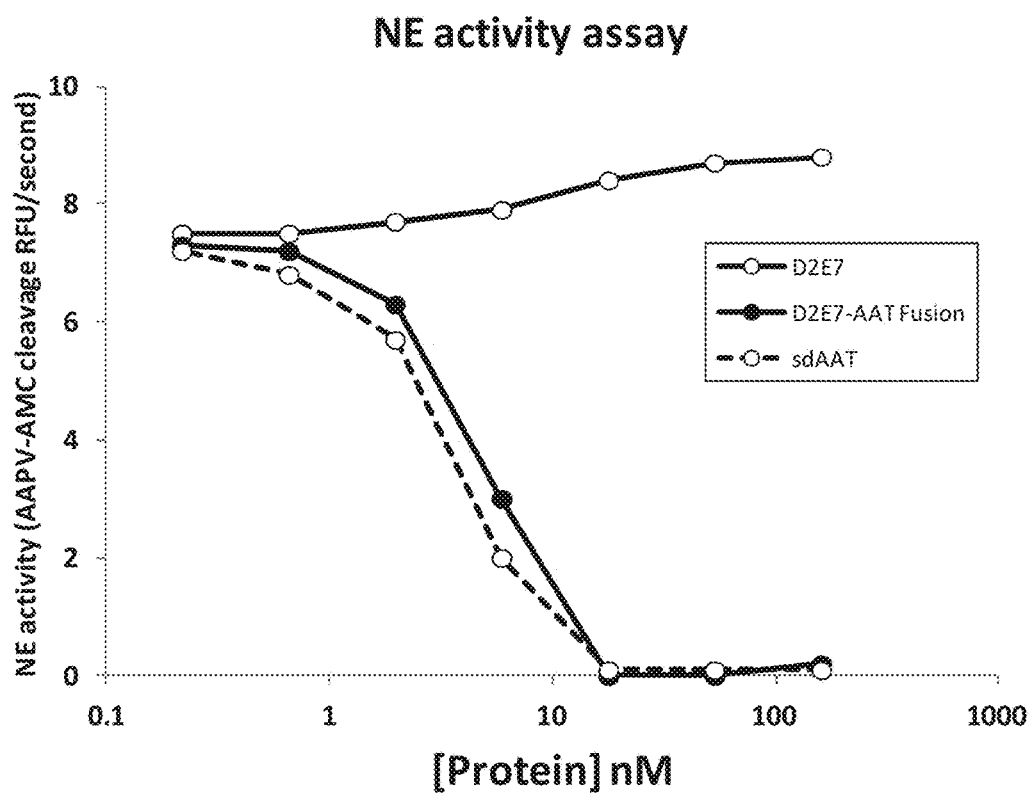
FIG. 2C is a graph showing the inhibition of neutrophil elastase activity by a D2E7 antibody fused to AAT. Serum derived AAT is shown as a positive control, whereas the D2E7 antibody alone is shown as a negative control for NE inhibition.

The purified AAT-TNFα targeting molecule fusion proteins were tested for activity by determining their ability to inhibit neutrophil elastase. Human serum derived AAT (sdAAT) was used as a positive control in these assays. NE inhibitory assay were conducted as described above. FIG. 2C demonstrates relative to sdAAT, the AAT-TNFα targeting molecule fusion protein shows similar inhibition of neutrophil elastase, indicating that the inhibitory capacity of AAT has not been compromised by its fusion to an antibody.

Example 3 AAT-Fc-SLPI and AAT-Fc-Elafin

The studies presented herein describe several, non-limiting examples of recombinant AAT derivatives comprising human AAT fused a WAP domain containing protein. These examples are provided below to further illustrate different features of the present invention. The examples also illustrate useful methodology for practicing the invention. The AAT polypeptide portion of the fusion protein is underlined, the Fc portion is italicized, and the WAP domain containing polypeptide is in bold font. While these examples include a hinge sequence and/or a linker sequence, fusion proteins of the invention can be made using any hinge sequence and/or a linker sequence suitable in length and/or flexibility. Alternatively fusion proteins can be made without using a hinge and/or a linker sequence. For example, the polypeptide components can be directly attached.

An exemplary AAT-Fc-SLPI fusion protein is AAT-hFc1-SLPI (human IgG1 Fc), described herein. As shown below, the AAT polypeptide portion of the fusion protein is underlined (SEQ ID NO: 2), the hinge region is shown in normal text (SEQ ID NO: 43), the ASTGS linker is shown in normal text (SEQ ID NO: 45), the Fc portion is italicized (SEQ ID NO: 3), and the WAP domain containing polypeptide is in bold font (SEQ ID NO: 9)

```
AAT-hFc1-SLPI (human IgG1 Fc)
                                     (SEQ ID NO: 28)
EDPQGDAAQKTDTSHHDQDHPTFNKITPNLAEFAFSLYRQLA

HQSNSTNIFFSPVSIATAFAMLSLGTKADTHDEILEGLNFNL

TEIPEAQIHEGFQELLRTLNQPDSQLQLTIGNGLFLSEGLKL

VDKFLEDVKKLYHSEAFTVNFGDTEEAKKQINDYVEKGTQGK

IVDLVKELDRDTVFALVNYIFFKGKWERPFEVKDTEEEDFHV

DQVTTVKVPMMKRLGMFNIQHCKKLSSWVLLMKYLGNATAIF

FLPDEGKLQHLENELTHDIITKFLENEDRRSASLHLPKLSIT

GTYDLKSVLGQLGITKVFSNGADLSGVTEEAPLKLSKAVHKA

VLTIDEKGTEAAGAMFLEAIPMSIPPEVKFNKPFVFLMIEQN

TKSPLFMGKVVVPTQKEPKSCDKTHTCPPCPAPELLGGPSVF

LFPPKPKDTLMISRTPEVTCVVVDVSREDPEVKFNWYVDGVE

VENAKTKPREEQYNSTYRVVSVLTVLHQDWLNGKEYKCKVSN

KALPAPIEKTISKAKGQPREPQVYTLPPSRDELTKNQVSLTC

LVKGFYPSDIAVEWESNGQPENNYKTTPPVLDSDGSFFLYSK

LTVDKSRWQQGNVFSCSVMHEALHNHYTQKSLSLSPGKASTG

SSGKSFKAGVCPPKKSAQCLRYKKPECQSDWQCPGKKRCCPD

TCGIKCLDPVDTPNPTRRKPGKCPVTYGQCLMLNPPNFCEMD

GQCKRDLKCCMGMCGKSCVSPVKA
```

An exemplary AAT-Fc-Elafin fusion protein is AAT-hFc1-Elafin (human IgG1 Fc), described herein. As shown below, the AAT polypeptide portion of the fusion protein is underlined (SEQ ID NO: 2), the hinge region is shown in normal text (SEQ ID NO: 43), the ASTGS linker is shown in normal text (SEQ ID NO: 45), the Fc portion is italicized (SEQ ID NO: 3), and the WAP domain containing polypeptide is in bold font (SEQ ID NO: 12)

```
AAT-hFc1-Elafin (human IgG1 Fc)
                                     (SEQ ID NO: 29)
EDPQGDAAQKTDTSHHDQDHPTFNKITPNLAEFAFSLYRQLA

HQSNSTNIFFSPVSIATAFAMLSLGTKADTHDEILEGLNFNL

TEIPEAQIHEGFQELLRTLNQPDSQLQLTTGNGLFLSEGLKL

VDKFLEDVKKLYHSEAFTVNFGDTEEAKKQINDYVEKGTQGK

IVDLVKELDRDTVFALVNYIFFKGKWERPFEVKDTEEEDFHV

DQVTTVKVPMMKRLGMFNIQHCKKLSSWVLLMKYLGNATAIF

FLPDEGKLQHLENELTHDIITKFLENEDRRSASLHLPKLSIT

GTYDLKSVLGQLGITKVFSNGADLSGVTEEAPLKLSKAVHKA

VLTIDEKGTEAAGAMFLEAIPMSIPPEVKFNKPFVFLMIEQN

TKSPLFMGKVVVPTQKEPKSCDKTHTCPPCPAPELLGGPSVF

LFPPKPKDTLMISRTPEVTCVVVDVSHEDPEVKFNWYVDGVE

VENAKTKPREEQYNSTYRVVSVLTVLHQDWLNGKEYKCKVSN

KALPAPIEKTISKAKGQPREPQVYTLPPSRDELTKNQVSLTC

LVKGFYPSDIAVEWESNGQPENNYKTTPPVLDSDGSFFLYSK

LTVDKSRWQQGNVFSCSVMHEALHNHYTQKSLSLSPGKASTG

SAVTGVPVKGQDTVKGRVPFNGQDPVKGQVSVKGQDKVKAQE

PVKGPVSTKPGSCPIILIRCAMLNPPNRCLKDTDCPGIKKCC

EGSCGMACFVPQ
```

The genes encoding the SLPI and Elafin were PCR amplified from human spleen cDNA (Zyagen). These genes were cloned into the mammalian expression vectors of example 1, wherein the SLPI or Elafin gene was inserted in frame with the AAT-Fc gene. These expression vectors were transfected into mammalian cells (specifically HEK293 or CHO cells) and grown for several days in 8% $CO_2$ at 37° C. The recombinant AAT-Fc-WAP domain fusion proteins were purified from the expression cell supernatant by protein A chromatography. A near neutral pH buffer was used (Gentle Ag/Ab Elution Buffer, Thermo Scientific) to elute the AAT-Fc-WAP domain fusion protein from the protein A resin.

Figure 3A:
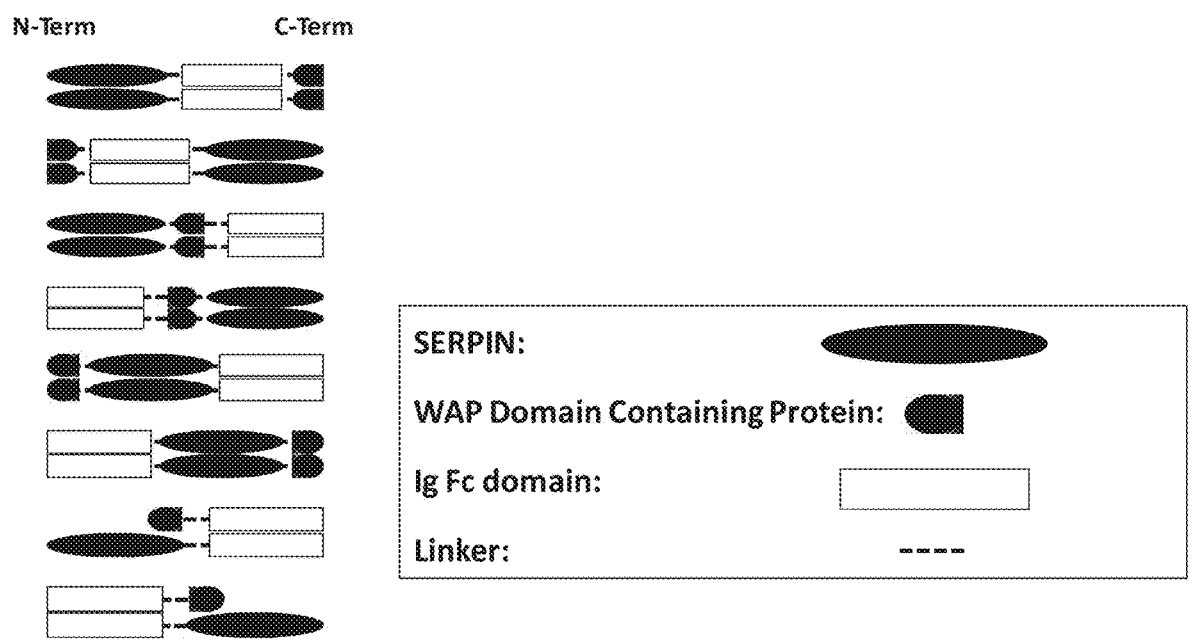
FIG. 3A is a schematic representation of some embodiments of the serpin-Fc-WAP fusion proteins.
Figure 3B:
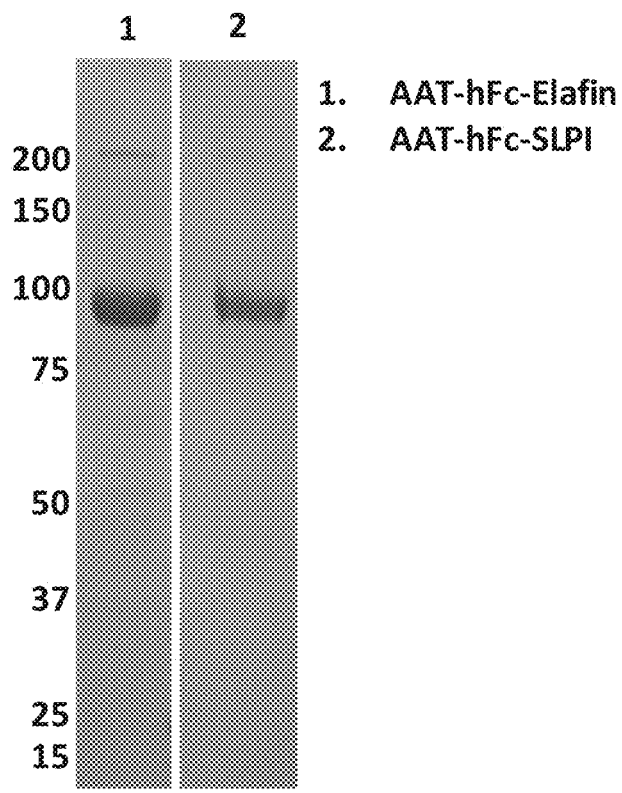
FIG. 3B is a photograph of a SDS-PAGE gel showing AAT-Fc-ELAFIN (lane 1) and AAT-Fc-SLPI (lane 2).
Figure 3C:
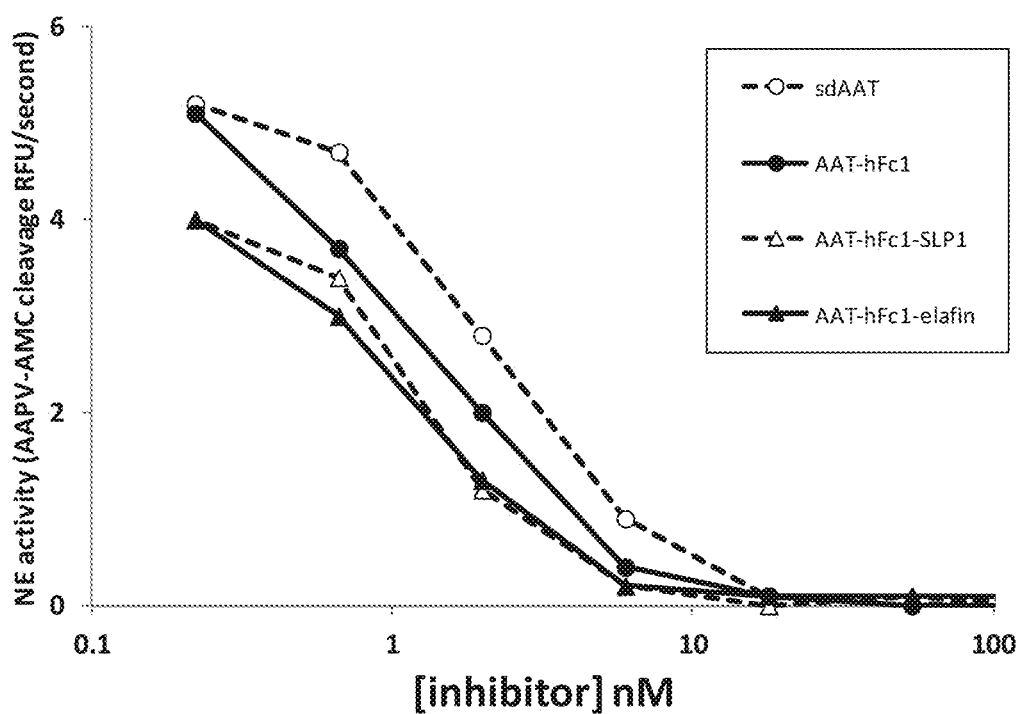
FIG. 3C is a graph showing the inhibition of neutrophil elastase activity by an AAT-Fc-ELAFIN fusion protein and an AAT-Fc-SLPI fusion protein. An AAT-Fc fusion protein and serum derived AAT are included for comparison.

FIG. 3B shows an SDS-PAGE gel of the AAT-Fc-WAP fusion proteins (lane 1 AAT-Fc-Elafin, lane 2 AAT-Fc-SLPI). The proteins were visualized by staining with coomassie blue. The purified AAT-Fc-WAP domain fusion proteins were tested for activity by determining their ability to inhibit neutrophil elastase. NE inhibitory assays were conducted as described above. Human serum derived AAT (sdAAT) and the AAT-Fc fusion protein were used as a positive control in these assays. Relative to sdAAT, the AAT-Fc-WAP targeting molecule fusion proteins display enhanced potency of NE inhibition of neutrophil elastase (FIG. 3C).

Example 4 AAT-Albumin

The studies presented herein describe several, non-limiting examples of recombinant AAT derivatives comprising human AAT fused an albumin polypeptide. These examples are provided below to further illustrate different features of the present invention. The examples also illustrate useful methodology for practicing the invention. These examples do not and are not intended to limit the claimed invention. The AAT portion is underlined and the albumin portion is italicized. For example, the polypeptide components can be directly attached.

An exemplary AAT-Albumin fusion protein is AAT-HSA, described herein. As shown below, the AAT polypeptide portion of the fusion protein is underlined (SEQ ID NO: 2), the ASTGS linker is shown in normal text (SEQ ID NO: 45), and the albumin polypeptide is italicized (SEQ ID NO: 14)

AAT-HSA
(SEQ ID NO: 30)
EDPQGDAAQKTDTSHHDQDHPTFNKITPNLAEFAFSLYRQLAHQ

SNSTNIFFSPVSIATAFAMLSLGTKADTHDEILEGLNFNLTEIP

EAQIHEGFQELLRTLNQPDSQLQLTTGNGLFLSEGLKLVDKFLE

DVKKLYHSEAFTVNFGDTEEAKKQINDYVEKGTQGKIVDLVKEL

DRDTVFALVNYIFFKGKWERPFEVKDTEEEDFHVDQVTTVKVPM

MKRLGMFNIQHCKKLSSWVLLMKYLGNATAIFFLPDEGKLQHLE

NELTHDIITKFLENEDRRSASLHLPKLSITGTYDLKSVLGQLGI

TKVFSNGADLSGVTEEAPLKLSKAVHKAVLTIDEKGTEAAGAMF

LEAIPMSIPPEVKFNKPFVFLMIEQNTKSPLFMGKVVNPTQKAS

TGS*DAHKSEVAHRFKDLGEENFKALVLIAFAQYLQQCPFEDHVK*

*LVNEVTEFAKTCVADESAENCDKSLHTLFGDKLCTVATLRETYG*

*EMADCCAKQEPERNECFLQHKDDNPNLPRLVRPEVDVMCTAFHD*

*NEETFLKKYLYEIARRHPYFYAPELLFFAKRYKAAFTECCQAAD*

*KAACLLPKLDELRDEGKASSAKQRLKCASLQKFGERAFKAWAVA*

*RLSQRFPKAEFAEVSKLVTDLTKVHTECCHGDLLECADDRADLA*

*KYICENQDSISSKLKECCEKPLLEKSHCIAEVENDEMPADLPSL*

*AADFVESKDVCKNYAEAKDVFLGMFLYEYARRHPDYSVVLLLRL*

*AKTYETTLEKCCAAADPHECYAKVFDEFKPLVEEPQNLIKQNCE*

*GLFEQLGEYKFQNALLVRYTKKVPQVSTPTLVEVSRNLGKVSKC*

*CKHPEAKRMPCAEDYLSVVLNQLCVLHEKTPVSDRVTKCCTESL*

*VNRRPCFSALEVDETYVPKEFNAETFTFHADICTLSEKERQIKK*

*QTALVELVKHKPKATKEQLKAVMDDFAAFVEKCCKADDKETCFA*

*EEGKKLVAASQAALGL*

An exemplary AAT-Albumin fusion protein is AAT-HSA Domain 3, described herein. As shown below, the AAT polypeptide portion of the fusion protein is underlined (SEQ ID NO: 2), ASTGS linker is shown in normal text (SEQ ID NO: 45), and the albumin polypeptide is italicized (SEQ ID NO: 15)

AAT-HSA Domain 3
(SEQ ID NO: 31)
EDPQGDAAQKTDTSHHDQDHPTFNKITPNLAEFAFSLYRQLAHQ

SNSTNIFFSPVSIATAFAMLSLGTKADTHDEILEGLNFNLTEIP

-continued
EAQIHEGFQELLRTLNQPDSQLQLTIGNGLFLSEGLKLVDKFLE

DVKKLYHSEAFTVNFGDTEEAKKQINDYVEKGTQGKIVDLVKEL

DRDTVFALVNYIFFKGKWERPFEVKDTEEEDFHVDQVTTVKVPM

EMKRLGMFNIQHCKKLSSWVLLMKYLGNATAIFFLPDGKLQHLE

NELTHDIITKFLENEDRRSASLHLPKLSITGTYDLKSVLGQLGI

TKVFSNGADLSGVTEEAPLKLSKAVHKAVLTIDEKGTEAAGAMF

LEAIPMSIPPEVKFNKPFVFLMIEQNTKSPLFMGKVVNPTQKAS

TGS*EEPQNLIKQNCELFEQLGEYKFQNALLVRYTKKVPQVSTPT*

*LVEVSRNLGKVGSKCCKHPEAKRMPCAEDYLSVVLNQLCVLEEK*

*TPVSDRVTKCCTESLVNRRPCFSALEVDETYVPKEFNAETFTFH*

*ADICTLSEKERQIKKQTALVELVKHKPKATKEQLKAVMDDFAAF*

*VEKCCKADDKETCFAEEGKKLVA*

The gene encoding human serum albumin (HSA) was PCR amplified from human liver cDNA (Zyagen). A mammalian expression vector was generated, wherein gene encoding HSA or the domain 3 of HSA, was cloned in frame to the 3' end of the AAT encoding gene, containing a mammalian secretion signal sequence up stream of AAT.

These expression vectors were transfected into mammalian cells (specifically HEK293 or CHO cells) and grown for several days in 8% $CO_2$ at 37° C. The recombinant AAT-HSA fusion proteins were purified from the expression cell supernatant using the CaptureSelect® Alpha-1 Antitrypsin affinity matrix (BAC BV), wherein the binding buffer consisted of 20 mM Tris, 150 mM NaCl, pH 7.4 and the elution buffer consisted of 20 mM Tris, 2M $MgCl_2$ pH 7.4.

Figure 4A:
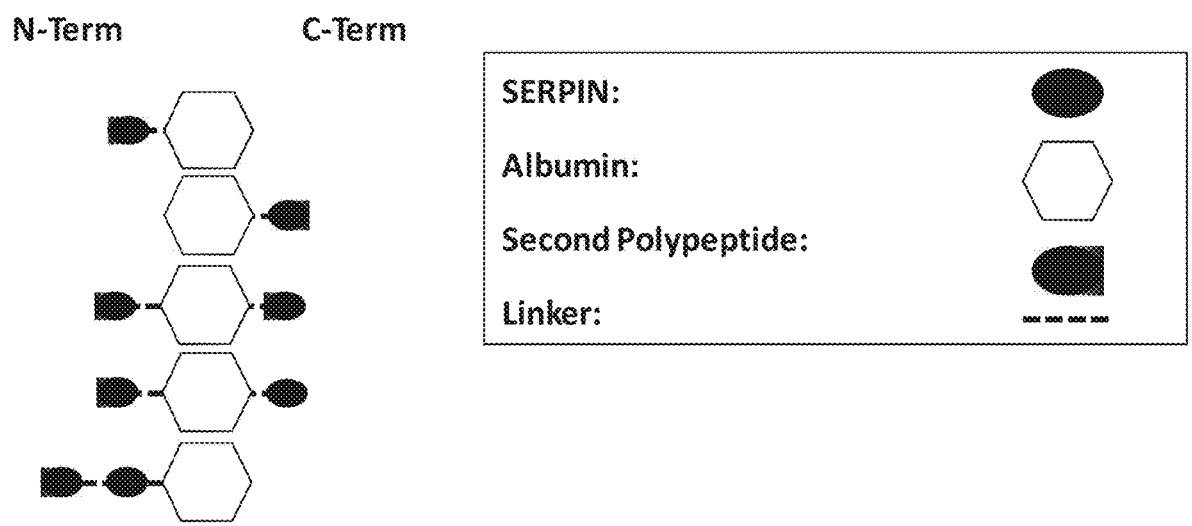
FIG. 4A is a schematic representation of some embodiments of the AAT-HSA fusion proteins.
Figure 4B:
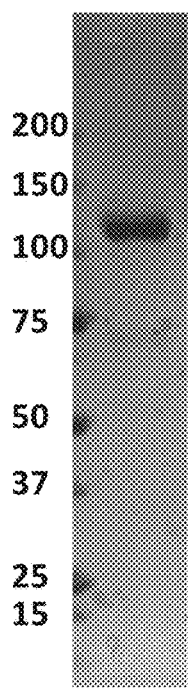
FIG. 4B is a photograph of a SDS-PAGE gel showing an AAT-HSA fusion.
Figure 4C:
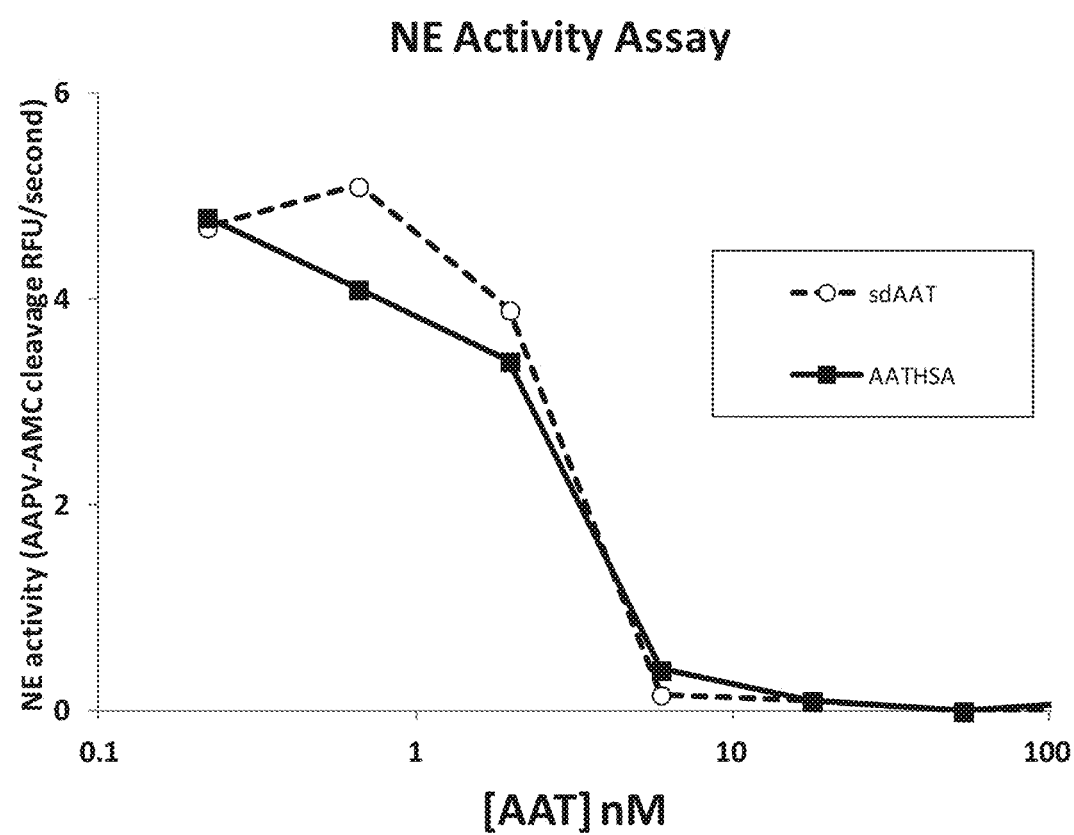
FIG. 4C is a graph showing the inhibition of neutrophil elastase activity by an AAT-HSA compared to serum derived AAT.

FIG. 4B shows an SDS-PAGE gel of the AAT-HSA fusion protein The proteins were visualized by staining with coomassie blue. The purified AAT-HSA fusion proteins were tested for activity by determining their ability to inhibit neutrophil elastase. NE inhibitory assays were conducted as described above. Human serum derived AAT (sdAAT) was used as a positive control in these assays. Relative to sdAAT, the AAT-HS fusion protein displays similar potency of NE inhibition, demonstrating that the fusion to albumin does not dampen the capacity of AAT to inhibit NE (FIG. 4C.)

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated fusion protein comprising at least one alpha-1 antitrypsin (AAT) polypeptide operably linked to a second polypeptide, wherein the second polypeptide comprises a human serum albumin (HSA) polypeptide, and wherein the fusion protein comprises the amino acid sequence of SEQ ID NO: 30 or 31.

2. A method of inhibiting or downregulating aberrant serine protease expression or activity in a subject in need thereof, the method comprising administering an isolated fusion protein according to claim 1.

3. The method of claim 2, wherein the subject is a human.

4. The method of claim 2, wherein the subject has a disease or disorder selected from the following: alpha-1 antitrypsin (AAT) deficiency, an infection, emphysema, chronic obstructive pulmonary disease (COPD), acute respiratory distress syndrome (ARDS), allergic asthma, cystic fibrosis, cancers of the lung, ischemia-reperfusion injury, ischemia/reperfusion injury following cardiac transplantation, myocardial infarction, rheumatoid arthritis, septic arthritis, psoriatic arthritis, ankylosing spondylitis, Crohn's disease, psoriasis, type I diabetes, type II diabetes, pneumonia, sepsis, graft versus host disease (GVHD), a wound, systemic lupus erythematosus, and multiple sclerosis.

5. The method of claim 4, wherein the infection is selected from a bacterial infection, a fungal infection, or a viral infection.

* * * * *